United States Patent [19]

Los

[11] Patent Number: 4,701,208

[45] Date of Patent: Oct. 20, 1987

[54] DIHYDROIMIDAZOPYRROLOPYRIDINE, QUINOLINE, THIENO- AND FURO[2,3-b]PYRIDINE, DIHYDROTHIENO- AND FURO[2,3,b]-PYRIDINE, THIENO- AND FURO[3,2-b]PYRIDINE AND DIHYDROTHIENO- AND FURO[3,2-b]PYRIDINE HERBICIDES AND METHOD FOR PREPARATION THEREOF

[75] Inventor: Marinus Los, Pennington, N.J.

[73] Assignee: American Cyanamid Company, Stamford, Conn.

[21] Appl. No.: 624,437

[22] Filed: Jun. 25, 1984

Related U.S. Application Data

[63] Continuation-in-part of Ser. No. 519,603, Aug. 2, 1983, abandoned.

[51] Int. Cl.$^4$ .................. C07D 487/14; A01N 43/40
[52] U.S. Cl. .......................................... 71/92; 71/90; 546/15; 546/64; 546/82
[58] Field of Search ............... 546/82, 64, 15; 71/90, 71/92

[56] References Cited

U.S. PATENT DOCUMENTS

| 4,041,045 | 8/1977 | Los | 71/92 |
| 4,125,727 | 11/1978 | Los | 548/301 |

FOREIGN PATENT DOCUMENTS

| 41624 | 12/1981 | European Pat. Off. | 71/92 |
| 41623 | 12/1981 | European Pat. Off. | 71/92 |

Primary Examiner—Donald G. Daus
Assistant Examiner—William A. Teoli, Jr.
Attorney, Agent, or Firm—H. G. Jackson

[57] ABSTRACT

This invention relates to novel herbicidally effective, dihydroimidazopyrrolopyridines and derivatives thereof which are useful for the control of undesirable monocotyledonous and dicotyledonous plant species. The invention also relates to a process for the preparation of said herbicidally effective compounds.

21 Claims, No Drawings

DIHYDROIMIDAZOPYRROLOPYRIDINE, QUINOLINE, THIENO- AND FURO[2,3-b]PYRIDINE, DIHYDROTHIENO- AND FURO[2,3-b]-PYRIDINE, THIENO- AND FURO[3,2-b]PYRIDINE AND DIHYDROTHIENO- AND FURO[3,2-b]PYRIDINE HERBICIDES AND METHOD FOR PREPARATION THEREOF

This application is a continuation-in-part of copending application Ser. No. 519,603 filed Aug. 2, 1983, now abandoned.

This invention relates to novel herbicidally effective, dihydroimidazopyrrolopyridines and derivatives thereof which are useful for the control of undesirable monocotyledonous and dicotyledonous plant species. The invention also relates to a process for the preparation of said herbicidally effective compounds.

More particularly, this invention relates to novel, herbicidally effective, dihydroimidazopyrrolopyridines, quinolines, thieno- and furo[2,3-b]pyridines, dihydrothieno- and furo[2,3-b]pyridines, thieno- and furo[3,2-b]pyridines and dihydrothieno- and furo[3,2-b]pyridines depicted by formula (I) below:

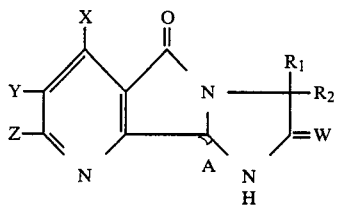

wherein $R_1$ and $R_2$ each represent $C_1$-$C_3$ alkyl or cyclopropyl, with the proviso that the sum of the number of carbon atoms in $R_1$ and $R_2$ is 2 to 5; and when $R_1$ and $R_2$ are taken together with the carbon to which they are attached, they may form a $C_3$-$C_6$ cycloalkyl ring optionally substituted with methyl;

W is oxygen or sulfur;

A is hydrogen, hydroxyl, $C_3$-$C_6$ alkenyloxy, $C_3$-$C_6$ alkynyloxy, $C_1$-$C_6$ alkylthio, $NR_{13}R_{14}$ or $C_1$-$C_6$ alkoxy optionally substituted with phenyl, halophenyl, $C_1$-$C_3$ alkylphenyl, $C_1$-$C_3$ alkoxyphenyl or di-$C_1$-$C_3$ alkylaminophenyl;

$R_{13}$ is hydrogen, $C_1$-$C_4$ alkyl optionally substituted with phenyl, halophenyl, $C_1$-$C_3$ alkylphenyl or $C_1$-$C_3$ alkoxyphenyl;

$R_{14}$ is hydrogen or $C_1$-$C_4$ alkyl;

X is hydrogen, halogen or methyl;

Y and Z are each hydrogen, halogen, $C_1$-$C_6$ alkyl, $C_1$-$C_4$ hydroxyalkyl, $C_1$-$C_6$ alkoxy, $C_1$-$C_4$ alkylthio, phenoxy, $C_1$-$C_4$ haloalkyl, $OCF_2CHF_2$, $OCF_3$, $OCHF_2$, nitro, cyano, $NR_4R_5$, $C_3$-$C_8$ straight or branched alkenyloxy optionally substituted with one to three halogens, $C_3$-$C_8$ straight or branched alkynyloxy optionally substituted with one to three halogens, or phenyl optionally substituted with one $C_1$-$C_4$ alkyl, $C_1$-$C_4$ alkoxy or halogen;

$R_4$ is hydrogen or $C_1$-$C_4$ alkyl;

$R_5$ is $C_1$-$C_4$ alkyl;

And, when taken together, Y and Z may form a ring in which YZ is represented by (1) the structure: $-(CH_2)_n-$, where n is an integer of 2, 3 or 4, provided that X is hydrogen; or (2) by the structure:

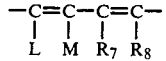

where, L, M, $R_7$ and $R_8$ each represent hydrogen, halogen, $C_1$-$C_4$ alkyl, $C_1$-$C_4$ alkoxy, $C_1$-$C_4$ alkylthio, $C_1$-$C_4$ alkylsulfonyl, $C_1$-$C_4$ haloalkyl, $NO_2$, CN, phenyl, phenoxy, amino, $OCF_3$, $OCHF_2$, $OCF_2CHF_2$, $C_1$-$C_4$ alkylamino, dialkyl($C_1$-$C_4$)amino, chlorophenyl, methylphenyl, $C_3$-$C_8$ straight or branched alkenyloxy optionally substituted with one to three halogens, $C_3$-$C_8$ straight or branched alkynyloxy optionally substituted with one to three halogens, or phenoxy substituted with one Cl, $CF_3$, $NO_2$ or $CH_3$ group, with the proviso that only one of L, M, $R_7$ or $R_8$ may represent a substituent other than hydrogen, halogen, $C_1$-$C_4$ alkyl or $C_1$-$C_4$ alkoxy; or (3) by the structures:

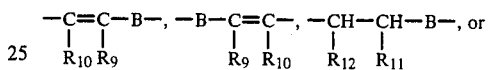

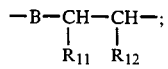

where B is oxygen or sulfur; $R_9$ and $R_{10}$ each represent hydrogen, halogen, phenyl, or $C_1$-$C_4$ alkyl; $R_{11}$ and $R_{12}$ each represent hydrogen, $C_1$-$C_4$ alkyl or phenyl;

and when $R_1$ and $R_2$ are not the same, the cis- or trans-isomers or mixtures thereof or the optical isomers (cis- or trans- or mixtures thereof).

As used in the present specification and claims, the term "halogen" means F, Cl, Br or I, unless otherwise specified.

It should, of course, be understood that when $R_1$ and $R_2$ are not the same, the formula (I) compounds can exist as both the cis- and trans-isomers. These can be illustrated as follows:

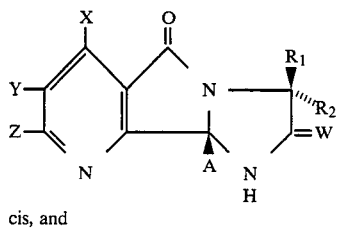

cis, and

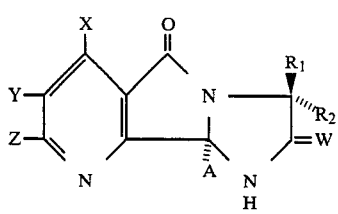

trans.

Especially preferred compounds of the present invention are more precisely illustrated by formulas II, III, IV, V, VI, VII and VIII shown below.

Preferred dihydroimidazopyrrolopyridine compounds of this invention are depicted by formula (II), hereinafter illustrated:

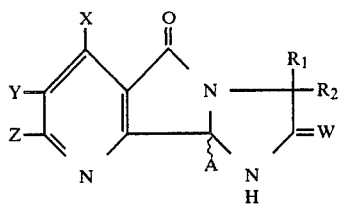

wherein A, $R_1$, $R_2$, W and X are as defined in reference to formula I above; Y and Z each, independently, represent hydrogen, halogen, $C_1$-$C_6$ alkyl, $C_1$-$C_6$ alkoxy, CN, $NO_2$, $OCF_3$, $OCHF_2$, $OCF_2CHF_2$, phenoxy, $C_1$-$C_4$ haloalkyl, $C_1$-$C_4$ alkylthio, $C_1$-$C_4$ hydroxyalkyl, $NR_4R_5$, $C_3$-$C_8$ straight or branched alkenyloxy optionally substituted with one to three halogens, $C_3$-$C_8$ straight or branched alkynyloxy optionally substituted with one to three halogens, or phenyl optionally substituted with one $C_1$-$C_4$ alkyl, $C_1$-$C_4$ alkoxy or halogen; $R_4$ is hydrogen or $C_1$-$C_4$ alkyl; $R_5$ is $C_1$-$C_4$ alkyl; and when taken together Y and Z may form a ring in which YZ are represented by the structure: —$(CH_2)_n$—, wheren is an integer of 2, 3 or 4; and when $R_1$ and $R_2$ are not the same, the cis- or trans-isomers or mixtures thereof or the optical isomers (cis- or trans- or mixtures thereof).

Preferred dihydroimidazopyrroloquinolines are illustrated by formula (III):

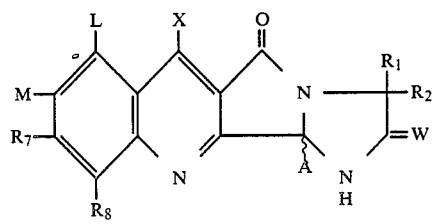

wherein A, $R_1$, $R_2$, W and X, are as defined above in reference to formula I, and L, M, $R_7$ and $R_8$ represent hydrogen, halogen, $C_1$-$C_4$ alkyl, $C_1$-$C_4$ alkoxy, $C_1$-$C_4$ alkylthio, $C_1$-$C_4$ alkylsulfonyl, $C_1$-$C_4$ haloalkyl, $NO_2$, CN, phenyl, phenoxy, amino, $CF_3$, $OCHF_2$, $OCF_2CHF_2$, $C_1$-$C_4$ alkylamino, dialkyl($C_1$-$C_4$)amino, chlorophenyl, methylphenyl, $C_3$-$C_8$ straight or branched alkenyloxy optionally substituted with one to three halogens, $C_3$-$C_8$ straight or branched alkynyloxy optionally substituted with one to three halogens, or phenoxy substituted with one Cl, $CF_3$, $NO_2$ or $CH_3$ group, with the proviso that only one of L, M, $R_7$ or $R_8$, may represent a substituent other than hydrogen, halogen, $C_1$-$C_4$ alkyl or $C_1$-$C_4$ alkoxy; and when $R_1$ and $R_2$ are not the same, the cis- or trans-isomers or mixtures thereof or the optical isomers (cis- or trans- or mixtures thereof).

Preferred dihydroimidazopyrrolothieno- and furo[3,2-b]pyridines and dihydroimidazopyrrolodihydrothieno- and furo[3,2-b]pyridines are, respectively, illustrated by formulas (V) and (VI), shown below:

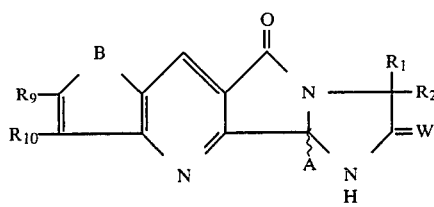

and,

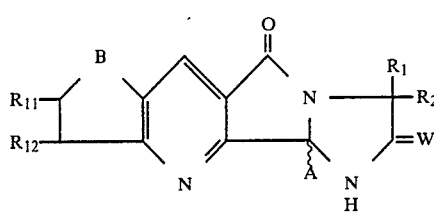

wherein A, $R_1$, $R_2$, W and B, are as defined above in reference to formula I; $R_9$ and $R_{10}$ each represent hydrogen, halogen, $C_1$-$C_4$ alkyl or phenyl; and $R_{11}$ and $R_{12}$ each represent hydrogen, $C_1$-$C_4$ alkyl or phenyl; and when $R_1$ and $R_2$ are not the same, the cis- or trans-isomers or mixtures thereof or the optical isomers (cis- or trans- or mixtures thereof).

The preferred dihydroimidazopyrrolothieno- and furo[2,3-b]pyridines and the dihydroimidazopyrrolodihydrothieno- and furo[2,3-b]pyridines are, respectively, depicted by formulas (VII) and (VIII) illustrated as follows:

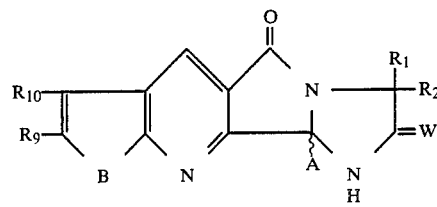

and,

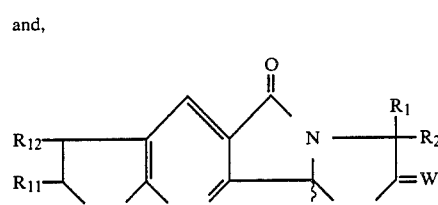

wherein A, $R_1$, $R_2$, W and B, are as defined above in reference to formula I, $R_9$ and $R_{10}$ each represent hydrogen, halogen, $C_1$-$C_4$ alkyl or phenyl; $R_{11}$ and $R_{12}$ each represent hydrogen, $C_1$-$C_4$ alkyl or phenyl; and when $R_1$ and $R_2$ are not the same, the cis- or trans-isomers or mixtures thereof or the optical isomers (cis- or trans- or mixtures thereof).

It is obvious that in the case of formula (VI) and (VIII) that when either $R_{11}$ or $R_{12}$ is other than hydrogen, additional optical and cis- and trans-isomers are possible, and all of these are considered to be within the scope of the invention.

Although dihydroimidazoisoindolediones are described as herbicidal agents in U.S. Pat. No. 4,041,045 issued Aug. 9, 1977, said publication does not render the compounds of this invention obvious since it does not disclose or imply the disclosure of herbicidal compounds containing a pyridine or substituted pyridine ring. Moreover, it is surprising to find that the formula I compounds of this invention are frequently found to be highly selective herbicidal agents effective for the preemergence and postemergence control of a wide variety of undesirable broadleaf weeds and grasses in the presence of graminaceous crops such as corn, rice and wheat; leguminous crops such as soybeans and in the presence of a variety of other crops including cotton.

In accordance with the process of the present invention, the novel formula (I) dihydroimidazopyrrolopyridines, quinolines and the like can be prepared by reaction of the appropriately substituted or unsubstituted formula (XII) 2-(2-imidazolidinyl)nicotinic acid; 2-(2-imidazolidinyl)quinoline-3-carboxylic acid; 2(2-imidazolidinyl)thieno- or furo[3,2-b]pyridine-6-carboxylic acid; 2-(2-imidazolidinyl)dihydrothieno- or furo[3,2-b]pyridine-6-carboxylic acid; 2-(2-imidazolidinyl)thieno- or furo[2,3-b]pyridine-5-carboxylic acid or 2-(2-imidazolidinyl)dihydrothieno or furo[2,3-b]pyridine-5-carboxylic acid, with at least one molar equivalent and preferably a slight excess of acetic anhydride in the presence of pyridine and acetonitrile.

In practice, it is generally desirable to warm the reaction mixture to about 40° to 60° C. until an essentially clear solution is obtained. Cooling of the thus-prepared solution to about ambient temperature or below then yields the desired formula (I) dihydroimidazopyrrolopyridine, quinoline, thieno or furo-pyridine or dihydrothieno or furopyridine, corresponding to the isomeric mixture of the substituted or unsubstituted acid employed as starting material for the reaction.

The reaction may be graphically illustrated as follows:

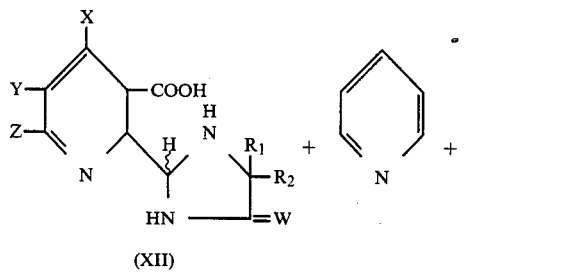

(XII)

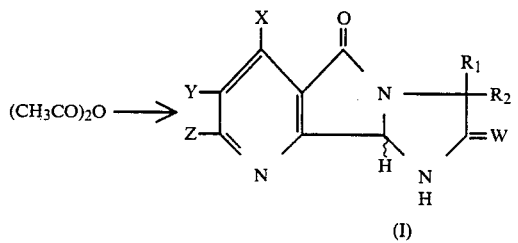

(I)

wherein X, Y, Z, $R_1$, $R_2$ and W are as described for formula (I) above.

Similarly, in an alternate procedure it has also been found that the substituted or unsubstituted 2-(2-imidazolidinyl)nicotinic acid; 2-(2-imidazolidinyl)-quinoline-3-carboxylic acid; 2-(2-imidazolidinyl)thieno- or furo[3,2-b]pyridine-6-carboxylic acid; 2-(2-imidazolidinyl)dihydrothieno- or furo[3,2-b]pyridine-6-carboxylic acid; 2-(2-imidazolidinyl)thieno- or furo[2,3-b]pyridine-5-carboxylic acid or 2-(2-imidazolidinyl)-dihydrothieno- or furo[2,3-b]pyridine-5-carboxylic acid, which are themselves pre- and postemergence herbicides, can be converted to the corresponding formula (I) dihydroimidazopyrrolopyridine, quinoline, thieno- or furo[3,2-b]pyridine, dihydrothieno- or furo[3,2-b]pyridine, thieno- or furo[2,3-b]pyridine or the dihydrothieno- or furo[2,3-b]pyridine, by reaction thereof with at least an equimolar amount of N,N'-dicyclohexylcarbodiimide in the presence of a chlorinated hydrocarbon solvent such as methylene chloride, dichloroethane, chloroform or the like. The reaction may be conducted at ambient temperature and yields the desired formula (I) compound on evaporation or separation of the solvent from the reaction mixture. The reaction may be graphically illustrated as follows:

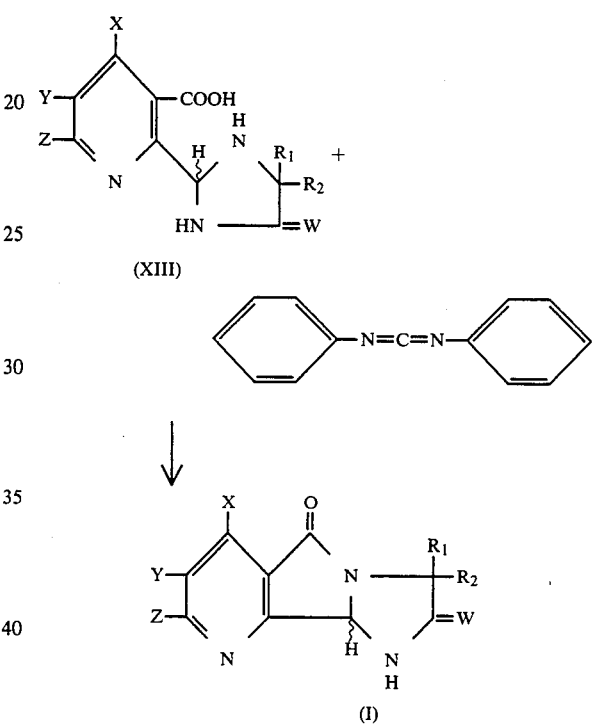

wherein $R_1$, $R_2$, X, Y, Z and W are as description with respect to formula (I) above. It should be understood that if a cis-, trans- or mixture of cis- and trans-imidazolidinone is employed as starting material in the above reactions, then the cis-, trans- or mixture of cis- and trans- formula (I) compounds is obtained. These formula (I) dihydroimidazopyrrolopyridines, quinolines, thieno- and furopyridines and dihydrothieno- and furopyridines, are unexpectedly substantially more selective than their 2-(2-imidazolidinyl)acid precursors.

Many of the formula (I) dihydroimidazopyrrolopyridine, quinoline, thieno- and furopyridine and dihydrothieno- and furopyridine, compounds of the present invention may also be prepared by reduction of the corresponding formula (XIV) 5H-imidazopyrrolopyridine, quinoline, thieno- or furopyridine, or dihydrothieno- or furopyridine, 2,5-dione. This reduction can be achieved by reaction of the formula (XIV) 2,5-dione with at least an equimolar amount of a reducing agent such as sodium or lithium borohydride in alcohol or aqueous alcohol or tetrahydrofuran or aqueous tetrahydrofuran, at a temperature between about −10° and +5° C. Acidification of the reaction mixture to a pH of about 3, using a strong mineral acid such as concentrated sulfuric acid, then yields the desired formula (I) product. The reaction may be graphically illustrated as follows:

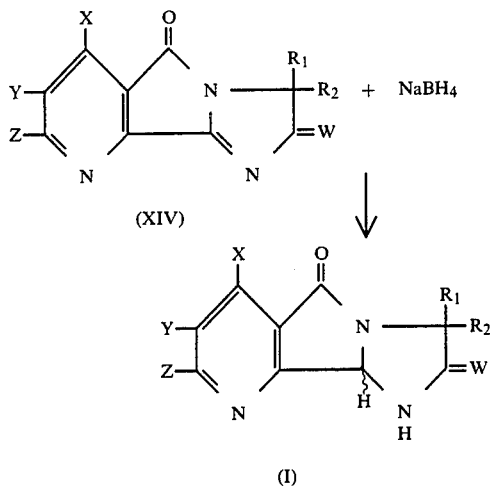

wherein X, Y, Z, W, $R_1$ and $R_2$ are as described with respect to formula (I) above.

This procedure usually forms a mixture of the cis and trans-isomers of the formula (I) compounds.

The preparation of the formula XIV 5H-imidazopyrrolopyridines and imidazopyrroloquinolines in which W is oxygen is described in the European Patent Application No. 0,041,623, published Dec. 16, 1981.

In all the cases described above, the products from the reaction are those in which A is hydrogen. In order to prepare these compounds in which A is a group other than hydrogen, advantage is taken of the ability of the >C=N— function in the imidazopyraolopyridines, quinolines, thieno- and furopyridines to add a variety of nucleophiles such as alcohols, amines and thiols. The reaction may be graphically illustrated as follows:

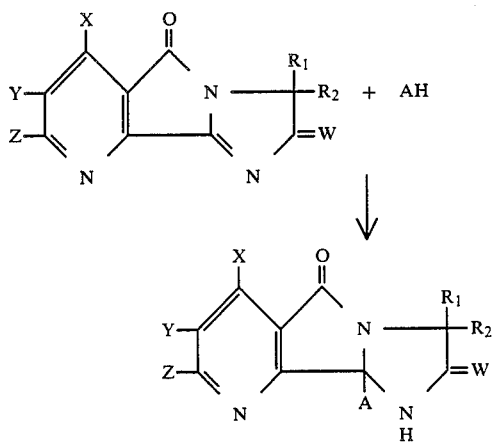

wherein AH is, for example, $CH_3OH$, $CH_3SH$, $CH_3NH_2$. This reaction may be catalyzed by acids such as p-toluenesulfonic acid or bases such as tertiary amines.

In practice it has been found that many substituted and unsubstituted aromatic and heteroaromatic imidazolidinone and imidazolidinethione compounds utilized as starting materials for the above described reactions by formula (I) can be prepared by reduction of the corresponding formula (XV) imidazolinone or imidazolinethione with, for example, at least about an equimolar amount of sodium cyanoborohydride in the presence of a solvent such as $C_1$-$C_4$ aliphatic alcohol, aqueous alcoholic mixture or ether, followed by acidification to a pH between about 2.5 and 5 and preferably between 3 and 4, with a strong mineral acid such as hydrochloric acid, or an organic acid such as acetic or the like. This reduction is generally conducted at a temperature between 0° and 40° C. and is particularly effective for treatment of 2-(2-imidazolinyl)nicotinic acids and esters, but preferably the methyl esters. It is likewise effective for reduction of the imidazolinyl function 2-(2-imidazolinyl)thieno and furo[3,2-b]pyridine-6-carboxylic acid esters and 2-(2-imidazolinyl)-thieno and furo[2,3-b]pyridine-5-carboxylic acid esters.

The above described reduction may be graphically illustrated as follows:

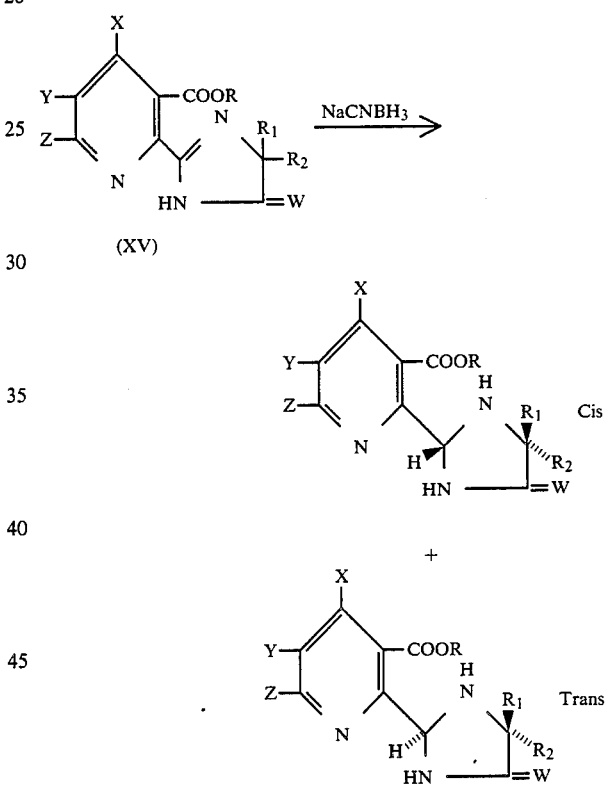

wherein R may be hydrogen, but preferably a methyl group and $R_1$, $R_2$, W, X, Y and Z, are as defined in reference to said formula I. When R is a methyl group then this can advantageously be removed by reaction of the methyl ester in a $C_1$-$C_4$ aliphatic alcohol, preferably absolute methanol, and admixing therewith at least one equivalent of strong base.

As shown above, the imidazolidinones and imidazolidinethiones are obtained as a mixture of cis- and trans-isomers when $R_1$ and $R_2$ are not the same. These isomers are obtained in variable amounts. The mixtures are useful as such, but can frequently be separated chromatographically to give the pure cis- and trans-isomers, both of which are effective herbicidal agents.

Since the above-described reduction is not a universal method for the preparation of all substituted and unsubstituted aromatic and heteroaromatic imidazolidinones and imidazolidinethiones, a variety of synthetic routes have been explored in order to provide effective procedures for the manufacture of the imidazolidinones and imidazolidinethiones employed as starting materials for the preparation of the formula (I) compounds of this invention.

Accordingly, it has now been determined that both the oxo and thioxo derivatives of 2-(2-imidazolidinyl)-nicotinates and 2-(2-imidazolidinyl)quinoline-3-carboxylates can be synthesized by heating to refluxing temperature, a mixture of a formula IX aminoamide or aminothioamide with about an equimolar amount of an appropriate formula X .substituted or unsubstituted lower alkyl, 2-formylpyridine-3-carboxylate or 2-formylquinoline-3-carboxylate, in the presence of an inert organic solvent such as benzene, toluene, or the like, and a strong organic acid, such as p-toluenesulfonic acid, under a blanket of nitrogen. The thus-formed ester may then be converted to the corresponding formula (XII), acid, used as starting materials in the synthesis of the formula (I) compounds of the present invention, by dissolving or dispersing the imidazolidinone ester or imidazolidinethione ester in a $C_1$–$C_4$ aliphatic alcohol, preferably absolute methanol and admixing therewith at least one equivalent of strong base. In practice, the base is generally dissolved in water and the mixture heated to between about 20° and 50° C. The mixture is then cooled and adjusted to pH 6.5 to 7.5, and preferably about pH 7, with a strong mineral acid such as hydrochloric acid to yield the imidazolidinone or imidazolidinethione acid wherein $R_1$, $R_2$, $R_3$, W, X, Y and Z are as defined above. The reaction is illustrated in Flow Diagram (I).

FLOW DIAGRAM I

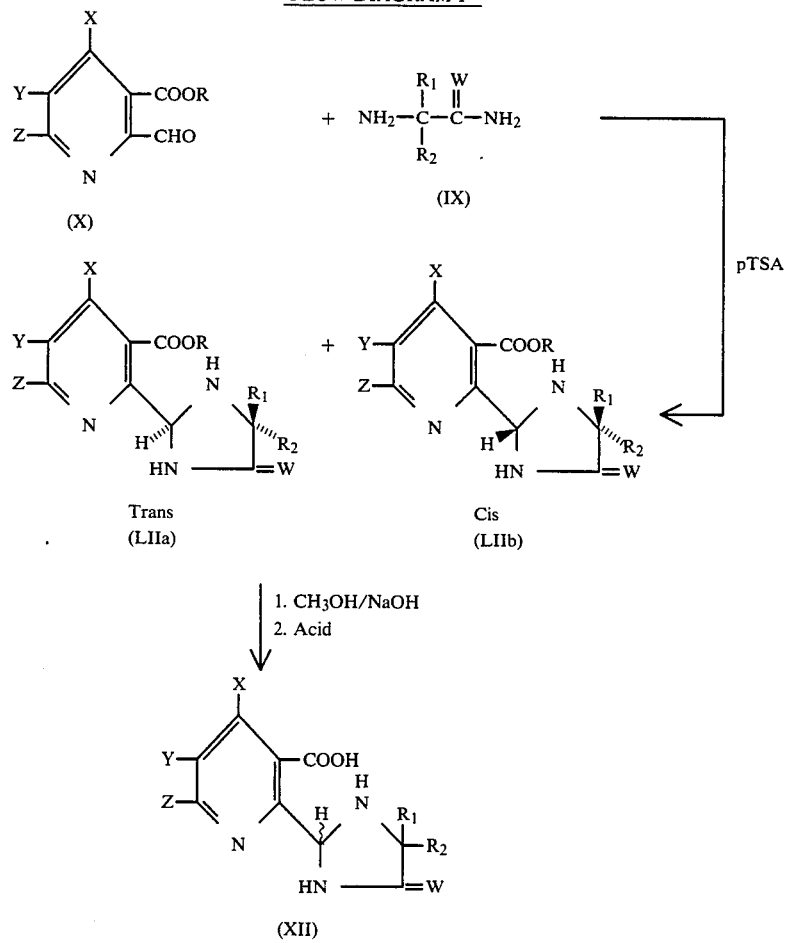

wherein R is $C_1$–$C_4$ alkyl; and $R_1$, $R_2$, X, Y, Z and W are as described for formula (I) above.

The reaction of an aldehyde of formula (X) with an α-aminoamide or thioamide of formula (IX) under acid catalysis gives the corresponding Schiff's base as the initial product. Whether the Schiff's base of general formula

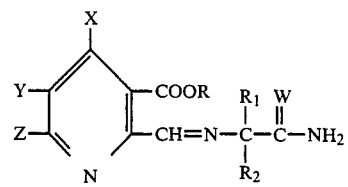

is isolated as such or cyclizes under the reaction conditions to the desired imidazolidinone depends on some unknown subtle factors. Nevertheless, if the Schiff's base is isolated it can, in a separate reaction, be cyclized with trifluoroacetic acid to the imidazolidinone.

Substituted $C_1$–$C_4$ alkyl 2-formylnicotinates which are useful in the preparation of 2-(2-imidazolidinyl)-nicotinatic acids and esters by the aldehyde route described above and illustrated in Flow Diagram I, for synthesis of formula LIIa and LIIb substituted 5-oxo-2-imidazolidinyl nicotinates and the formula (XII) acids, can be prepared from substituted $C_1$–$C_{12}$ alkyl 2-methylnicotinates. For convenience and clarity, the following synthesis is described using substituted methyl 2-methylnicotinates as illustrative of this class of reactions.

In accordance with the process, equivalent amounts of a substituted methyl 2-methylnicotinate, represented by formula LIII and m-chloroperbenzoic acid are admixed in the presence of a chlorinated hydrocarbon such as methylene chloride, chloroform or the like. The reaction mixture is heated to refluxing temperature, then cooled to ambient temperature and excess peracid destroyed by addition of excess 1-hexene. Thereafter the solution is washed with sodium bicarbonate solution, dried and concentrated to give the corresponding substituted methyl methylnicotinate 1-oxide of formula LIV. The formula LIV 1-oxide is then heated to about 70° to 95° C. with an excess of acetic anhydride to yield the formula LV substituted methyl 2-acetoxymethylnicotinate. A cosolvent such as pyridine or pyridine/dimethoxyethane may also be used in the reaction, but is not essential. Oxidation of the formula LV acetoxymethylnicotinate with hydrogen peroxide in acetic acid yields the methyl 2-acetoxymethylnicotinate 1-oxide represented by formula LVI. This 1-oxide is then readily converted to the formula LVII methyl 2-diacetoxymethylnicotinate by reaction with an excess of acetic anhydride at a temperature between about 70° and 95° C., with or without a cosolvent such as pyridine or pyridine/dimethoxyethane. Treatment of the formula LVII methyl diacetoxymethylnicotinate with an alkali metal alkoxide such as sodium methoxide, sodium ethoxide, potassium butoxide, or the like, in the presence of a $C_1$–$C_4$ aliphatic alcohol then yields the substituted alkyl formylnicotinate such as methyl 2-formylnicotinate of formula LVIII. Alternatively, it has also been found that the reaction of a substituted $C_1$–$C_{12}$ alkyl 2-methylnicotinate, depicted by formula LIII, with benzaldehyde at an elevated temperature, yields the formula LIX methyl 2-styrylnicotinate which, when ozonized gives the formula LVIII substituted alkyl formylnicotinate.

Additionally, it has been found that treatment of the formula LV substituted methyl 2-acetoxymethylnicotinate with an alkali metal alkoxide such as sodium methoxide, in the presence of a lower aliphatic alcohol at an elevated temperature, yields the corresponding substituted methyl 2-hydroxymethylnicotinate of formula LX. The substituted methyl 2-hydroxymethylnicotinate is then converted to the formula LVIII substituted methyl formylnictonate by oxidation with selenium dioxide or lead tetraacetate.

The above reactions are graphically illustrated in Flow Diagram II.

FLOW DIAGRAM II

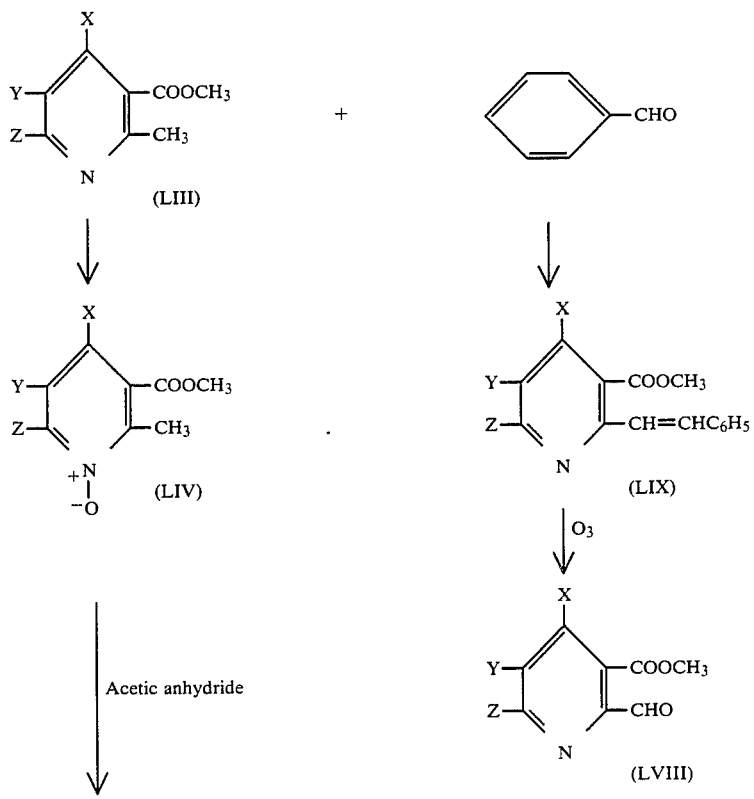

FLOW DIAGRAM II

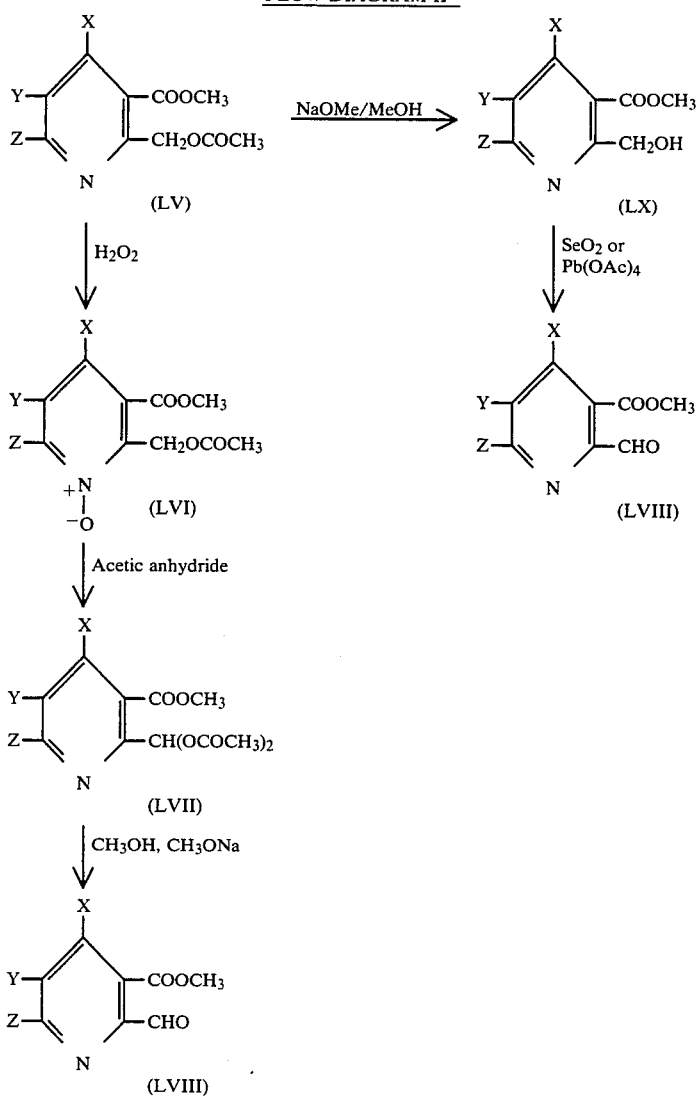

The reduction of quinolinic acid diesters with diisobutylaluminum hydride is also an effective route to alkyl 3-formylnicotinates. The synthesis of these quinolinic acid diesters is described in European Patent Application No. 81103638.3, Publication No. 0 041 623.

The aldehyde route to the preparation of the formula LIIa and LIIb substituted (5-oxo(and thioxo)-2-imidazolidinyl)nicotinates is likewise effective for the preparation of the substituted and unsubstituted (5-oxo-2-imidazolidinyl)quinoline-3-carboxylates from the substituted 2-formylquinoline-3-carboxylates.

The process for the preparation of these substituted 2-formylquinoline-3-carboxylate intermediates involves the reaction of an appropriately substituted aniline, depicted by formula LXI:

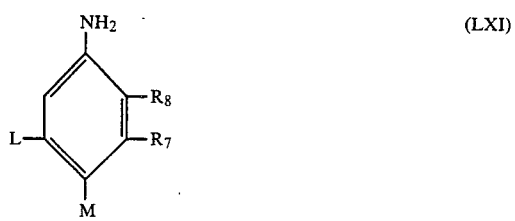

(LXI)

wherein L, M, $R_7$ and $R_8$ are as defined in reference to formula III quinolines; with approximately an equimolar amount of a keto-ester depicted by formula LXII and having the structure:

$$R'-CO-CH_2COOR''$$ (LXII)

wherein R' is $CH_3$ or COOR" and R" is $C_1$–$C_4$ alkyl. This reaction is optionally conducted in the presence of an organic sulfonic acid such as p-toluenesulfonic acid hydrate, camphorsulfonic acid, or aniline hydrochloride, in the presence of an organic solvent such as cyclohexane, toluene, benzene, xylene, monochlorobenzene, orthodichlorobenzene and mixtures thereof, or the like at a temperature from about 20° to 110° C. It is preferred to continuously remove the water which is formed during the reaction by distillation either at atmospheric or under reduced pressures of as low as 50 mm of Hg while maintaining the reaction temperature in a range of 75° to 80° C. The reaction yields the β-anilino-α,β-unsaturated ester of formula LXIII i.e.,

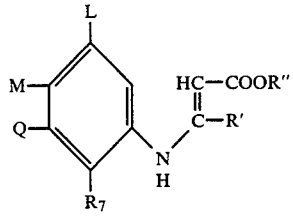
(LXIII)

wherein L, M, Q, $R_7$, R', and R" are as described above.

The thus-formed β-anilino-α,β-unsaturated ester of formula LXIII is then reacted with an approximately equimolar amount of an immonium salt having the structure:

$$Cl-CH=N^{\oplus}-(R''')_2 \cdot Cl^{\ominus},$$ (LXIV)

wherein R''' is $C_1$-$C_6$ alkyl or

(LXIVa)

wherein n is 4 or 5, and referred to respectively as formula LXIV or LXIIa. The reaction is conducted in the presence of a hydrocarbon solvent such as toluene or a chlorinated hydrocarbon solvent such as methylene chloride, dichloroethane, orthodichlorobenzene, chlorobenzene, or mixtures thereof, at a temperature between about 40° and 110° C., for a period of time sufficient to essentially complete the reaction and yield the formula LXV alkyl ester of 2-methyl-3-quinolinecarboxylic acid, if R' is $CH_3$ in the formula LXVII β-anilino-α,β-unsaturated ester or the quinoline-2,3-dicarboxylate if R' is COOR" in the formula LXVIII β-anilino-α,β-unsaturated ester.

Alternatively, the formula LXVI substituted aniline, where L, M, $R_7$ and $R_8$ are as described above, can be reacted with about an equimolar amount of a formula LXVI acetylene dicarboxylate having the structure:

$$R''OOC-C\equiv C-COOR'',$$

where R" is $C_1$-$C_4$ alkyl. This reaction is generally carried out in the presence of a solvent such as dichloroethane or a $C_1$-$C_4$ alcohol such as methanol, at a temperature between 0° and 100° C. to yield a β-anilino-α,β-unsaturated ester as formula LXIII. The β-anilino-α,β-unsaturated ester of formula LXIII is then reacted with an immonium salt depicted by formula LXIV having the structure:

$$Cl-CH=N^{\oplus}-(R''')_2 \cdot Cl^{\ominus}$$

wherein R''' is $C_1$-$C_6$ alkyl or LXIVa having the structure:

where n is 4 or 5. While the anion in formulas LXIV or LXIVa is shown as $Cl^{\ominus}$, it should be recognized that when $POCl_3$ is used to prepare the Vilsmeier reagent, the anion is $PO_2Cl_2^{\ominus}$. This reaction is generally conducted in the presence of a solvent such as methylene chloride, dichloroethane, monochlorobenzene, orthodichlorobenzene, or toluene at a temperature between 40° and 110° C. for a period of time sufficient to complete the reaction and yield the quinoline-2,3-dicarboxylate shown as formula LXVa having the structure:

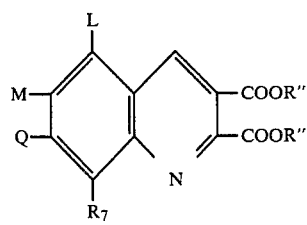
(LXVa)

wherein L, M, Q, $R_7$ and R" are as described above.

The immonium salt formula LXIV or LXIVa utilized in the above cyclization reactions may, hereafter, be referred to as the Vilsmeier reagent. This reagent may be generated from a (N,N-dialkyl or N-alkyl,N-phenyl)-formamide reaction with $POCl_3$, $COCl_2$, $ClCO-COCl$ or $SOCl_2$ in a hydrocarbon or chlorinated hydrocarbon solvent.

Conversion of the 2-methyl-3-quinolinecarboxylate shown as formula LXV in which R'=$CH_3$ to the corresponding aldehyde of formula LXVII can be achieved in a manner similar to that described above for the conversion of the substituted 2-methylnicotinate of formula LIII to the corresponding 2-formylnicotinate of LVIII.

Conversion of the quinoline-2,3-dicarboxylate, shown as formulas LXV and LXVa, to the corresponding aldehyde shown as formula LXVII having the structure:

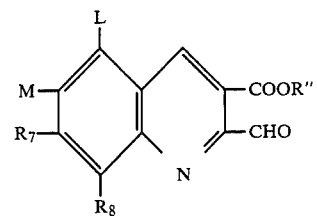
(LXVII)

where L, M, $R_7$, $R_8$ and R" are as defined above, can be achieved by reaction of the formula LXV quinoline-2,3-dicarboxylate with diisobutylaluminum hydride. The reaction is preferably conducted in the presence of a non-protic solvent such as tetrahydrofuran under a blanket of inert gas.

These reactions are graphically illustrated in Flow Diagram III below.

FLOW DIAGRAM III

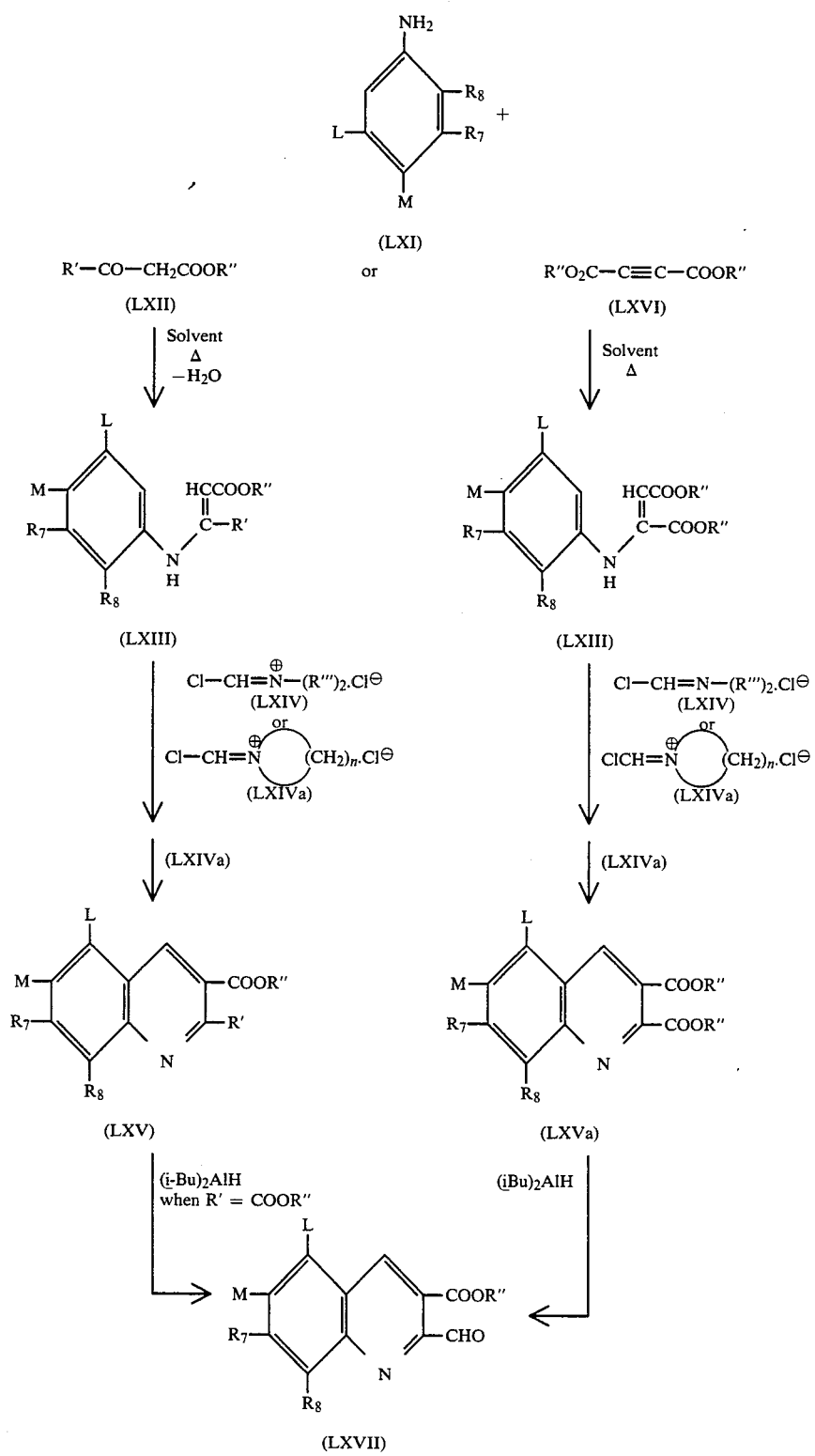

The 2-(2-imidazolidinyl)thieno- and furo[3,2-b]pyridine-6-carboxylates; 2-(2-imidazolidinyl)-2,3-dihydrothieno- and furo[3,2-b]pyridine-6-carboxylates; 2-(2-imidazolidinyl)thieno- and furo[2,3-b]pyridine-5-carboxylates and 2-(2-imidazolidinyl)-2,3-dihydrothieno- and furo[2,3-b]pyridine-5-carboxylates, useful as intermediates in the preparation of the formula (I) compounds of this invention can be obtained, by reduction of the corresponding (2-imidazolin-2-yl)thieno- and furo[2,3-b] and [3,2-b]pyridines with sodium cyanoborohydride. These 2-(2-imidazoline-2-yl)thieno- and furo[2,3-b] and [3,2-b]pyridine intermediates, necessary for the preparation of the formula V, VI, VII and VIII, thieno- and furopyridines, of the present invention are described in the copending application for U.S. Letters patent of Marinus Los, David William Ladner and Barrington Cross, Ser. No. 500,219, filed June 2, 1983, and incorporated herein by reference thereto.

The 2-(2-imidazolin-2-yl)thieno and furo[2,3-b] and [3,2-b]pyridine intermediates, used in the synthesis of the 2-(2-imidazolidinyl)thieno- and furo[2,3-b] and [3,2-b]pyridines starting materials for the compounds of the present invention are depicted by formulas Va, VIa, VIIa and VIIIa, illustrated below.

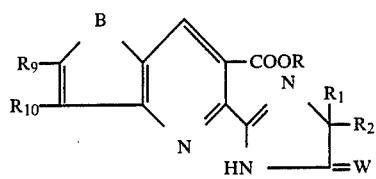
(Va)

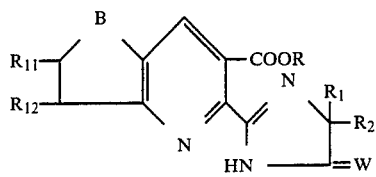
(VIa)

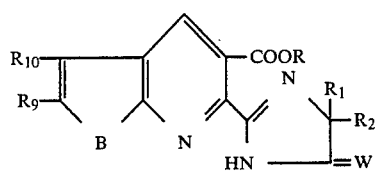
(VIIa)

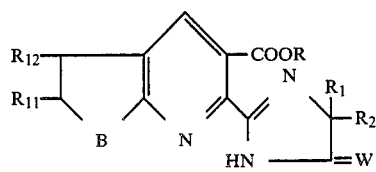
(VIIIa)

wherein R is hydrogen or $C_1$-$C_4$ alkyl and $R_1$, $R_2$, $R_9$, $R_{10}$, $R_{11}$, $R_{12}$, B and W are as described above in reference to compounds of formula V, VI, VII and VIII.

While for convenience, the imidazolinone and imidazolinethione intermediates referred to throughout are illustrated by single structures, it should be recognized that the imidazolinyl function in these compounds may exist in either tautomeric form, i.e.:

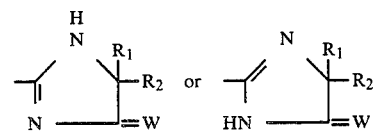

The formula Va, VIa, VIIa and VIIIa, intermediates for the compounds of the present invention may be prepared from the appropriately substituted thieno and furo[2,3-b] and [3,2-b]pyridinecarboxylic acids and esters of formulas LXXI and LXXIa illustrated below.

Since $R_9$ and $R_{10}$ represent substituents selected from hydrogen, halogen, $C_1$-$C_4$ alkyl and phenyl, and $R_{11}$ and $R_{12}$ represent hydrogen, $C_1$-$C_4$ alkyl and phenyl; for the purposes of the following discussion, which relates to the preparation of the formula Va, VIa, VIIa and VIIIa, 2-(2-imidazolin-2-yl)thieno and furo[2,3-b] and [3,2-b]pyridines, compound structures involved in the synthesis under discussion will be illustrated with $R_9$ and $R_{10}$.

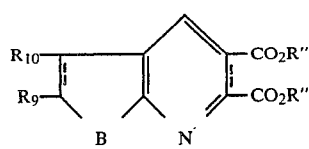
(LXXI)

and

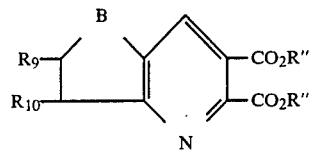
(LXXIa)

wherein $R_9$, $R_{10}$ and B are as previously described and R″ is methyl or ethyl.

Methods suitable for preparing formula Va, VIa, VIIa and VIIIa unsaturated compounds wherein -- is a double bond from the formula (LXXI) and (LXXIa) pyridinecarboxylic acid esters are illustrated in Flow Diagram IV below.

Thus formula (LXXI) and (LXXIa) diesters may be hydrolyzed to the corresponding thieno- and furo-2,3-pyridinedicarboxylic acids of formula (LXXII) and (LXXIIa) by reaction thereof with a strong base such as potassium hydroxide or sodium hydroxide. Acid anhydrides of formula (LXXIII) and (LXXIIIa) may then be prepared by treatment of the formula (LXXII) and (LXXIIa) pyridinedicarboxylic acids with, for example, acetic anhydride. Reaction of formula (LXXIII) and (LXXXIIIa) anhydrides with an appropriately substituted aminocarboxamide or aminothiocarboxamide depicted by formula (IX) yields carbamoyl nicotinic acids of formula (LXXIV) and (LXXIVa). Treatment of the thus-formed formula (LXXIV) and (LXXIVa) carbamoyl nicotinic acids with about 2 to 10 molar equivalents of aqueous or aqueous alcoholic sodium or potassium hydroxide, preferably under a blanket of inert gas such as nitrogen, cooling and acidifying to pH 2 to 4 with a strong mineral acid such as hydrochloric acid or sulfuric acid gives herbicidally effective 6-(4,4-disubstituted-5-oxo-(or thiono)-2-imidazolin-2-yl)thieno- and furo[2,3-b]pyridine-5-carboxylic acids, and 5-(4,4-disubstituted-5-oxo-(or thiono)-2-imidazolin-2-yl)thieno- and furo[3,2-b]pyridine-6-carboxylic acids encompassed by formulas (Va) and (VIIa).

Formula (Va) and (VIIa) 5-(2-imidazolin-2-yl)thieno- and furopyridine esters, wherein R represents a substituent other than hydrogen or a salt-forming cation, and $R_1$, $R_2$, $R_9$, $R_{10}$ and B are as described above can be prepared by reacting a novel thieno- or furoimidazopyrrolopyridinedione, represented by formulas (LXXV) and (LXXVa), hereinbelow, in Flow Diagram (V), with an appropriate alcohol and corresponding alkali metal alkoxide at a temperature ranging between about 20° and about 50° C.

Formula (LXXV) and (LXXVa) thieno- and furoimidazopyrrolopyridinediones may conveniently be prepared from formula (VIIa) and (Va) acids, where R is H by treatment with one equivalent of dicyclohexylcarbodiimide in an inert solvent such as methylene chloride as illustrated in Flow Diagram (V) below.
FLOW DIAGRAM (IV)
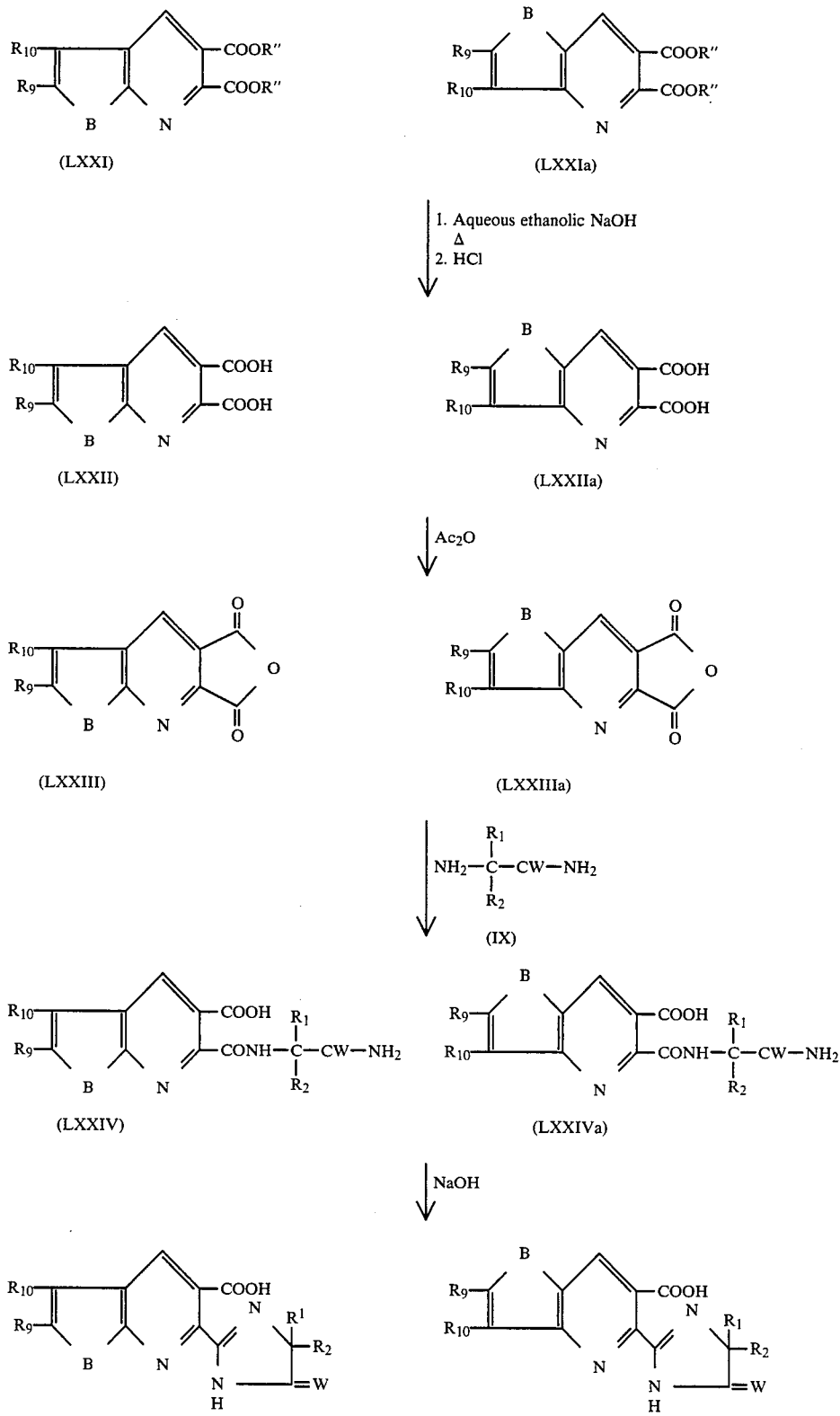

FLOW DIAGRAM (V)

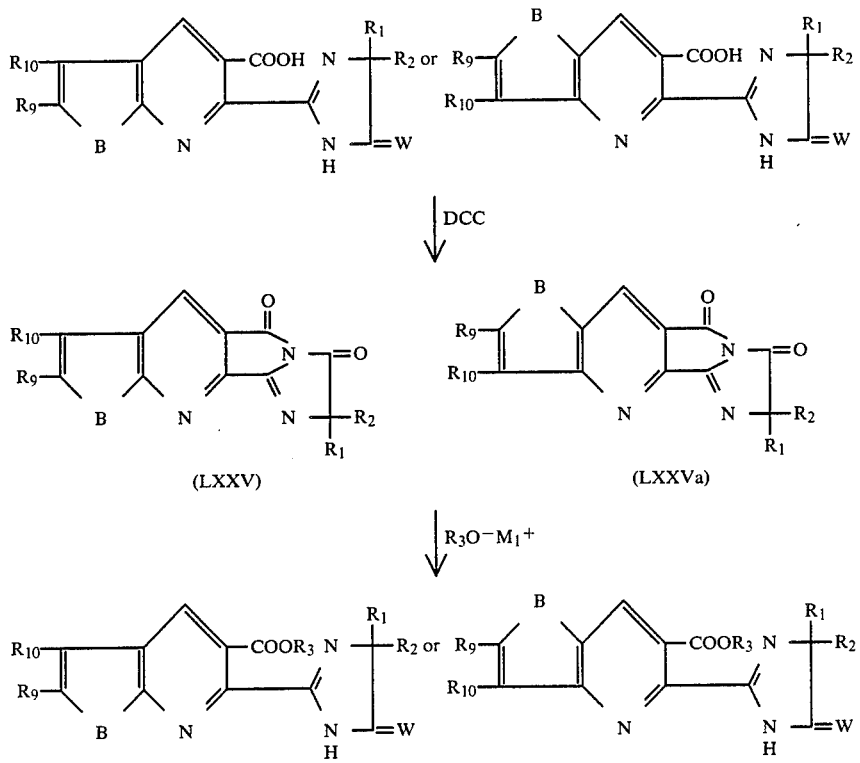

where $M_1$ is an alkali metal, and X, Y, Z, $R_1$, $R_2$ are as above defined and $R_3$ is $C_1$–$C_4$ alkyl.

Many formula (LXXI) thieno[2,3-b]pyridinedicarboxylic acids and (LXXIa) thieno[3,2-b]pyridinedicarboxylic acids may conveniently be prepared by reacting the appropriately substituted 2 or 3-aminothiophene of formula (LXXXIV) or (LXXXIVa) with a $C_1$–$C_4$ alkyl ester of acetylenedicarboxylic acid of formula (IX) as described by Bleckert et al., Chem. Ber. 1978, 106, 368. The thus-formed β-aminothieno-α,β-unsaturated ester of formula (LXXXV) or (LXXXVa) is then reacted with an immonium salt depicted by the formula Cl—CH=N⊕—(R''')₂Cl⊖ wherein R''' is $C_1$–$C_6$ alkyl or

where n' is 4 or 5, in the presence of a low boiling chlorinated hydrocarbon solvent such as methylene chloride or dichloroethane at a temperature between about 40° and 90° C., for a period of time sufficient to essentially complete the reaction and yield the formula (LXXI) [2,3-b]thieno- or (LXXIa) [3,2-b]thieno-2,3-pyridinedicarboxylic acid as the dialkyl ester as illustrated in Flow Diagram (VI) below.

The furo[3,2-b]pyridinedicarboxylic acids may be prepared by reacting 3-amino-2-formylfuran of formula (LXXVI) prepared by the method of S. Gronowitz et al., Acta Chemica Scand B29 224(1975) with ethyl oxalacetate to give the furopyridine compounds directly, as illustrated in Flow Diagram (VII) below while the furo[2,3-b]pyridine compounds where $R_9$ and $R_{10}$ are H are obtained by bromination of the reaction product (LXXVII) of acetoacetamide with the diethyl ester of ethoxymethyleneoxalacetic acid followed by treatment with sodium borohydride and para-toluene sulfonic acid in refluxing xylene as illustrated in Flow Diagram (VIII) below.

FLOW DIAGRAM (VI)

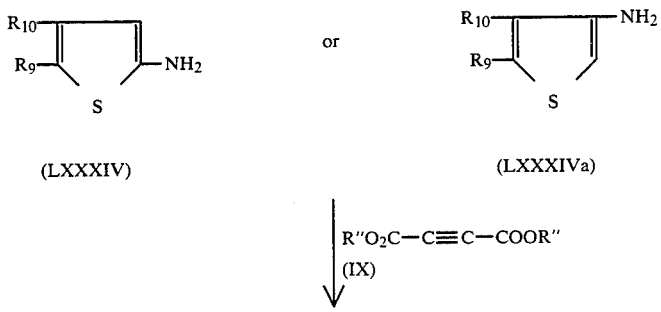

FLOW DIAGRAM (VI)

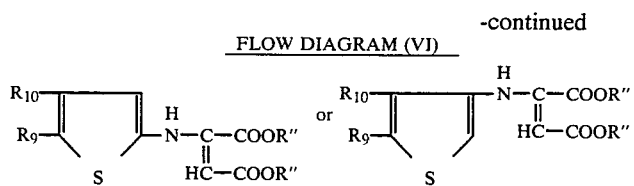

(LXXXV)          (LXXXVa)

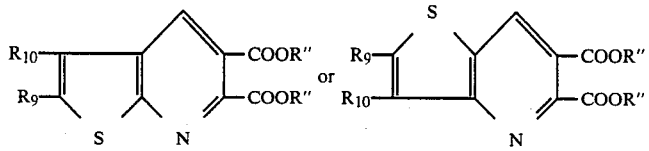

(LXXI)          (LXXIa)

FLOW DIAGRAM (VII)

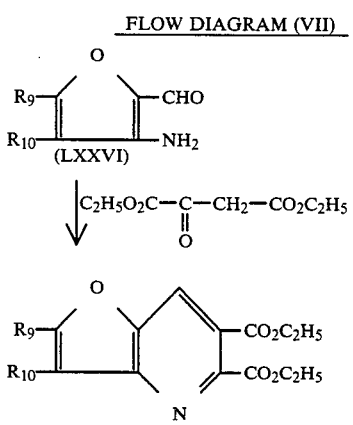

(LXXVI)

FLOW DIAGRAM (VIII)

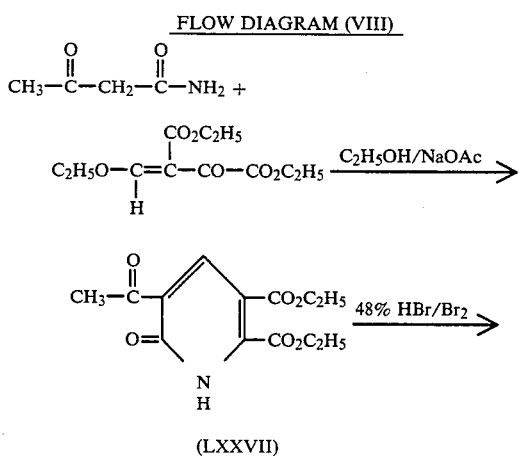

(LXXVII)

-continued
FLOW DIAGRAM (VIII)

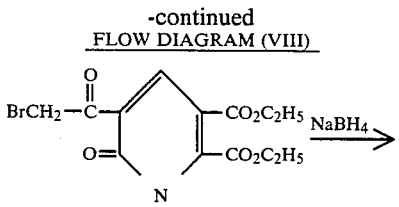

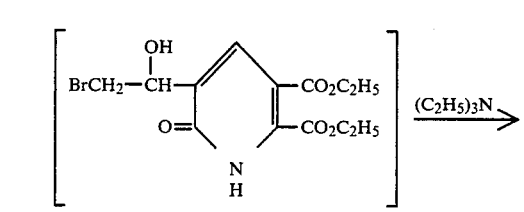

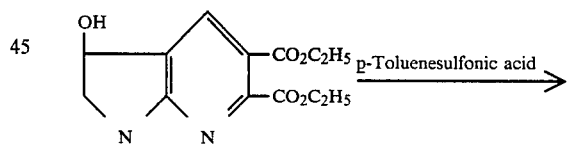

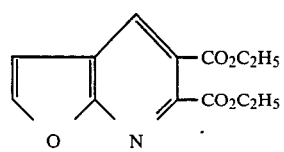

Substituents represented by $R_9$ and $R_{10}$ in formula (Va), (VIIa), (LXXV) and (LXXVa) compounds of the present invention may be prepared either by using the appropriately substituted starting material for the preparation of formula (LXXI) and (LXXIa) thieno- and furopyridine-5,6-dicarboxylic acid esters or by electrophilic substitution (halogenation, nitration, sulfonation, etc.) directly upon formula (LXXI) or (LXXIa) diesters or Formula (Va) or (VIIa) final products, wherein at least one of Y or Z is hydrogen. These substituted formula (LXXI), (LXXIa), (Va) and (VIIa) compounds then may be used as starting materials for additional $R_9$ and $R_{10}$ substitution by displacement, reduction, oxidation, etc. Representative substituted (LXXI) and (LXXIa) compounds which may be prepared by these procedures are illustrated below.

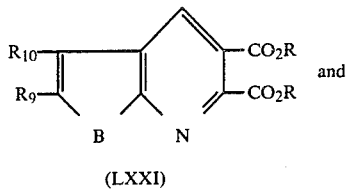

(LXXI)

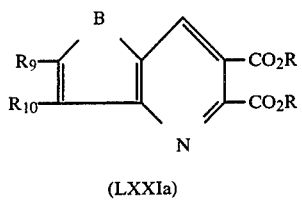

(LXXIa)

| B | $R_9$ | $R_{10}$ | R |
|---|---|---|---|
| S | H | H | $CH_3$ |
| S | H | Br | $CH_3$ |
| S | $CH_3$ | H | $CH_3$ |
| S | H | Cl | $CH_3$ |
| S | Cl | Cl | $CH_3$ |
| S | H | I | $CH_3$ |
| S | H | $NO_2$ | $CH_3$ |
| S | Br | Br | $CH_3$ |
| S | $CH_3$ | Cl | $CH_3$ |
| S | H | $CH_3$ | $CH_3$ |
| S | Cl | H | $CH_3$ |
| S | $CH_3$ | $CH_3$ | $CH_3$ |
| S | H | CN | $CH_3$ |
| S | H | $OCH_3$ | $CH_3$ |
| S | H | $N(CH_3)_2$ | $CH_3$ |
| S | H | $SCH_3$ | $CH_3$ |
| S | H | $OCF_2H$ | $CH_3$ |
| O | H | H | $C_2H_5$ |
| O | H | Br | $CH_3$ |
| O | H | Cl | $CH_3$ |
| O | $CH_3$ | H | $CH_3$ |
| O | $CH_3$ | H | $C_2H_5$ |
| O | H | $CH_3$ | $CH_3$ |
| O | $C_2H_5$ | H | $CH_3$ |
| O | H | $C_2H_5$ | $CH_3$ |
| O | $CH_3$ | $CH_3$ | $CH_3$ |
| S | | $-(CH_2)_3-$ | $CH_3$ |
| S | | $-(CH_2)_4-$ | $CH_3$ |
| S | | $-(CH)_4-$ | $CH_3$ |
| S | $C_6H_5$ | H | $CH_3$ |
| O | $C_6H_5$ | H | $CH_3$ |
| S | H | $SO_2N(CH_3)_2$ | $CH_3$ |
| S | H | $OC_6H_5$ | $CH_3$ |
| O | H | $OC_6H_5$ | $CH_3$ |
| O | $CF_3$ | H | $CH_3$ |

Additionally, novel herbicidal 2,3-dihydrothieno[2,3-b] and [3,2-b]pyridine compounds may be obtained by starting the sequence in Flow Diagram (VI) above with a dihydrothiophenimine hydrochloride. Novel herbicidal 2,3-dihydro furo[2,3-b] and [3,2-b]pyridines may be prepared by catalytic reduction of the formula (Va) or (VIIa) (2-imidazolin-2-yl) product, or (LXXI) and (LXXIa) furo[2,3-b] and [3,2-b]pyridine-5,6-diesters as for example with hydrogen and palladium on carbon, provided that $R_9$ and $R_{10}$ are substituents which are not reduced by such a procedure. This then provides novel 2,3-dihydro herbicidal compounds illustrated below.

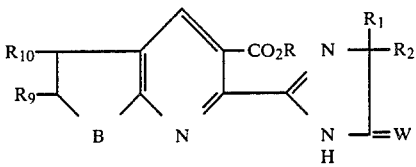

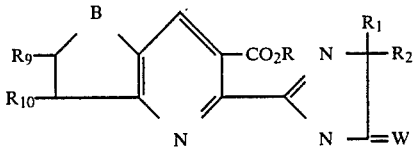

wherein $R_9$, $R_{10}$, B, W, $R_1$, $R_2$ and $R_B$ are as described for (Va) and (VIIA).

The formula I dihydroimidazopyrrolopyridines and derivatives of the present invention are highly effective preemergence and postemergence herbicidal agents, useful for the control of a wide variety of undesirable monocotyledonous and dicotyledonous plant species. Surprisingly, it has also been found that these formula I compounds are very active against a wide variety of weed species but well tolerated by a number of crops including: graminaceous crops such as sunflower, corn, rice, turf, and wheat; leguminous crops such as soybeans and other crops including cotton. While herbicidal selectivity of the formula I compounds of this invention may vary with compound structure from crop to crop, the presence of the dihydroimidazopyrrolopyridine function, which is unique to all of the formula I compounds of this invention, appears to impart significant herbicidal selectivity to said compounds. This selectivity thus permits application of the active compounds to newly planted fields or to maturing crops for control of undesirable grasses and broadleaf weeds in the presence of said crops.

It is also surprising to find that the compounds of this invention, frequently exhibit plant growth regulating activity when employed at non-herbicidal rates of application.

In practice, the formula I dihydroimidazopyrrolopyridines and derivatives thereof may be applied to the foliage of undesirable monocotyledonous or dicotyledonous plants or to soil containing seeds or other propagating organs of said plants such as tubers, rhizomes or stolons, at ranges generally between about 0.032 and 4.0 kg/ha, and preferably between about 0.063 and 2.0 kg/ha, although rates as high as 8.0 kg/ha may be used if desired.

Effective plant growth regulating activity such as dwarfing, antilodging, increased branching, increased tillering and the like, is generally obtained when the above-said formula I compounds are applied to crops at rates below herbicidal rates. Obviously, this rate will vary from compound to compound.

The formula I compounds of the present invention may be applied to the foliage of plants or to soil containing seeds or other propagating organs thereof, in the form of a liquid spray, as a ULV concentrate or as a solid formulation.

Formula I compounds may also be prepared as wettable powders, flowable concentrates, emulsifiable concentrates, granular formulations or the like.

A typical emulsifiable concentrate can be prepared by dissolving about 5 to 25% by weight of the active ingredient in about 65 to 90% by weight of N-methylpyrrolidone, isophorone, butyl cellosolve, methylacetate or the like and dispersing therein about 5 to 10% by weight of a nonionic surfactant such as an alkylphenoxy polyethoxy alcohol. This concentrate is dispersed in water for application as a liquid spray or it may be applied directly as an ultra low volume concentrate in the form of discrete droplets having a mass median diameter between about 17 and 150 microns particle size.

Wettable powders can be prepared by grinding together about 20 to 45% by weight of a finely divided carrier such as kaolin, bentonite, diatomaceous earth, attapulgite, or the like, 45 to 80% by weight of the active compound, 2 to 5% by weight of a dispersing agent such as sodium lignosulfonate, and 2 to 5% by weight of a nonionic surfactant, such as octylphenoxy polyethoxy ethanol, nonylphenoxy polyethoxy ethanol or the like.

A typical flowable liquid can be prepared by admixing about 40% by weight of the active ingredient with about 2% by weight of a gelling agent such as bentonite, 3% by weight of a dispersing agent such as sodium lignosulfonate, 1% by weight of polyethylene glycol and 54% by weight of water.

When the compounds of the invention are to be used as herbicides where soil treatments are involved, the compounds may be prepared and applied as granular products. Preparation of the granular product can be achieved by dissolving the active compound in a solvent such as methylene chloride, N-methylpyrrolidone or the like and spraying the thus-prepared solution on a granular carrier such as corncob grits, sand, attapulgite, kaolin or the like.

The granular product thus-prepared generally comprises about 3 to 20% by weight of the active ingredient and about 97 to 80% by weight of the granular carrier.

In order to facilitate a further understanding of the invention, the following examples are presented primarily for the purpose of illustrating certain more specific details thereof. The invention is not to be deemed limited thereby except as defined in the claims. Unless otherwise noted, all parts are by weight.

EXAMPLE 1

Preparation of 7-ethyl-1,9bα(and β)-dihydro-3α-isopropyl-3-methyl-5H-imidazo[1',2':1,2]pyrrolo[3,4-b]pyridine-2(3H),5-dione

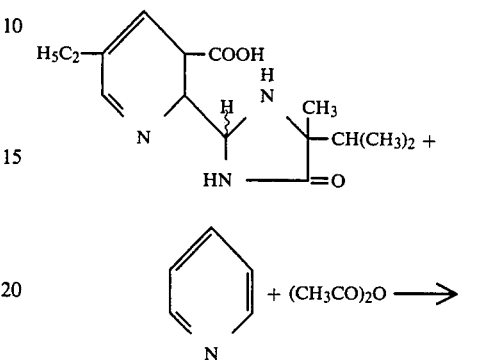

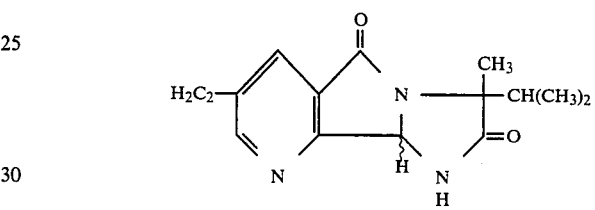

A suspension of 1 g of cis- and trans-5-ethyl-2-(4-isopropyl-4-methyl-5-oxo-2-imidazolidinyl)-nicotinic acid and 0.4 mL pyridine and 0.5 mL acetic anhydride in 10 mL acetonitrile is warmed to about 50° C. until a clear solution is obtained. Upon cooling the solution to room temperature, a solid crystallizes. The solid is collected by filtration and recrystallized from ethyl acetate to give analytically pure 7-ethyl-1,9b α(and β)-dihydro-3α-isopropyl-3-methyl-5H-imidazo[1',2':1,2]pyrrolo[3,4-b]pyridine-2(3H),5-dione, mp 170°–177° C.

EXAMPLE 2

Preparation of 7-dimethyl-1,9bβ-dihydro-3α-isopropyl-3,5H-imidazo[1',2':1,2]pyrrolo[3,4-b]pyridine-2(3H),5-dione

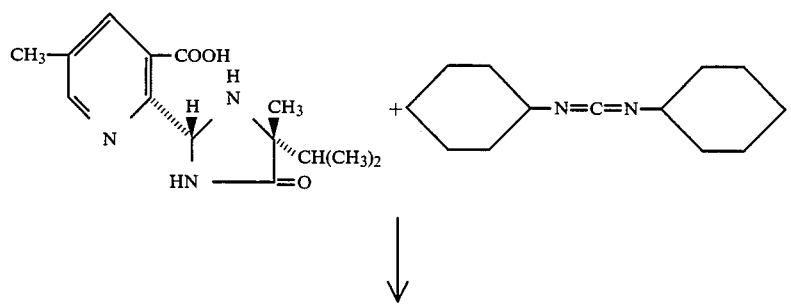

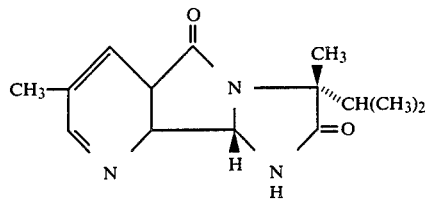

A mixture containing 1.08 g of cis-2-(4-isopropy-4-methyl-5-oxo-2-imidazolidinyl)-5-methyl-nicotinic acid and 0.89 g of N,N'-dicyclohexylcarbodiimide in 25 mL methylene chloride is stirred at room temperature for 18 hours. The mixture is filtered and concentrated in vacuo. The crystalline residue is recrystallized from methylene chloride to give analytically pure 7-dimethyl-1,9bβ-dihydro-3α-isopropyl-3,5H-imidazo[1',2':1,2-]pyrrolo[3,4-b]pyridine-2(3H),5-dione, mp 191°–193° C.

EXAMPLE 3

Preparation of 1,9bα(and β)-dihydro-3α-isopropyl-3-methyl-5H-imidazo[1',2':1,2]pyrrolo[3,4-b]pyridine-2-(3H),5-dione

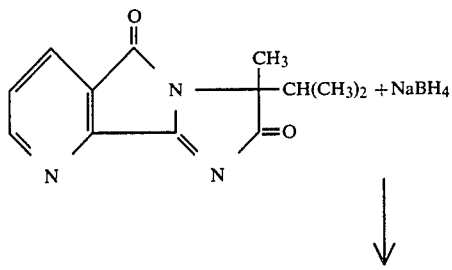

-continued

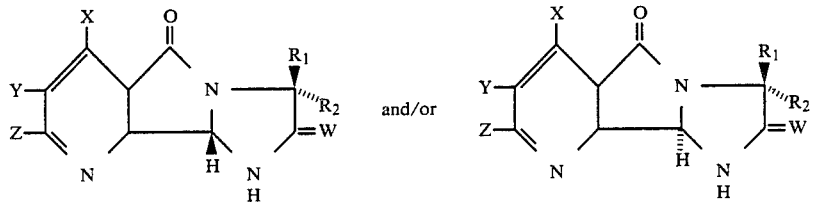

To a suspension of 1.7 g sodium borohydride in 120 mL absolute ethanol cooled to 0° C. is added dropwise a solution of 10.8 g 3-isopropyl-3-methyl-5H-imidazo[1',2':1,2]pyrrolo[3,4-b]pyridine-2(3H),5-dione in 120 mL dry tetrahydrofuran, maintaining the temperature between 0° and 5° C. The mixture is stirred at room temperature for two hours and added to ice water. The aqueous mixture is acidified to pH 3 with concentrated sulfuric acid and extracted with methylene chloride. Extracts are dried and concentrated in vacuo to give a solid. The solid is washed with anhydrous ether and air dried to give 1,9bα(and β)-dihydro-3α-isopropyl-3-methyl-5H-imidazo[1',2':1,2]pyrrolo[3,4-b]pyridine-2(3H),5-dione, mp 170° C. (dec).

EXAMPLE 4

Preparation of formula (I) dihydroimidazopyrrolopyridines or derivatives thereof Following one of the procedures described in Examples 1, 2 or 3, the compounds of formula (I), reported in Table I below, were prepared.

TABLE I

Formula (I) compounds of the invention having the cis and/or trans structure illustrated below

| (3RS) | (3R) | $R_1$ | $R_2$ | X | Y | Z | W | cis | trans | mp °C. |
|---|---|---|---|---|---|---|---|---|---|---|
| √ | | $CH_3$ | $C_2H_5$ | H | H | H | O | 36 | 64 | 192.0–107.0 |
| √ | | $CH_3$ | $CH(CH_3)_2$ | H | H | H | O | 25 | 75 | 170.0 (dec) |
| √ | | $CH_3$ | $CH(CH_3)_2$ | H | $CH_3$ | H | O | √ | | 191.0–193.0 |
| | √ | $CH_3$ | $CH(CH_3)_2$ | H | H | H | O | √ | | 200.0–205.0 |
| √ | | $CH_3$ | $CH(CH_3)_2$ | H | H | H | O | √ | | 206.0–217.5 |
| √ | | $CH_3$ | $CH(CH_3)_2$ | H | H | $CH_3$ | O | √ | | 202.0–217.0 |
| √ | | $CH_3$ | $CH(CH_3)_2$ | H | H | $CH_2$=CH—$CH_2$O | O | √ | | 185.0–187.0 |
| √ | | $CH_3$ | $CH(CH_3)_2$ | H | H | H | O | | √ | 231.0–234.0 |
| √ | | $CH_3$ | $CH(CH_3)_2$ | H | $C_2H_5$ | H | O | 50 | 50 | 170.0–177.0 |
| √ | | $CH_3$ | $CH(CH_3)_2$ | H | H | $CH_3O$ | O | √ | | 215.0–219.0 |
| √ | | $CH_3$ | $CH(CH_3)_2$ | H | H | Cl | O | √ | | 208.0–222.0 |
| √ | | $CH_3$ | $CH(CH_3)_2$ | H | $C_2H_5$ | H | O | √ | | 200.0–203.0 |
| √ | | $CH_3$ | $CH(CH_3)_2$ | H | $C_2H_5$ | H | O | | √ | 220.0–222.0 |
| √ | | $CH_3$ | $CH(CH_3)_2$ | H | H | H | S | √ | | 144.0–146.0 |
| √ | | $CH_3$ | $CH(CH_3)_2$ | H | $CH_3$ | H | S | √ | | 225.0–230.0 |

TABLE I-continued

Formula (I) compounds of the invention having the cis and/or trans structure illustrated below

| (3RS) | (3R) | R₁ | R₂ | X | Y | Z | W | cis | trans | mp °C. |
|---|---|---|---|---|---|---|---|---|---|---|
| √ | | CH₃ | CH(CH₃)₂ | H | CH₃ | H | S | | √ | 243.0–249.0 |
| √ | | CH₃ | CH(CH₃)₂ | H | —CH=CH—CH=CH— | | O | | √ | 229.0–251.0 |
| √ | | CH₃ | CH(CH₃)₂ | H | CH₃O— | H | O | √ | | 202.0–204.0 |
| √ | | CH₃ | CH(CH₃)₂ | H | Cl | H | O | √ | | 209.0–211.0 |
| √ | | CH₃ | CH(CH₃)₂ | H | H | H | S | | √ | 252.0–256.0 |
| √ | | CH₃ | CH(CH₃)₂ | H | CH₃ | H | O | 33 | 66 | 170.0–183.0 |
| | √ | CH₃ | CH(CH₃)₂ | H | CH₃ | H | O | 26 | 74 | 160.0–163.0 |
| √ | | CH₃ | CH(CH₃)₂ | H | OCH₂CH=CH₂ | H | O | √ | | 189.0–191.0 |
| √ | | CH₃ | CH(CH₃)₂ | H | CH₃ | H | O | | √ | 208.0–209.0 |
| | √ | CH₃ | CH(CH₃)₂ | H | CH₃ | H | O | | √ | 194.5–195.5 |
| | √ | CH₃ | CH(CH₃)₂ | H | CH₃ | H | S | √ | | 227.0–229.0 |
| √ | | CH₃ | CH(CH₃)₂ | H | H | —⟨C₆H₄⟩—CH₃ | O | √ | | 241.0–243.0 |
| √ | | CH₃ | CH(CH₃)₂ | H | H | —⟨C₆H₄⟩—CH₃ | O | | √ | 271.0–272.0 |
| √ | | CH₃ | CH(CH₃)₂ | H | H | N(CH₃)₂ | O | √ | | 250.0–253.0 |

EXAMPLE 4-A

Preparation of 3-isopropyl-3-methyl-5H-imidazo[1',2':1,2]pyrrolo[3,4-b]pyridine-2(3H),5-dione

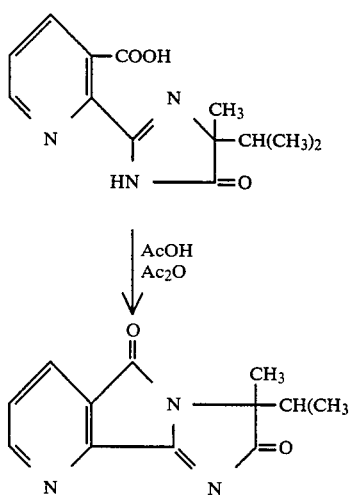

A stirred mixture of 123.2 g acid in 300 mL acetic acid and 89 mL acetic anhydride is heated at reflux for four hours. The mixture is concentrated in vacuo and the residue dissolved in toluene and again concentrated. The residue is slurried in hexane, filtered and washed several times with hexane to give a 90% of product, mp 105°–112° C. NMR and Gc analysis indicztes this material to consist of 80–87% of the desired 2,5-dione and the balance of the material being the corresponding 3,5-dione.

EXAMPLE 4-B

Preparation of 1,9b-dihydro-3α-isopropyl-3-methyl-9bα-propoxy-5H-imidazo[1',2':1,2]pyrrolo[3,4-b]pyridine-2-(3H),5-dione

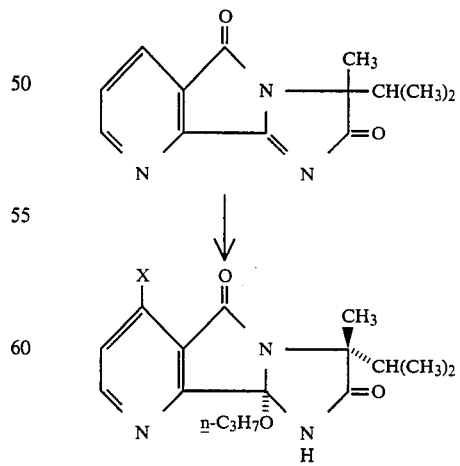

The solution containing 54 g dione in 200 mL n-propanol is heated at reflux for one hour. The solution is slowly cooled to 0° C. and after one hour, the white crystals removed by filtration. The solids are washed with hexane and dried to give 41.6 of the 9bα-propoxy derivative mp 129°–132° C. This material can be recrystallized from ether-hexane to give analytically pure material mp 135°–137.5° C. This product can also be obtained by running the reaction at room temperature.

Using essentially the same conditions but utilizing the appropriate nucliophile and the appropriate 2,5-dione, the following dihydro derivatives are prepared.

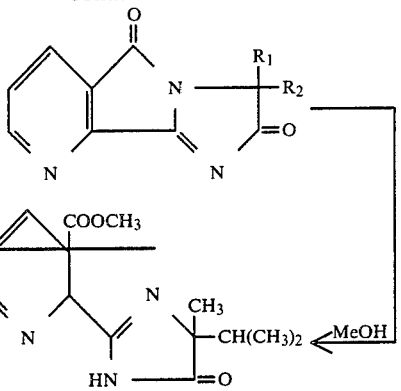

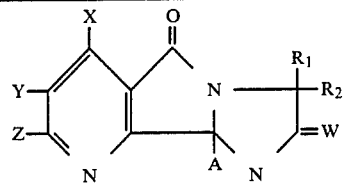

| $R_1$ | $R_2$ | W | A | X | Y | Z | mp °C. | |
|---|---|---|---|---|---|---|---|---|
| $CH_3$ | $C_2H_5$ | O | $OCH_2C_6H_5$ | H | H | H | 135–139 | cis |
| $CH_3$ | $C_2H_5$ | O | $OCH_2C_6H_5$ | H | H | H | 135–145 | trans |
| $CH_3$ | $C_2H_5$ | O | $OCH_2CH=CH_2$ | H | H | H | 145–148 | trans |
| $CH_3$ | $CH(CH_3)_2$ | O | $OCH_3$ | H | H | H | 130–139 | trans |
| $CH_3$ | $CH(CH_3)_2$ | O | $OC_3H_6$—n | H | H | H | 135–137.5 | trans |
| $CH_3$ | $CH(CH_3)_2$ | O | $NHCH_2C≡CH$ | H | H | H | 168–169 | trans |
| $CH_3$ | $CH(CH_3)_2$ | O | $OCH_2-\phantom{}-N(CH_3)_2$ | H | H | H | 163–164.5 | trans |
| $CH_3$ | $CH(CH_3)_2$ | O | $NH_2$ | H | H | H | 165–167 | trans |
| $CH_3$ | $CH(CH_3)_2$ | O | $OCH_2C_6H_5$ | H | H | H | 133–135 | trans |
| $CH_3$ | $CH(CH_3)_2$ | O | $C_2H_5$ | H | H | H | 142–144 | trans |
| $CH_3$ | $CH(CH_3)_2$ | O | $OCH_3$ | H | $—(CH_2)_5—$ | | 173–175 | trans |
| $CH_3$ | $CH(CH_3)_2$ | S | $OCH_3$ | H | H | H | 161–163 | trans |
| $CH_3$ | $CH(CH_3)_2$ | O | $SCH_3$ | H | H | H | 147–149 | |
| $CH_3$ | $CH(CH_3)_2$ | S | $OCH_3$ | H | $—CH=CH—CH=CH—$ | | 232–233 | |
| $CH_3$ | $CH(CH_3)_2$ | S | OH | H | H | H | 162–165 | |

EXAMPLE 5

Preparation of methyl 2-(4-isopropyl-4-methyl-5-oxo-2-imidazolin-yl)nicotinate

This method involves the formation of trycyclic compounds, without isolation, directly forming the nicotinic acid esters:

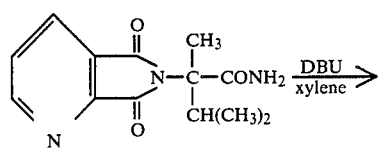

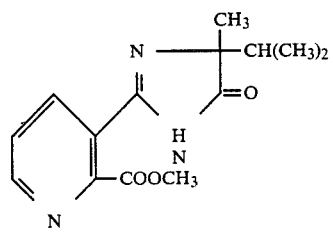

A mixture of 25 g amide and 1 mL 1,5-diazabicyclo-[5.4.0]undec-5-ene(DBU) in 500 mL xylene is heated under reflux for one hour under a Dean-Stark water separator. The mixture is cooled somewhat, the water separator removed, 100 mL anhydrous methanol added and the mixture heated under reflux for one hour. The solvents are then removed in vacuo and the product isolated by chromatography as to give 13.65 g product mp 120°–122° C. Other esters as described in Example 28 in the same manner using the appropriately substituted amide starting material. This procedure is also described in European Patent Application No. 81103638.3, publication No. 0.041,623.

EXAMPLE 6

Preparation of methyl 2-(4-isopropyl-4-methyl-5-oxo-2-imidazolin-2-yl)nicotinate

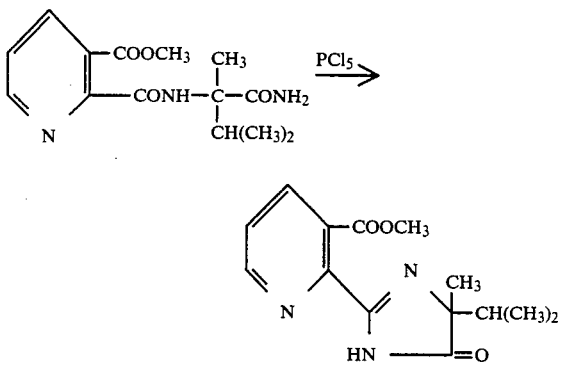

Method A

A mixture of 13.65 g of the nicotinate and 9.69 g phosphorus pentachloride in 110 mL dry toluene is heated with stirring to 80° C. After one and one-half hours, the thick mixture is cooled, filtered and the solid washed with ether and dried. This is the hydrochloride salt of the desired product.

This salt is dissolved in 60 mL water; neutralized with sodium bicarbonate, the resulting precipitate removed by filtration, washed with water and air-dried to give the product.

Method B

A mixture of 5.0 g nicotinate and 7.1 g phosphorus pentachloride in 40 mL phosphorus oxychloride is stirred at room temperature overnight. The phosphorous oxychloride is removed in vacuo, the residue suspended in 40 mL toluene and again concentrated. This is repeated. Water (40 mL) is added to the residue and the mixture heated to reflux and held there for one hour. After cooling, the mixture is extracted with methylene chloride, the extract dried and concentrated to give 1.05 g of the desired product. The pH of the aqueous phase from the methylene chloride extraction is adjusted to 5–6 with sodium bicarbonate solution and the mixture extracted again with methylene chloride. The dried extract was concentrated and the residue crystallized to give a further 2.65 g of the desired product.

The following nicotinic acid esters are prepared by one or more of the methods described above:

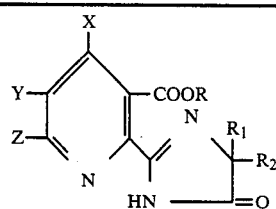

| R | $R_1$ | $R_2$ | X | Y | Z | mp °C. |
|---|---|---|---|---|---|---|
| $CH_3$ | $CH_3$ | $C_2H_5$ | H | H | H | 126.5–128.5 |
| $CH_2\equiv CH$ | $CH_3$ | $CH(CH_3)_2$ | H | H | H | 104.0–106.0 |
| $CH_3$ | —CH—($CH_2)_4$— <br> \| <br> $CH_3$ | | H | H | H | 151.0–155.3 |
| $CH_2C\equiv CH$ | —CH—($CH_2)_4$— <br> \| <br> $CH_3$ | | H | H | H | 117.0–120.0 |
| $CH_2C_6H_5$ | —CH—($CH_2)_4$— <br> \| <br> $CH_3$ | | H | H | H | 148.5–151.3 |
| $CH_2C\equiv CH$ | $CH_3$ | $CH_3$ | H | H | H | 171.0–173.0 |
| $CH_3$ | $CH_3$ | $CH_3$ | H | H | H | 148.0–150.0 |
| $CH_2C_6H_5$ | $CH_3$ | $CH_3$ | H | H | H | 142.0–144.0 |
| $CH_2C_6H_5$ | $CH_3$ | $C_2H_5$ | H | H | H | 118.0–120.0 |
| $CH_2C\equiv CH$ | $CH_3$ | $C_2H_5$ | H | H | H | 138.0–140.0 |
| —$C_{12}H_{25}$—n | $CH_3$ | $CH(CH_3)_2$ | H | H | H | 55.0–57.0 |
| —$C_2H_5$ | $CH_3$ | $CH(CH_3)_2$ | H | H | H | 72.0–75.0 |
| $CH_2CH_2OCH_2C_6H_5$ | $CH_3$ | $CH(CH_3)_2$ | H | H | H | 90.0–92.5 |
| —$CH_2$—(furan) | $CH_3$ | $CH(CH_3)_2$ | H | H | H | 120.5–122.0 |
| —$CH(CH_3)_2$ | $CH_3$ | $CH(CH_3)_2$ | H | H | H | 94.0–97.5 |
| —$CH_2C_6H_5$ | $CH_3$ | $CH(CH_3)_2$ | H | H | H | 122.0–125.0 |
| —$CH_2$—C≡C—$C_7H_{15}$—n | $CH_3$ | $CH(CH_3)_2$ | H | H | H | oil |
| $CH_2CH_2OCH_3$ | $CH_3$ | $CH(CH_3)_2$ | H | H | H | 60.0–63.0 |
| $CH_2CH=CH_2$ | $CH_3$ | $CH(CH_3)_2$ | H | H | H | 81.0–84.0 |

-continued

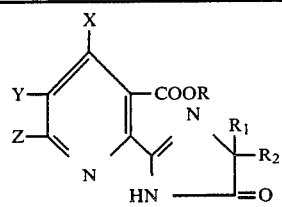

| R | R₁ | R₂ | X | Y | Z | mp °C. |
|---|----|----|----|----|----|--------|
| —CH(CH₃)—CH=CH₂ | CH₃ | CH(CH₃)₂ | H | H | H | oil |
| CH₂—C(CH₃)=CH₂ | CH₃ | CH(CH₃)₂ | H | H | H | 98.0–100.0 |
| —CH(CH₃)—C≡CH | CH₃ | CH(CH₃)₂ | H | H | H | oil |
| CH₂—CH=CHCH₃ | CH₃ | CH(CH₃)₂ | H | H | H | 87.0–89.0 |
| —C(CH₃)₃ | CH₃ | CH(CH₃)₂ | H | H | H | 124.0–126.0 |
| cyclohexyl | CH₃ | CH(CH₃)₂ | H | H | H | 95.0–98.0 |
| C₁₈H₃₇—n | CH₃ | CH(CH₃)₂ | H | H | H | 77.3–79.2 |
| CH₂C₆H₅ | CH₃ | CH(CH₃)₂ | H | H | H | 116.5–119.0 |
| —CH₂C₆H₅ | CH₃ | CH₂CH(CH₃)₂ | H | H | H | 76.0–78.5 |
| CH₃ | CH₃ | CH₂CH(CH₃)₂ | H | H | H | 92.0–94.0 |
| —C₄H₉—n | CH₃ | CH₂(CH₃)₂ | H | H | H | 54.0–57.0 |
| CH₂C≡CH | CH₃ | CHCH(CH₃)₂ | H | H | H | 128.5–131.0 |
| CH₃ | CH₃ | cyclopropyl | H | H | H | 128.0–131.0 |
| CH₂C₆H₅ | CH₃ | cyclopropyl | H | H | H | 111.0–113.0 |
| CH₃ | CH₃ | CH(CH₃)₂ | H | H | OCH₃ | 154.0–155.0 |
| CH₂—CH=CH—C₇H₁₅—n | CH₃ | CH(CH₃)₂ | H | H | H | oil |
| CH₂—C(Cl)=CH₂ | CH₃ | CH(CH₃)₂ | H | H | H | 73.0–77.0 |
| C₆H₁₃—n | CH₃ | CH(CH₃)₂ | H | H | H | oil |
| CH(CH₃)CH=CH—CH₃ | CH₃ | CH(CH₃)₂ | H | H | H | oil |
| CH₃ | —(CH₂)₅— | | H | H | H | 146.0–148.0 |
| CH₂CH=(CH₃)₂ | CH₃ | CH(CH₃)₂ | H | H | H | 77.5–79.0 |
| CH₂C₆H₅ | —(CH₂)₅— | | H | H | H | 117.0–122.0 |
| CH₂≡CCH₂OH | CH₃ | CH(CH₃)₂ | H | H | H | gum |
| CH₂C₆H₅ | C₂H₅ | C₂H₅ | H | H | H | 114.5–118.0 |
| C(CH₃)C≡CH | CH₃ | CH(CH₃)₂ | H | H | H | 128.0–132.0 |
| CH₂CH₂N⊕(CH₃)₃I⊖ | CH₃ | CH(CH₃)₂ | H | H | H | 165.0–175.0 |
| CH₃ | C₂H₅ | C₂H₅ | H | H | H | 132.5–135.5 |
| C(CH₃)₂C≡CH | CH₃ | CH(CH₃)₂ | H | H | H | 104.0–106.0 |
| CH₂C≡CH | CH₃ | Δ | H | H | H | 122.0–124.0 |
| CH₂C≡CH | —(CH₂)— | | H | H | H | 164.5–166.5 |
| CH₃ | CH₃ | CH(CH₃)₂ | CH₃ | H | H | 114.0–115.5 |
| CH₂C≡CH | C₂H₅ | C₂H₅ | H | H | H | 135.5–137.0 |
| CH₂—C₆H₄—OCH₃ (p) | CH₃ | CH(CH₃)₂ | H | H | H | 111.0–113.0 |

-continued

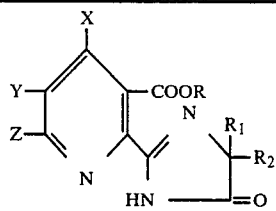

| R | R₁ | R₂ | X | Y | Z | mp °C. |
|---|---|---|---|---|---|---|
| CH₂–C₆H₄–Cl | CH₃ | CH(CH₃)₂ | H | H | H | 136.0–138.0 |
| CH₂–C₆H₄–NO₂ | CH₃ | CH(CH₃)₂ | H | H | H | 131.5–133.0 |
| CH₂COOCH₃ | CH₃ | CH(CH₃)₂ | H | H | H | 104.0–108.0 |
| CH₂–CH(OCO-H)–O–C(CH₃)₃ | CH₃ | CH(CH₃)₂ | H | H | H | oil |
| CH₂CH₂CH₂COOC₂H₅ | CH₃ | CH(CH₃)₂ | H | H | H | 133.0–135.0 |
| CH₃ | CH₃ | CH(CH₃)₂ | Br | H | H | 122.5–126.0 |
| CH₂CH=CH–COOC₂H₅ | CH₃ | CH(CH₃)₂ | H | H | H | oil |
| (CH₂)₄COOCH₃ | CH₃ | CH(CH₃)₂ | H | H | H | oil |
| CH₂–C₆H₄–C(CH₃)₃ | CH₃ | CH(CH₃)₂ | H | H | H | 108.0–111.0 |
| CH₂CH₂–C₆H₅ | CH₃ | CH(CH₃)₂ | H | H | H | 107.0–109.0 |
| CH₂–C₆H₅ | CH₃ | CH(CH₃)₂ | CH₃ | H | H | 130.0–132.0 |
| CH₂CH=CH–C₆H₅ | CH₃ | CH(CH₃)₂ | H | H | H | 113.0–115.0 |
| CH₂CH=C(CH₃)–CH₂CH₂CH=C(CH₃)₂ | CH₃ | CH(CH₃)₂ | H | H | H | oil |
| CH₂CH(OH)CH₂OH | CH₃ | CH(CH₃)₂ | H | H | H | oil |
| (CH₂)₃C≡CH | CH₃ | CH(CH₃)₂ | H | H | H | 73.0–75.0 |
| CH₂CH₂–(pinanyl with 2 CH₃) | CH₃ | CH(CH₃)₂ | H | H | H | oil |
| CH₉C₆H₅)COOCH₃ | CH₃ | CH(CH₃)₂ | H | H | H | oil |
| CH₂CH₂–C(CH₃)=CH₂ | CH₃ | CH(CH₃)₂ | H | H | H | oil |
| (CH₂)₉CH=CH₂ | CH₃ | CH(CH₃)₂ | H | H | H | oil |
| CH(CH₃)C₆H₅ | CH₃ | CH(CH₃)₂ | H | H | H | oil |
| CH₃ | –[CH(CH₂)₄ | CH₃]– | H | H | H | 122.0–124.0 |

-continued

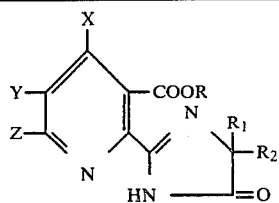

| R | R₁ | R₂ | X | Y | Z | mp °C. |
|---|---|---|---|---|---|---|
| CH₂—C₆H₅ | —[CH(CH₂)₄\|CH₃]— | | H | H | H | 123.0–125.0 |
| CH₂C≡CH | —[CH(CH₂)₄\|CH₃]— | | H | H | H | 132.0–134.5 |
| CH₃ | CH₃ | CH(CH₃)₂ | H | H | Cl | 102.5–104.5 |
| CH₂COOCH₂CH₃ | CH₃ | CH(CH₃)₂ | H | H | H | 86.0–90.0 |
| CH₂COOH | CH₃ | CH(CH₃)₂ | H | H | H | 187.0–189.0 |
| CH₂COOCH₂C₆H₅ | CH₃ | CH(CH₃)₂ | H | H | H | 121.5–123.0 |
| CH₂COOH | CH₃ | CH(CH₃)₂ | H | H | H | 106.0–110.0 |
| CH₃ | CH₃ | CH(CH₃)₂ | H | H | H | 110.5–114.0 [α]_D = +27.28 |
| CH₂C₆H₅ | CH₃ | CH(CH₃)₂ | H | H | H | 102.0–105.0 [α]_D = +13.08 |
| CH₂C₆H₅ | CH₃ | CH(CH₃)₂ | H | H | H | 104.0–107.0 [α]_D = −12.76 |
| CH₃ | CH₃ | CH(CH₃)₂ | H | H | N(CH₃)₂ | 184.5–185.5 |
| N=C(CH₃)₂ | CH₃ | CH(CH₃)₂ | H | H | H | 117.0–119.5 |
| CH₂CCl₃ | CH₃ | CH(CH₃)₂ | H | H | H | 114.0–116.0 |
| CH₃ | CH₃ | CH(CH₃)₂ | H | H | OC₆H₅ | 128.0–131.0 |
| CH₃ | CH₃ | CH(CH₃)₂ | H | C₄H₉—n | H | 69.0–71.5 |
| CH₃ | CH₃ | CH(CH₃)₂ | Cl | H | H | 110.0–113.0 |
| CH₃ | CH₃ | CH(CH₃)₂ | H | H | CF₃ | 96.5–100.0 |
| CH₃ | CH₃ | CH(CH₃)₂ | H | H | —C₆H₄—Cl (p) | |
| CH₃ | CH₃ | CH(CH₃)₂ | H | H | —C₆H₄—CH₃ (p) | 190.0–191.0 |
| C₂H₅ | CH₃ | CH(CH₃)₂ | H | H | n-C₃H₇ | 85.0–87.0 |
| CH₃ | CH₃ | CH(CH₃)₂ | H | H | n-C₃H₇ | 124.0–126.0 |
| CH(CH₃)₂ | CH₃ | CH(CH₃)₂ | H | H | n-C₃H₇ | 115.0–122.0 |
| CH₃ | CH₃ | CH(CH₃)₂ | H | H | i-C₃H₇ | 122.0–124.5 |
| C₂H₅ | CH₃ | CH(CH₃)₂ | H | H | i-C₃H₇ | — |
| CH(CH₃)₂ | CH₃ | CH(CH₃)₂ | H | H | i-C₃H₇ | 106.5–110.5 |
| CH₃ | CH₃ | CH(CH₃)₂ | H | —(CH₂)₅— | | 170.0–174.0 |
| CH₃ | CH₃ | CH(CH₃)₂ | H | CH₃ | H | 129.0–130.5 |
| CH₃ | CH₃ | CH(CH₃)₂ | H | H | C₆H₅ | 162.0–164.0 |
| CH₃ | CH₃ | CH(CH₃)₂ | H | H | CH₃ | 95.5–97.5 |
| C₂H₅ | CH₃ | CH(CH₃)₂ | H | H | C₂H₅ | 110.0–113.0 |
| CH(CH₃)₂ | CH₃ | CH(CH₃)₂ | H | H | C₂H₅ | 111.0–123.0 |
| CH₃ | CH₃ | CH(CH₃)₂ | H | H | C₂H₅ | 139.0–140.0 |

EXAMPLE 7

Preparation of cis- and trans-methyl 6-(allyloxy)-2-(4-isopropyl-4-methyl-5-oxo-2-imidazolidinyl)nicotinate

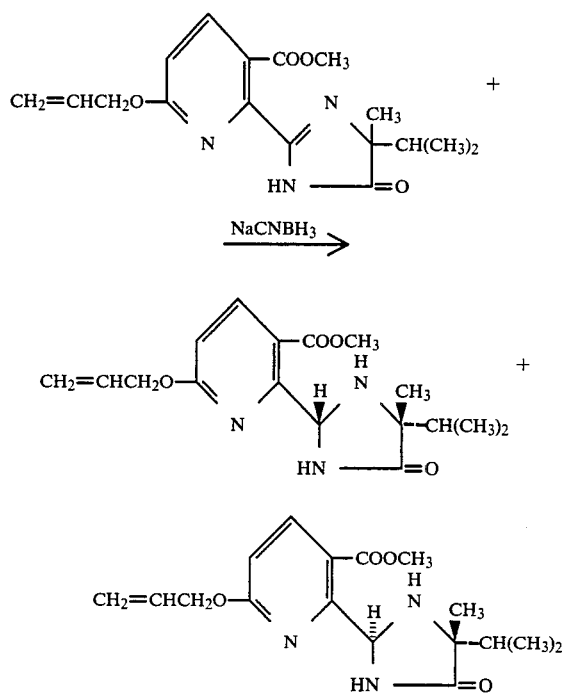

A solution containing 7.0 g (22.1 mmol) methyl 6-(allyloxy)-2-(4-isopropyl-4-methyl-5-oxo-2-imidazolin-2-yl)nicotinate in 70 mL absolute methanol is cooled to 0° C. and a few drops of methyl orange indicator added. To the stirred solution is added 1.8 mL (22.1 mmol) concentrated HCl. The red solution is warmed to room temperature and 1.4 g (22.1 mol) sodium cyanoborohydride is added. Slowly, the solution turns to an orange color (pH~4) and 2N methanolic HCl is added to the mixture until a red tint is observed (pH~3). This procedure of pH adjustment is repeated until there is no longer a change. After stirring overnight at room temperature, the solution is cooled to 0° C., the pH adjusted to ~0 with concentrated HCl to decompose residual NaCNBH$_3$. The pH is then adjusted to 5-6 with 5N NaOH. The methanol is removed in vacuo and enough water added to the residue to dissolve inorganic salts. This mixture is thoroughly extracted with CH$_2$Cl$_2$, the extracts dried and concentrated. The residue (~7.8 g) is a thick oil which is chromatographed on 350 g silica gel. Using 1:1 CH$_2$Cl$_2$-hexane followed by ether as eluants results in the separation of 0.35 g starting material. Further elution with ether results in the isolation of 1.87 g of the trans-isomer, and further elution with 10% methanol in ether gives 5.2 g of the cis-isomer.

The trans-isomer is recrystallized from CH$_2$Cl$_2$-hexanes to give 1.16 g of analytically pure trans-methyl 6-(allyloxy)-2-(4-isopropyl-4-methyl-5-oxo-2-imidazolidinyl)nicotinate, mp 144°-142° C.

Similarly the cis-isomer is recrystallized from CH$_2$Cl$_2$-hexane to give 4.6 g analytically pure cis-methyl 6-(alloxy)-2-(4-isopropyl-4-methyl-5-oxo-2-imidazolidinyl)nicotinate, mp 120°-122° C.

Using essentially the same procedure but substituting the appropriate 5-oxo- or 5-thioxo-imidazolinyl nicotinate for methyl 6-(allyloxy)-2-(4-isopropyl-4-methyl-5-oxo-2-imidazolin-2-yl)nicotinate, gives the following 5-oxo- and 5-thioxoimidazolidinyl nicotinates.

Other compounds that can be prepared by the above procedure are described in table III below.

TABLE III

Preparation of formula 2-(2-imidazolidinyl)nicotinates $$\underset{\text{HN}}{\overset{\text{X}}{\bigcirc}}\overset{\text{COOR}}{\underset{\text{N}}{\bigcirc}}\overset{R_1}{\underset{R_2}{=W}} \xrightarrow{\text{NaCNCH}_3} \underset{\text{HN}}{\overset{\text{X}}{\bigcirc}}\overset{\text{COOR}}{\underset{\text{N}}{\bigcirc}}\overset{R_1}{\underset{R_2}{=W}}$$

| R | R₁ | R₂ | W | X | Y | Z | Imidazolinyl nicotinate mp °C. | Imidazolidinyl nicotinate mp °C. cis | Imidazolidinyl nicotinate mp °C. trans |
|---|---|---|---|---|---|---|---|---|---|
| CH₃ | CH₃ | C₂H₅ | O | H | H | H | 126.5–128.5 | | |
| CH₂≡CH | CH₃ | CH(CH₃)₂ | O | H | H | H | 104.0–106.0 | 109–114 | 120–121 |
| CH₃ | —CH—(CH₂)₄— \|  CH₃ | | O | H | H | H | 151.0–155.3 | | |
| CH₂C≡CH | —CH—(CH₂)₄— \|  CH₃ | | O | H | H | H | 117.0–120.0 | | |
| CH₂C₆H₅ | —CH—(CH₂)₄— \|  CH₃ | | O | H | H | H | 148.5–151.3 | | |
| CH₂C≡CH | CH₃ | CH₃ | O | H | H | H | 171.0–173.0 | | |
| CH₃ | CH₃ | CH₃ | O | H | H | H | 148.0–150.0 | | |
| CH₂C₆H₅ | CH₃ | CH₃ | O | H | H | H | 142.0–144.0 | | |
| CH₂C₆H₅ | CH₃ | C₂H₅ | O | H | H | H | 118.0–120.0 | 147–151 | (mixture) |
| CH₂C≡CH | CH₃ | C₂H₅ | O | H | H | H | 138.0–140.0 | | |
| CH₃ | CH₃ | CH(CH₃)₂ | O | H | H | CF₃ | 96.5–100.0 | | |
| CH₃ | CH₃ | CH(CH₃)₂ | O | H | H | ![4-Cl-phenyl] | — | | |
| CH₃ | CH₃ | CH(CH₃)₂ | O | H | H | ![4-CH₃-phenyl] | 190.0–191.0 | 184–185 | 189–190 |
| C₂H₅ | CH₃ | CH(CH₃)₂ | O | H | H | n-C₃H₇ | 85.0–87.0 | | |

TABLE III-continued

Preparation of formula 2-(2-imidazolidinyl)nicotinates

| R | R₁ | R₂ | W | X | Y | Z | Imidazolinyl nicotinate mp °C. | Imidazolidinyl nicotinate mp °C. cis | Imidazolidinyl nicotinate mp °C. trans |
|---|---|---|---|---|---|---|---|---|---|
| CH₃ | CH₃ | CH(CH₃)₂ | O | H | H | n-C₃H₇ | 124.0–126.0 | | |
| CH(CH₃)₂ | CH₃ | CH(CH₃)₂ | O | H | H | n-C₃H₇ | 115.0–122.0 | | |
| CH₃ | CH₃ | CH(CH₃)₂ | O | H | H | i-C₃H₇ | 122.0–124.5 | | |
| C₂H₅ | CH₃ | CH(CH₃)₂ | O | H | H | i-C₃H₇ | — | | |
| CH(CH₃)₂ | CH₃ | CH(CH₃)₂ | O | H | H | i-C₃H₇ | 106.5–110.5 | | |
| CH₃ | CH₃ | CH(CH₃)₂ | O | H | H | —(CH₂)₅— | 170.0–174.0 | | |
| CH₃ | CH₃ | CH(CH₃)₂ | O | H | CH₃ | H | 129.0–130.5 | 133–134 | 116.5–118.0 |
| CH₃ | CH₃ | CH(CH₃)₂ | O | H | H | C₆H₅ | 162.0–164.0 | | |
| CH₃ | CH₃ | CH(CH₃)₂ | O | H | H | CH₃ | 95.5–97.5 | 145.0–147.5 | 120.0–123.5 |
| C₂H₅ | CH₃ | CH(CH₃)₂ | O | H | H | C₂H₅ | 110.0–113.0 | | |
| CH(CH₃)₂ | CH₃ | CH(CH₃)₂ | O | H | H | C₂H₅ | 111.0–123.0 | | |
| CH₃ | CH₃ | CH(CH₃)₂ | O | H | C₂H₅ | C₂H₅ | 139.0–140.0 | | |
| CH₃ | CH₃ | CH(CH₃)₂ | O | H | C₂H₅ | H | 96.0–99.0 | 119.0–123.0 | 106.0–111.0 |
| CH₂C₆H₅ | CH₃ | CH(CH₃)₂ | O | H | H | H | 121.0–123.5 | gum | 92.0–100.0 |
| CH₃ | CH₃ | CH(CH₃)₂ | O | H | H | OCH₂—CH=CH₂ | 117.0–119.0 | 120.0–122.0 | 141.0–142.0 |
| CH₃ | CH₃ | CH(CH₃)₂ | O | H | H | H | 110.5–114.0 | 95.5–102.0 | 89.0–94.0 |
| CH₂C₆H₅ | CH₃ | CH(CH₃)₂ | O | H | H | H | [α]D = +27.28 102.0–105.0 | | |
| CH₂C₆H₅ | CH₃ | CH(CH₃)₂ | O | H | H | H | 102.0–105.0 | | |
| CH₂C₆H₅ | CH₃ | CH(CH₃)₂ | O | H | H | H | [α]D = +13.08 104.0–107.0 | | |
| CH₃ | CH₃ | CH(CH₃)₂ | O | H | H | N(CH₃)₂ | [α]D = −12.76 184.5–185.5 | 162.0–164.0 | 136.0–139.0 |
| N=C(CH₃)₂ | CH₃ | CH(CH₃)₂ | O | H | H | H | 117.0–119.5 | | |
| CH₂CCl₃ | CH₃ | CH(CH₃)₂ | O | H | H | H | 114.0–116.0 | | |
| CH₃ | CH₃ | CH(CH₃)₂ | O | H | H | OC₆H₅ | 128.0–131.0 | | |
| CH₃ | CH₃ | CH(CH₃)₂ | O | H | C₄H₉—n | H | 69.0–71.5 | | |
| CH₃ | CH₃ | CH(CH₃)₂ | O | Cl | H | H | 110.0–113.0 | 141.0–142.0 | 158.0–159.0 |
| CH₃ | CH₃ | CH(CH₃)₂ | O | H | SCH₃ | H | 107.0–108.0 | | |
| CH₃ | —[CH(CH₂)₄ / CH₃]— | | O | H | H | H | 122.0–124.0 | | |

TABLE III-continued

Preparation of formula 2-(2-imidazolidinyl)nicotinates

| R | R$_1$ | R$_2$ | W | X | Y | Z | Imidazolinyl nicotinate mp °C. | Imidazolidinyl nicotinate mp °C. cis | Imidazolidinyl nicotinate mp °C. trans |
|---|---|---|---|---|---|---|---|---|---|
| CH$_2$—C$_6$H$_5$ | —[CH(CH$_2$)$_4$—CH$_3$]— | | O | H | H | H | 123.0–125.0 | | |
| CH$_2$C≡CH | —[CH(CH$_2$)$_4$—CH$_3$]— | | O | H | H | H | 132.0–134.5 | | |
| CH$_3$ | CH$_3$ | CH(CH$_3$)$_2$ | O | H | H | Cl | 102.5–104.5 | 146.0–148.0 | 118.0–120.0 |
| CH$_2$COOCH$_2$CH$_3$ | CH$_3$ | CH(CH$_3$)$_2$ | O | H | H | H | 86.0–90.0 | | |
| CH$_2$COOH | CH$_3$ | CH(CH$_3$)$_2$ | O | H | H | H | 187.0–189.0 | | |
| CH$_2$COOCH$_2$C$_6$H$_5$ | CH$_3$ | CH(CH$_3$)$_2$ | O | H | H | H | 121.5–123.0 | | |
| CH$_2$COOH | CH$_3$ | CH(CH$_3$)$_2$ | O | H | H | H | 106.0–110.0 | | |
| CH$_3$ | CH$_3$ | CH(CH$_3$)$_2$ | O | H | H | H | 110.0–112.0 [α]$_D$ = +27.41 | | |
| | CH$_3$ | CH(CH$_3$)$_2$ | S | H | H | H | 105.0–109.0 | 142.0–143.5 | 127.0–129.0 |
| | CH$_3$ | CH(CH$_3$)$_2$ | S | H | CH$_3$ | H | 135.0–137.5 | 155.0–157.0 | 149.0–151.5 |
| CH$_2$CH$_2$—C$_6$H$_5$ | CH$_3$ | CH(CH$_3$)$_2$ | O | H | H | H | 107.0–109.0 | | |
| CH$_2$—C$_6$H$_5$ | CH$_3$ | CH(CH$_3$)$_2$ | O | CH$_3$ | H | H | 130.0–132.0 | | |

TABLE III-continued

Preparation of formula 2-(2-imidazolidinyl)nicotinates $$\begin{array}{c}\text{structure with COOR, X, Y, Z, N, HN, R}_1\text{, R}_2\text{, W} \end{array} \xrightarrow{\text{NaCNCH}_3} \begin{array}{c}\text{product structure} \end{array}$$

| R | R₁ | R₂ | W | X | Y | Z | Imidazolinyl nicotinate mp °C. | Imidazolidinyl nicotinate mp °C. cis | trans |
|---|---|---|---|---|---|---|---|---|---|
| CH₂CH=CH—(phenyl) | CH₃ | CH(CH₃)₂ | O | H | H | H | 113.0–115.0 | | |
| CH₂CH=C(CH₃)—CH₂CH₂CH=C(CH₃)₂ | CH₃ | CH(CH₃)₂ | O | H | H | H | oil | | |
| CH₂CH(OH)CH₂OH | CH₃ | CH(CH₃)₂ | O | H | H | H | oil | | |
| (CH₂)₃C≡CH | CH₃ | CH(CH₃)₂ | O | H | H | H | 73.0–75.0 | | |
| CH₂CH₂—(pinane structure with CH₃'s) | CH₃ | CH(CH₃)₂ | O | H | H | H | oil | | |
| CH₉C₆H₅)COOCH₃ | CH₃ | CH(CH₃)₂ | O | H | H | H | oil | | |
| CH₂CH₂—C(CH₃)=CH₂ | CH₃ | CH(CH₃)₂ | O | H | H | H | oil | | |
| (CH₂)₉CH=CH₂ | CH₃ | CH(CH₃)₂ | O | H | H | H | oil | | |
| CH(CH₃)C₆H₅ | CH₃ | CH(CH₃)₂ | O | H | H | H | oil | | |
| CH₂—(C₆H₄-OCH₃) | CH₃ | CH(CH₃)₂ | O | H | H | H | 111.0–113.0 | | |
| CH₂—(C₆H₄-Cl) | CH₃ | CH(CH₃)₂ | O | H | H | H | 136.0–138.0 | | |

TABLE III-continued
Preparation of formula 2-(2-imidazolidinyl)nicotinates

| R | R₁ | R₂ | W | X | Y | Z | Imidazolinyl nicotinate mp °C. | Imidazolidinyl nicotinate mp °C. cis | Imidazolidinyl nicotinate mp °C. trans |
|---|---|---|---|---|---|---|---|---|---|
| $\text{CH}_2\text{-}C_6H_4\text{-}NO_2$ (para) | CH₃ | CH(CH₃)₂ | O | H | H | H | 131.5–133.0 | | |
| CH₂COOCH₃ | CH₃ | CH(CH₃)₂ | O | H | H | H | 104.0–108.0 | | |
| CH₂—CH—O—CH₃ / HCO—O—CH₃ | CH₃ | CH(CH₃)₂ | O | H | H | H | 95.0–97.0 | | |
| CH₂CH₂CH₂COOC₂H₅ | CH₃ | CH(CH₃)₂ | O | H | H | H | oil | | |
| CH(CH₃)COOCH₃ | CH₃ | CH(CH₃)₂ | O | H | Br | H | 133.0–135.0 | | |
| CH₃ | CH₃ | CH(CH₃)₂ | O | H | H | H | 122.5–126.0 | | |
| CH₂CH=CH—COOC₂H₅ | CH₃ | CH(CH₃)₂ | O | H | H | H | oil | | |
| (CH₂)₄COOCH₃ | CH₃ | CH(CH₃)₂ | O | H | H | H | oil | | |
| $\text{CH}_2\text{-}C_6H_4\text{-}C(CH_3)_3$ (para) | CH₃ | CH(CH₃)₂ | O | H | H | H | 108.0–111.0 | | |
| CH₂—C(Cl)=CH₂ | CH₃ | CH(CH₃)₂ | O | H | H | H | 73.0–77.0 | | |
| C₆H₁₃-n | CH₃ | CH(CH₃)₂ | O | H | H | H | oil | | |
| CH(CH₃)CH=CH—CH₃ | CH₃ | CH(CH₃)₂ | O | H | H | H | oil | | |
| CH₃ | —(CH₂)₅— | | O | H | H | H | 146.0–148.0 | | |
| CH₂CH=(CH₂)₂ | CH₃ | CH(CH₃)₂ | O | H | H | H | 77.5–79.0 | | |
| CH₂C₆H₅ | —(CH₂)₅— | | O | H | H | H | 117.0–122.0 | | |
| CH₃ | CH₃ | CH(CH₃)₂ | O | H | OCH₃ | H | 101.0–102.5 | 93.0–94.0 | |
| CH₂≡CCH₂OH | C₂H₅ | C₂H₅ | O | H | H | H | gum | | |
| CH₂C₆H₅ | CH₃ | CH(CH₃)₂ | O | H | H | H | 114.5–118.0 | | |
| C(CH₃)C≡CH | CH₃ | CH(CH₃)₂ | O | H | H | H | 128.0–132.0 | | |
| CH₂CH₂N⊕(CH₃)₃I⊖ | C₂H₅ | C₂H₅ | O | H | H | H | 165.0–175.0 | | |
| CH₃ | C₂H₅ | C₂H₅ | O | H | H | H | 132.5–135.5 | | 113.0–114.0 |

TABLE III-continued

Preparation of formula 2-(2-imidazolidinyl)nicotinates

| R | R$_1$ | R$_2$ | W | X | Y | Z | Imidazolinyl nicotinate mp °C. | Imidazolidinyl nicotinate mp °C. cis | Imidazolidinyl nicotinate mp °C. trans |
|---|---|---|---|---|---|---|---|---|---|
| C(CH$_3$)$_2$C≡CH | CH$_3$ | CH(CH$_3$)$_2$ | O | H | H | H | 104.0–106.0 | | |
| CH$_2$C≡CH | CH$_3$ | Δ | O | H | H | H | 122.0–124.0 | | |
| CH$_2$C≡CH | CH$_3$ | —(CH$_2$)— | O | H | H | H | 164.5–166.5 | | |
| CH$_3$ | CH$_3$ | CH(CH$_3$)$_2$ | O | CH$_3$ | H | H | 114.0–115.5 | | |
| CH$_2$C≡CH | C$_2$H$_5$ | C$_2$H$_5$ | O | H | H | H | 135.0–137.0 | | |
| —C(CH$_3$)$_3$ | CH$_3$ | CH(CH$_3$)$_2$ | O | H | H | H | 124.0–126.0 | | |
| CH$_3$ | CH$_3$ | CH(CH$_3$)$_2$ | O | H | H | —(CH$_2$)$_3$— | 160.0–162.0 | 146.0–147.0 | 119.0–120.0 |
| CH$_3$ | CH$_3$ | CH(CH$_3$)$_2$ | O | H | H | H | 95.0–98.0 | | |
| C$_{18}$H$_{37}$—n | CH$_3$ | CH(CH$_3$)$_2$ | O | H | H | H | 77.3–79.2 | | |
| CH$_2$C$_6$H$_5$ | CH$_3$ | CH(CH$_3$)$_2$ | O | H | H | H | 116.5–119.0 | | |
| n-C$_3$H$_7$ | CH$_3$ | CH$_2$CH(CH$_3$)$_2$ | O | H | H | H | 76.0–78.5 | | |
| CH$_3$ | CH$_3$ | CH(CH$_3$)$_2$ | O | H | H | H | 92.0–94.0 | | |
| —C$_4$H$_9$—n | CH$_3$ | CH(CH$_3$)$_2$ | O | H | H | H | 54.0–57.0 | | |
| CH$_2$C≡CH | CH$_3$ | CHCH(CH$_3$)$_2$ | O | H | H | H | 128.5–131.0 | | |
| CH$_3$ (cyclohexyl) | CH$_3$ | | O | H | H | H | 128.0–131.0 | | |
| CH$_2$C$_6$H$_5$ (cyclopropyl) | CH$_3$ | | O | H | H | H | 111.0–113.0 | | |
| CH$_3$ | CH$_3$ | CH(CH$_3$)$_2$ | O | H | H | OCH$_3$ | 154.0–155.0 | 158.0–160.0 | 128.5–130.5 |
| CH$_3$—CH=CH—C$_7$H$_{15}$—n | CH$_3$ | CH(CH$_3$)$_2$ | O | H | H | H | oil | | |

TABLE III-continued
Preparation of formula 2-(2-imidazolidinyl)nicotinates $$\underset{\text{HN}}{\overset{\text{X}}{\bigotimes}}\overset{\text{COOR}}{\underset{\text{N}}{\bigotimes}}\overset{\text{R}_1}{\underset{\text{R}_2}{\underset{\text{=W}}{\bigg|}}} \xrightarrow{\text{NaCNCH}_3} \underset{\text{HN}}{\overset{\text{X}}{\bigotimes}}\overset{\text{COOR}}{\underset{\text{N}}{\bigotimes}}\overset{\text{R}_1}{\underset{\text{R}_2}{\underset{\text{=W}}{\bigg|}}}$$

| R | R₁ | R₂ | W | X | Y | Z | Imidazolinyl nicotinate mp °C. | Imidazolidinyl nicotinate mp °C. cis | Imidazolidinyl nicotinate mp °C. trans |
|---|---|---|---|---|---|---|---|---|---|
| —C₁₂H₂₅-n | CH₃ | CH(CH₃)₂ | O | H | H | H | 55.0–57.0 | | |
| —C₂H₅ | CH₃ | CH(CH₃)₂ | O | H | H | H | 72.0–75.0 | | |
| CH₂CH₂OCH₂C₆H₅ | CH₃ | CH(CH₃)₂ | O | H | H | H | 90.0–92.5 | | |
| ![furan-CH₂—] | CH₃ | CH(CH₃)₂ | O | H | H | H | 120.5–122.0 | | |
| —CH(CH₃)₂ | CH₃ | CH(CH₃)₂ | O | H | H | H | 94.0–97.5 | | |
| —CH₂C₆H₅ | CH₃ | CH(CH₃)₂ | O | H | H | H | 122.0–125.0 | 111.0–113.5 | 95.0–97.5 |
| —CH₂—C≡C—C₇H₁₅-n | CH₃ | CH(CH₃)₂ | O | H | H | H | oil | | |
| CH₂CH₂OCH₃ | CH₃ | CH(CH₃)₂ | O | H | H | H | 60.0–63.0 | | |
| CH₂CH=CH₂ | CH₃ | CH(CH₃)₂ | O | H | H | H | 81.0–84.0 | 116.0–117.0 | 109.0–111.0 |
| —CH—CH=CH₂<br>    \|<br>    CH₃ | CH₃ | CH(CH₃)₂ | O | H | H | H | oil | | |
| CH₂—C=CH₂<br>    \|<br>    CH₃ | CH₃ | CH(CH₃)₂ | O | H | H | H | 98.0–100.0 | | |
| CH₃ | CH₃ | CH(CH₃)₂ | O | H | Cl | H | 109.0–111.0 | 129.0–131.0 | 114.0–116.0 |
| CH₃ | CH₃ | CH(CH₃)₂ | O | H | —OCH₂CH=CH₂ | H | 103.0–105.0 | 88.0–90.0 | 119.0–120.0 |
| CH₂C₆H₅ | CH₃ | CH(CH₃)₂ | O | H | CH₃ | H | 135.0–137.0 | — | 90.0–97.0 |
| CH₃ | CH₃ | CH(CH₃)₂ | O | H | —OCH₂C≡CH | H | 83.0–84.0 | 103.0–105.0 | 116.0–117.0 |
| CH₃ | CH₃ | CH(CH₃)₂ | O | H | —OCHF₂ | H | 105.0–107.0 | 99.0–100.5 | 137.0–138.0 |
| CH₃ | CH₃ | CH(CH₃)₂ | O | H | CF₃ | H | 167.0–170.0 | | |

EXAMPLE 8

Preparation of cis- and trans-5-ethyl-2-(4-isopropyl-4-methyl-5-oxo-2-imidazolidinyl)nicotinic acid

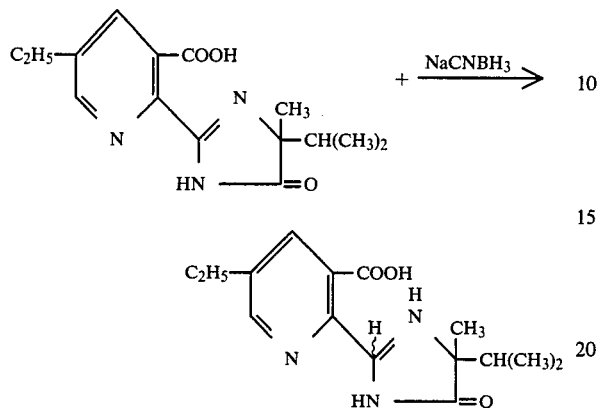

To a stirred slurry of 2.89 g 5-ethyl-2-(4-isopropyl-4-methyl-5-oxo-2-imidazolin-2-yl)nicotinic acid in 20 mL methanol and one equivalent of 2N methanolic HCl is added under nitrogen 0.6 g sodium cyanoborohydride. Methanolic HCl is added to maintain a pH of 2–3. After stirring the pH of the mixture is adjusted to 1 with concentrated HCl and after 15 minutes, again adjusted to 3 with saturated NaHCO$_3$ solution. After filtration, the solution is extracted with ethyl acetate. The pH of the aqueous phase is again adjusted to 3 and again extracted with ethyl acetate. A crystalline precipitate of cis- and trans-5-ethyl-2-(4-isopropyl-4-methyl-5-oxo-2-imidazolidinyl)nicotinate is formed which can be recrystallized from ethanol to give the product as a white crystalline solid mp 208°–210° C. This contains about 66% of the cis- and 34% of the trans-isomer.

EXAMPLE 9

Preparation of cis-6-(allyloxy)-2-(4-isopropyl-4-methyl-5-oxo-2-imidazolidynyl)nicotinic acid

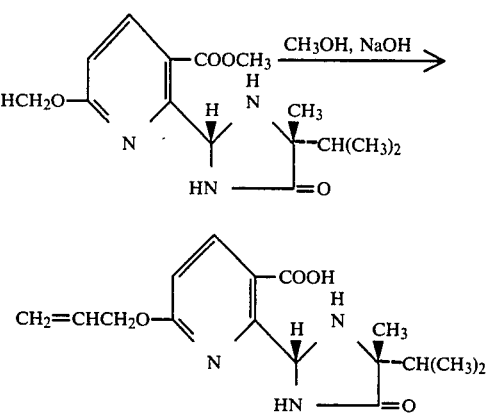

To a solution containing 3.9 g (12.2 mmol) cis-methyl 6-(allyloxy)-2-(4-isopropyl-4-methyl-5-oxo-2-imidazolidinyl)nicotinate in a minimum absolute methanol (~15 mL) is added 12.2 mL 2N NaOH solution. A precipitate results and the mixture is heated with stirring to 45° C. and maintained at that temperature for one hour. The solution becomes clear. It is cooled to 0° C. and 12.2 mL 2N HCl added. A solid precipitates which is collected, washed with ether and air dried. This material (3.2 g) is recrystallized from methylene chloride-hexane to give 2.3 g analytically pure cis-6-(allyloxy)-2-(4-isopropyl-4-methyl-5-oxo-2-imidazolidinyl)nicotinic acid, mp 193°–194° C.

By using essentially the same procedure, but substituting the appropriate methyl 5-oxo or thioxoimidazolinyl nicotinate or quinoline-3-carboxylate for cis-methyl 6-(allyloxy)-2-(4-isopropyl-4-methyl-5-oxo-2imidazolinyl)nicotinate, the following 5-oxo or 5-thioxoimidazolidinyl nicotinic, or quinoline-3-carboxylic acids are prepared. The reaction can be illustrated as follows using nicotinates as representative of the reaction.

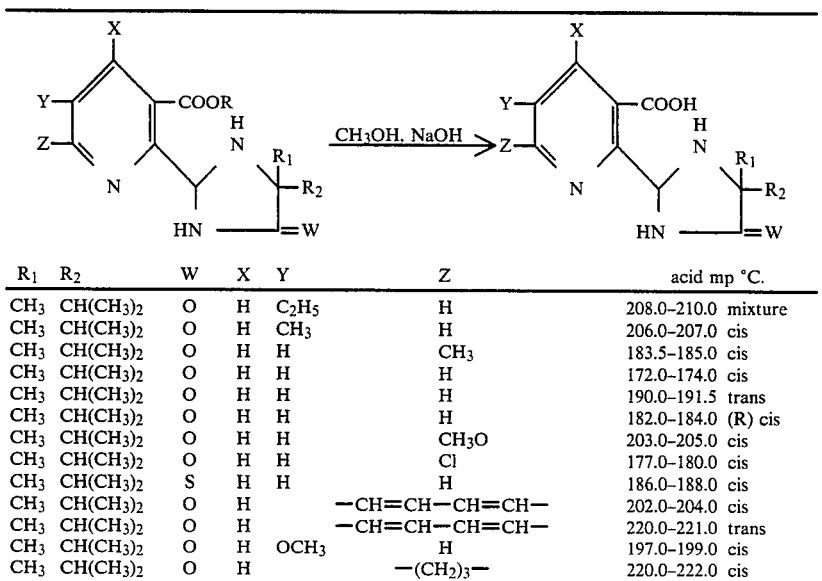

| R$_1$ | R$_2$ | W | X | Y | Z | acid mp °C. |
|---|---|---|---|---|---|---|
| CH$_3$ | CH(CH$_3$)$_2$ | O | H | C$_2$H$_5$ | H | 208.0–210.0 mixture |
| CH$_3$ | CH(CH$_3$)$_2$ | O | H | CH$_3$ | H | 206.0–207.0 cis |
| CH$_3$ | CH(CH$_3$)$_2$ | O | H | H | CH$_3$ | 183.5–185.0 cis |
| CH$_3$ | CH(CH$_3$)$_2$ | O | H | H | H | 172.0–174.0 cis |
| CH$_3$ | CH(CH$_3$)$_2$ | O | H | H | H | 190.0–191.5 trans |
| CH$_3$ | CH(CH$_3$)$_2$ | O | H | H | H | 182.0–184.0 (R) cis |
| CH$_3$ | CH(CH$_3$)$_2$ | O | H | H | CH$_3$O | 203.0–205.0 cis |
| CH$_3$ | CH(CH$_3$)$_2$ | O | H | H | Cl | 177.0–180.0 cis |
| CH$_3$ | CH(CH$_3$)$_2$ | S | H | H | H | 186.0–188.0 cis |
| CH$_3$ | CH(CH$_3$)$_2$ | O | H | —CH=CH—CH=CH— | | 202.0–204.0 cis |
| CH$_3$ | CH(CH$_3$)$_2$ | O | H | —CH=CH—CH=CH— | | 220.0–221.0 trans |
| CH$_3$ | CH(CH$_3$)$_2$ | O | H | OCH$_3$ | H | 197.0–199.0 cis |
| CH$_3$ | CH(CH$_3$)$_2$ | O | H | —(CH$_2$)$_3$— | | 220.0–222.0 cis |

-continued

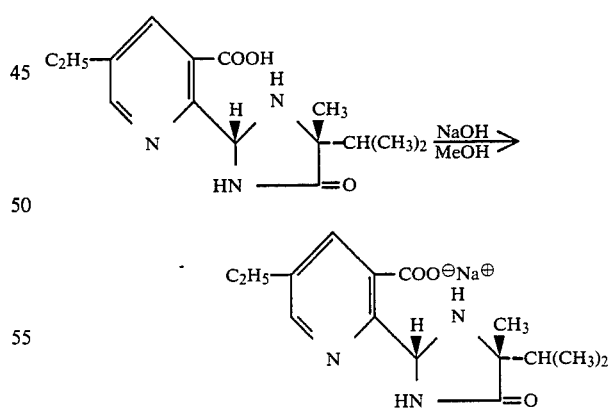

| $R_1$ | $R_2$ | W | X | Y | Z | acid mp °C. |
|---|---|---|---|---|---|---|
| $CH_3$ | $CH(CH_3)_2$ | O | H | —$(CH_2)_3$— | | 221.0–224.0 trans |
| $CH_3$ | $CH(CH_3)_2$ | O | H | $C_2H_5$ | H | 205.0–206.0 cis |
| $CH_3$ | $CH(CH_3)_2$ | O | H | $C_2H_5$ | H | 209.0–211.0 trans |
| $CH_3$ | $C_2H_5$ | O | H | H | H | 156.0–162.0 mixture |
| $CH_3$ | $CH(CH_3)_2$ | O | H | $CH_3$ | H | 207.0–208.0 trans |
| $CH_3$ | $CH(CH_3)_2$ | S | H | $CH_3$ | H | amorphous mixture |
| $CH_3$ | $CH(CH_3)_2$ | O | H | Cl | H | 208.0–211.0 cis |
| $CH_3$ | $CH(CH_3)_2$ | O | H | Cl | H | 183.0–223.0 mixture |
| $CH_3$ | $CH(CH_3)_2$ | O | H | $OCH_2CH=CH_2$ | H | 168.0–170.0 trans |
| $CH_3$ | $CH(CH_3)_2$ | O | H | $OCH_2CH=CH_2$ | H | 183.0–184.0 cis |
| $CH_3$ | $CH(CH_3)_2$ | O | H | $OCH_2C\equiv CH$ | H | 192.0–193.0 cis |
| $CH_3$ | $CH(CH_3)_2$ | O | H | $OCH_2C\equiv CH$ | H | 163.0–165.0 trans |
| $CH_3$ | $CH(CH_3)_2$ | O | H | $CH_3$ | H | 203.0–205.0 cis (2R, 4R) |
| $CH_3$ | $CH(CH_3)_2$ | O | H | $CH_3$ | H | 222.0–223.0 trans (2S, 4R) |
| $CH_3$ | $CH(CH_3)_2$ | O | H | H | —C6H4—$CH_3$ | 254.0–255.0 trans |
| $CH_3$ | $CH(CH_3)_2$ | O | H | $OCHF_2$ | H | 204.0–205.0 trans |
| $CH_3$ | $CH(CH_3)_2$ | O | H | $OCHF_2$ | H | 211.0–212.0 cis |
| $CH_3$ | $CH(CH_3)_2$ | O | H | H | $N(CH_3)_2$ | 243.5–245.0 cis |
| $CH_3$ | $CH(CH_3)_2$ | O | H | $SCH_3$ | H | 198.0–200.0 cis |
| $CH_3$ | $CH(CH_3)_2$ | O | H | $CF_3$ | H | cis |

EXAMPLE 10

Preparation of cis-methyl 2-(4-isopropyl-4-methyl-5-oxo-2-imidazolidinyl)nicotinate hydrochloride

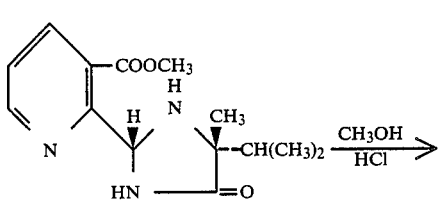

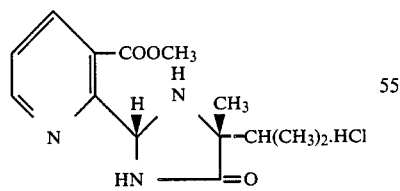

To 2.0 g cis-methyl 2-(4-isopropyl-4-methyl-5-oxo-2-imidazolidinyl)nicotinate is added 25 mL of 2N methanolic HCl. The solvent is removed in vacuo and the residue is crystallized from ethyl acetate-ether to give the hydrochloride salt, mp 189°–192° C. Other acid addition salts may be prepared by the above procedure using the appropriately substituted formula III 2-(2-imidazolidinyl)nicotinate.

EXAMPLE 11

Preparation of sodium 5-ethyl-2-(4-isopropyl-4-methyl-5-oxo-2-imidazolidinyl)nicotinate To 1.0 g 5-ethyl-2-(4-isopropyl-4-methyl-5-oxo-2-imidazolidinyl)nicotinic acid is added a solution of 0.1498 g sodium hydroxide in 20 mL absolute methanol. The mixture is stirred under nitrogen at room temperature overnight. The solvent is removed to give a solid which is dried in a vacuum oven at 60° C. for two days. The thus-formed sodium 5-ethyl-2-(4-isopropyl-4-methyl-5-oxo-2-imidazolidinyl)nicotinate darkens at 230° C. and decomposes at 247°–250° C.

EXAMPLE 12

Preparation of cis-methyl 2-(4-isopropyl-4-methyl-5-oxo-2-imidazolidinyl)nicotinate spectroscopy. Following the above procedure and using the appropriately substituted 2-formylpyridine-3-carboxylate yields the formula III 2-(2-imidazolidinyl)nicotinic acids and esters reported in Table IV below.

TABLE IV

Preparation of formula III 2-(2-imidazolidinyl)nicotinic acids and esters

| R | $R_1$ | $R_2$ | X | Y | Z | mp °C. |
|---|---|---|---|---|---|---|
| $CH_3$ | $CH_3$ | $CH(CH_3)_2$ | H | H | H | 118.5–120.0 cis |
| $CH_2C_6H_5$ | $CH_3$ | $CH(CH_3)_2$ | H | H | H | 107.0–109.0 cis |
| $CH_2$-furyl | $CH_3$ | $CH(CH_3)_2$ | H | H | H | 111.0–113.5 cis |
| $CH_2C{\equiv}CH$ | $CH_3$ | $CH(CH_3)_2$ | H | H | H | 109.0–114.0 cis |
| $CH_2CH{=}CH$ | $CH_3$ | $CH(CH_3)_2$ | H | H | H | 116.0–117.0 cis |
| $CH_3$ | $CH_3$ | $CH(CH_3)_2$ | H | H | H | 99.5–102.0 (R isomer) cis |
| $CH_3$ | $CH_3$ | $CH(CH_3)_2$ | H | $C_2H_5$ | H | 119.0–123.0 cis |
| $CH_2C_6H_5$ | $CH_3$ | $CH(CH_3)_2$ | H | $C_2H_5$ | H | gum |
| $CH_3$ | $CH_3$ | $CH(CH_3)_2$ | H | $CH_3$ | H | 133.0–134.0 cis |
| $CH_3$ | $CH_3$ | $CH(CH_3)_2$ | H | H | $CH_3$ | 145.0–147.5 cis |
| $CH_3$ | $CH_3$ | $CH(CH_3)_2$ | H | $OCH_3$ | H | 158.0–160.0 cis |
| $CH_3$ | $CH_3$ | $CH(CH_3)_2$ | H | H | $OCH_2CH{=}CH_2$ | 120.0–122.0 cis |
| $CH_3$ | $CH_3$ | $CH(CH_3)_2$ | H | H | Cl | 146.0–148.0 cis |
| $CH_3$ | $CH_3$ | $CH(CH_3)_2$ | H | $CH_3$ | $CH_3$ | 123.0–130.0 |
| $C_2H_5$ | $CH_3$ | $CH(CH_3)_2$ | H | —CH=CH—CH=CH— | | 156.0–164.0 cis |

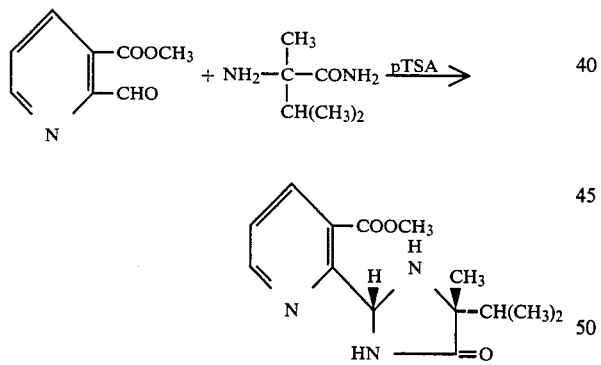

A solution containing 1.24 g methyl 2-formylpyridine-3-carboxylate [Bull. Soc. Chem. France, 36, 78–83 (1969)], 1.0 g 2-amino-2,3-dimethylbutyramide and 20 g p-toluene sulfonic acid is heated under reflux under nitrogen with a Dean-Stark water separator for six hours. The solution is filtered while hot and the filtrate concentrated in vacuo to leave a dark oil. The oil is extracted into ether, the ether concentrated to give a yellow solid. This solid is recrystallized from a mixture of hexane-ether and methylene chloride to give cis-methyl 2-(4-isopropyl-4-methyl-5-oxo-2-imidazolidinyl)nicotinate, mp 118.5°–120° C., identical to one of the products obtained from the sodium cyanoborohydride reduction of methyl 2-(4-isopropyl-4-methyl-5-oxo-imidazolin-2-yl)nicotinate. The presence of the corresponding trans-isomer is indicated by nmr

EXAMPLE 13

Preparation of cis- and trans-methyl 2-(4-isopropyl-4-methyl-5-thioxo-2-imidazolidinyl)nicotinate

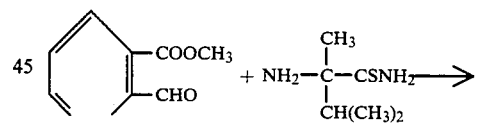

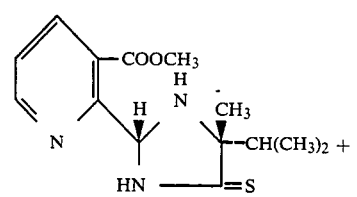

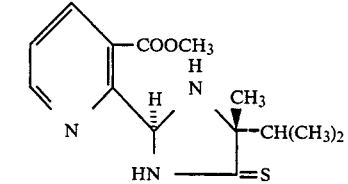

Using essentially the same conditions as described in Example 35, but substituting 2-amino-2,3-dimethylthiobutyramide for 2-amino-2,3-dimethylbutyramide gives a mixture of cis- and trans-methyl 2-(4-isopropyl-4-methyl-5-thioxo-2-imidazolidinyl)nicotinate from which essentially pure trans-isomer, mp 127°–129° C. can be isolated by chromatography of the crude product on silica gel. The melting point of the cis-isomer is 142°–143.5° C.

EXAMPLE 14

Preparation of cis- and trans-ethyl 2-(4-isopropyl-4-methyl-5-oxo-2-imidazolidinyl-2-yl)quinoline-3-carboxylate

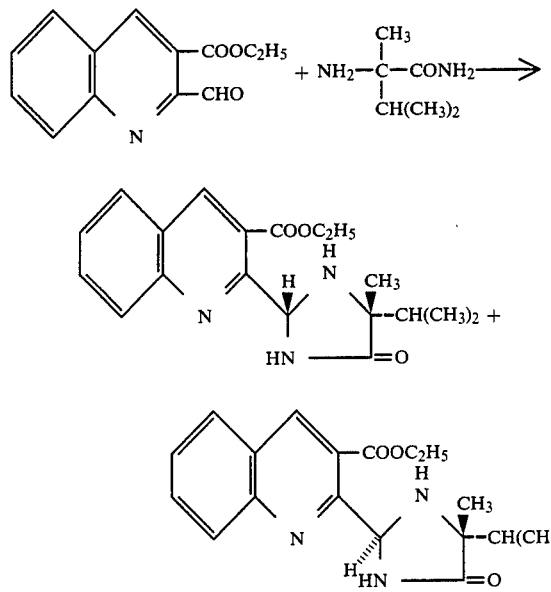

Using essentially the same procedure as described in Example 35, but substituting ethyl 2-formylquinoline-3-carboxylate [Godard et al., Bull. Chem. Soc. France, 906 (1971)] for the methyl 2-formylnicotinate, there is formed the cis-ethyl 2-(4-isopropyl-4-methyl-5-oxo-2-imidazolin-2-yl)quinoline-3-carboxylate, mp 156°–164° C. and trans-methyl 2-(4-isopropyl-4-methyl-5-oxo-2-imidazolin-2-yl)quinoline-3-carboxylate, mp 163°–164° C. Following the procedure of Example 33 but substituting a substituted 2-formylcarboxylate and using an appropriately substituted aminoamide in place of 2-amino-2,3-dimethylbutyramide will give the substituted formula IV 2-(2-imidazolidinyl)quinoline-3-carboxylate.

EXAMPLE 14-A

Preparation of ethyl 2-[2-(dimethylamino)vinyl]-5-nitronicotinate

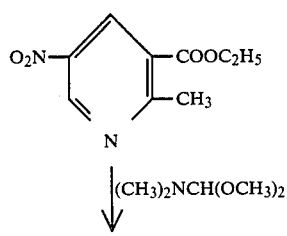

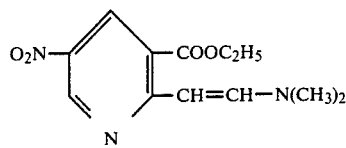

A solution containing 20.88 g of ethyl 2-methyl-5-nitronicotinate in 100 mL 1,1-dimethoxytriethylamine is heated at reflux for three hours and 15 minutes. The mixture is cooled and the solid collected by filtration, washed with methanol and air dried to give 26 g of the desired enamine as a dark red solid mp 176°–179° C.

EXAMPLE 14-B

Preparation of ethyl 2-[N-(1-carbamoyl-1,2-dimethylpropyl)formimidoyl]-5-nitronicotinate

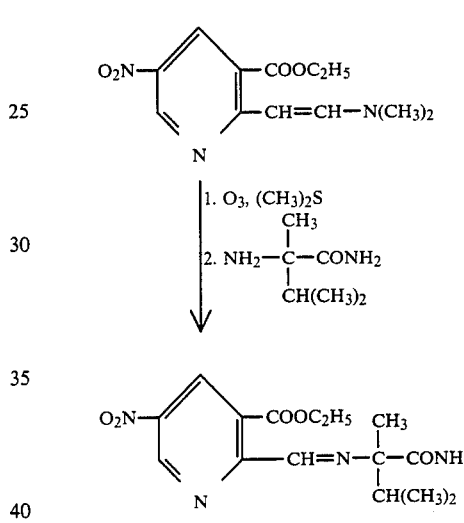

To a solution containing 18.9 g of the enamine in 200 mL CH$_2$Cl$_2$ and 10 mL methanol cooled in an ice bath is added ozone from a Welsback ozone generator operated at 120 v and air at 8 psi. This is continued until the red color of the enamine is discharged. The ozone is replaced by nitrogen and then 10 mL dimethylsulfide added. After 15 minutes, 9.8 g of 2-amino-2,3-dimethylbutyramide is added, the reaction mixture transferred to a 500 mL flask and concentrated. The residue is dissolved in 300 mL toluene and heated at reflux under a nitrogen atmosphere under a Dean-Stark water trap. After one hour, the solvent is removed and the residue, a black gum, which is mainly the Schiff base is used without further purification.

EXAMPLE 14-C

Preparation of cis- and trans-ethyl 2-(4-isopropyl-4-methyl-5-oxo-2-imidazolidinyl)-5-nitronicotinate

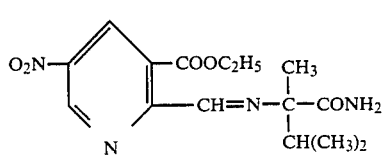

-continued

↓ TFA

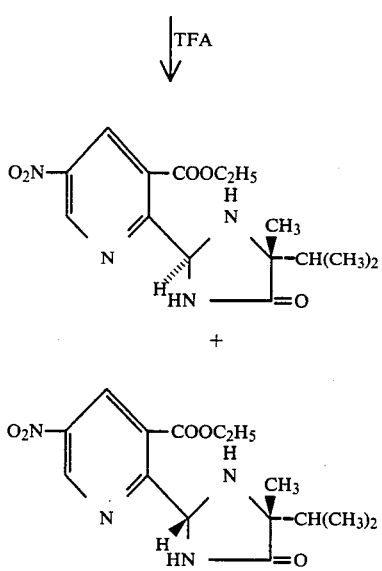

The crude Schiff base as described above is dissolved in 50 mL CH₂Cl₂ and treated with 4.6 mL trifluoroacetic acid at room temperature. After one hour an additional 1 mL acid is added and stirring continued for one hour. The mixture is cooled, 5.5 g sodium bicarbonate added. After the slow and careful addition of water, stirring is continued until CO₂ evolution ceases. The pH is adjusted to 7 with saturated sodium bicarbonate solution and the CH₂Cl₂ layer removed. The aqueous phase is reextracted three times with CH₂Cl. The combined extracts are dried and concentrated to give the crude product as a dark semi-solid. This material is chromatographed on silica gel. Using ether and hexane-ethyl acetate mixtures to develop and elute the products, trans-ethyl 2-(4-isopropyl-4-methyl-5-oxo-2-imidazoliinyl)-5-nitronicotinate is eluted first and is recrystallized from CH₂Cl₂-hexane to give the pure trans-isomer mp 116°–120° C.

The cis-isomer is eluted later and is recrystallized from CH₂Cl₂-hexane to give pure cis-ethyl 2-(4-isopropyl-4-methyl-5-oxo-2-imidazolidinyl)-5-nitronicotinate mp 149°–150.5° C.

EXAMPLE 14-D

Preparation of methyl 2-(4-isopropyl-4-methyl-5-oxo-2-imidazolin-2-yl)-5-(methylthio)nicotinate

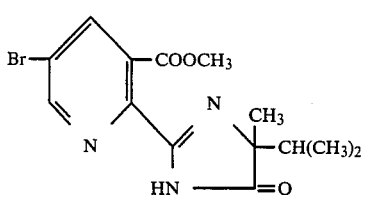

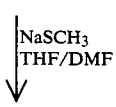 NaSCH₃
THF/DMF

-continued

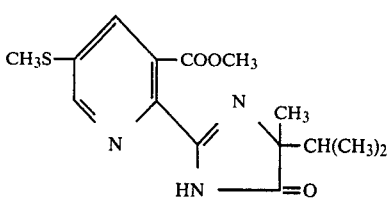

To a stirred solution containing 1.0 g bromo compound in 5 mL THF and 2 mL DMF is added 210 mg sodium methyl mercaptide under nitrogen. After two hours at 60° C., the mixture is cooled to room temperature, the pH adjusted to 4 with acetic acid, poured over ice and extracted with 2×50 mL ether. The extract is dried and concentrated to give a yellow oil which slowly solidifies. Recrystallization of the solid from ether/hexane gives pure methyl 2-(4-isopropyl-4-methyl-5-oxo-2-imidazolin-2-yl)-5-methylthio)nicotinate, mp 107°–108° C.

EXAMPLE 15

Preparation of dimethyl thieno[3,2-b]pyridine-5,6-dicarboxylate

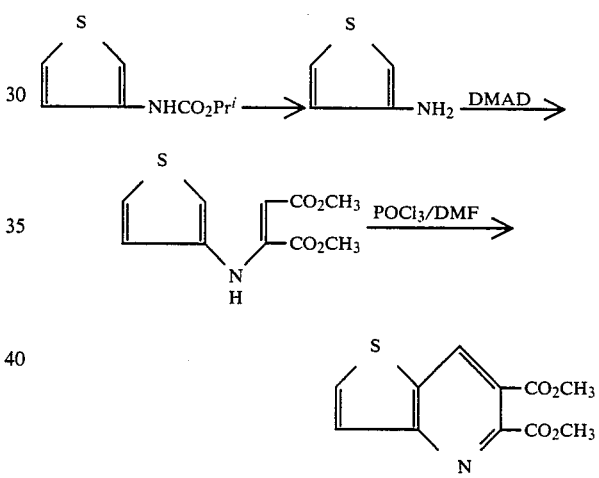

A mixture of isopropyl-3-thiophenecarbamate (177 g; 0.975 mol) in methanol (1.2 l) and water (2.8 l) containing sodium hydroxide (200 g) is heated at reflux for four hours. Methanol is removed under reduced pressure and the cooled reaction extracted with ether (5 l), and these extracts are washed with water, aqueous sodium chloride and dried. Evaporation under reduced pressure affords 3-aminothiophene as an oil in 57% crude yield.

3-Aminothiophene is redissolved in methanol (500 mL) cooled in an ice bath and dimethylacetylenedicarboxylate (80 g; 0.50 mol) is added dropwise. The mixture is stirred at room temperature for 15 hours and 30 minutes, the methanol removed under reduced pressure and 1,2-dichloroethane is added. This solvent is also evaporated off to give dimethyl 3-thienylaminobutenedioate as an oil.

A Vilsimeier reagent is prepared by adding dropwise, with stirring phosphorus oxychloride (86 g, 0.56 mol) to a cooled (5° C.) solution of DMF (41 g, 0.56 mol) in 1,2-dichloroethane (200 mL). This reagent is stirred at room temperature for one hour and 40 minutes, diluted with 1,2-dichloroethane (100 mL), cooled to 5° C. and then the above dimethyl ester dissolved in 1,2-dichloroethane (400 mL) is added to the Vilsmeier reagent at 5° C. dropwise over a 25 minute period. The reaction temperature is raised to room temperature for 15 minutes, then to reflux for a further two hours and 25 minutes. The cooled reaction mixture is chromatographed directly on a silica gel column affording 35.7 g (15%) of dimethyl thieno[3,2-b]pyridine-5,6-dicarboxylate mp 124°-125.5° C. after crystallization from hexane-ethyl acetate. A second crop (10.3 g) with mp 121°-124° C. is obtained giving an overall yield from isopropyl 3-thiophenecarbamate of 19%.

Utilizing the above procedure and substituting the appropriate substituted aminothiophene for isopropyl-3-aminothiophenecarbamate yields the compounds illustrated below.

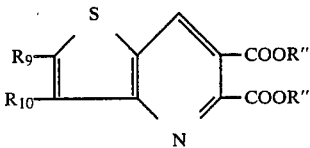

| R$_9$ | R$_{10}$ | R″ | mp °C. |
|---|---|---|---|
| H | H | H | 126-127 |
| CH$_3$ | H | CH$_3$ | — |
| Cl | H | CH$_3$ | — |

EXAMPLE 16

Preparation of dimethyl thieno[3,2-b]pyridine-5,6-dicarboxylate

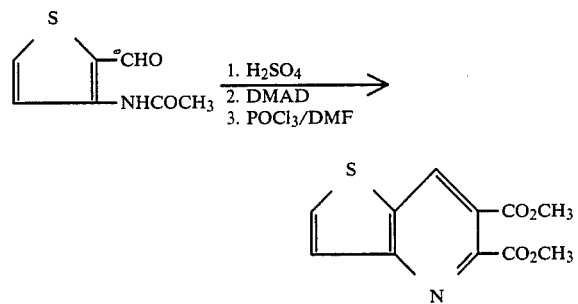

To concentrated sulfuric acid (170 mL), stirred at room temperature is added in portions 3-acetylamino-2-formylthiophene (17.5 g, 0.103 mol). The mixture is heated at 50° C. for 30 minutes, cooled and poured into an ice-water mixture. After neutralizing with an excess of sodium acetate, the mixture is ether (1×2 l) extracted. The organic layer was dried over anhydrous Na$_2$SO$_4$ and stripped to a dark red gum consisting of 3-amino-2-formylthiophene. Dimethylacetylenedicarboxylate (DMAD) (13 mL) in acetic acid (5 mL), piperidine (5 mL), methylene chloride (100 mL) and toluene (100 mL) is added to the 3-amino-2-formylthiophene and the mixture stirred overnight. Methylene chloride is removed by distillation and then the mixture heated at reflux for 24 hours. After cooling an additional 13 mL of DMAD is added and the reaction heated to reflux again for seven and one-half hours. After standing for 60 hours at room temperature, the solvents are removed and the dimethyl thieno[3,2-b]pyridine-5,6-dicarboxylate product is obtained by chromatography, after eluting with hexane-ethyl acetate, mp 124°-125° C.

EXAMPLE 17

Preparation of dimethyl 3-chloro[3,2-b]pyridine-5,6-dicarboxylate and dimethyl 2,3-dichlorothieno[3,2-b]pyridine-5,6-dicarboxylate

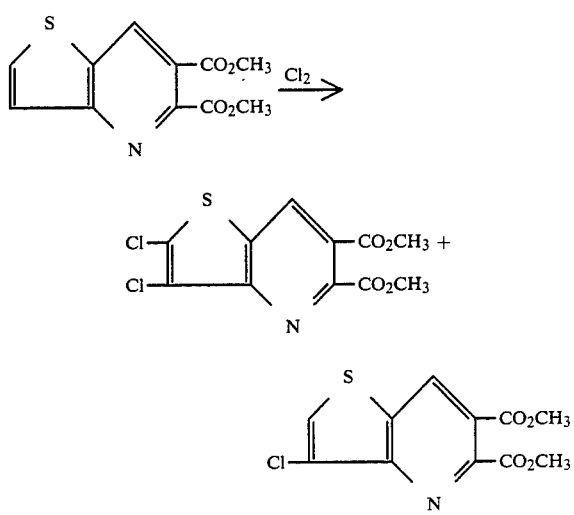

A solution of dimethyl thieno[3,2-b]pyridine-5,6-dicarboxylate (15 g 0.0525 mol) in acetic acid (680 mL) and sodium acetate (86 g, 0.093 mol) is maintained at 58° C. while chlorine is slowly introduced during five hours and 45 minutes. After reaction is complete, the mixture is flushed with nitrogen, ethyl acetate (200 mL) is added and solid sodium chloride filtered off and washed with ethyl acetate. The mother liquors and washes are combined and the solvents removed under reduced pressure. The residue is dissolved in methylene chloride and the solution washed with water, back extracted with methylene chloride and the combined methylene chloride layers washed with aqueous sodium bicarbonate, dried and stripped to give 18 g of solid. Chromatography on silica gel with 15% ethyl acetate-hexane, then 20% ethyl acetate-hexane gives the 2,3-dichloro compound, mp 173°-178° C., 1.3 g, followed by the 3-chlorothieno compound mp 166°-173° C. after crystallization from ethyl acetate-hexane.

EXAMPLE 18

Preparation of dimethyl 3-bromothieno[3,2-b]pyridine-5,6-dicarboxylate

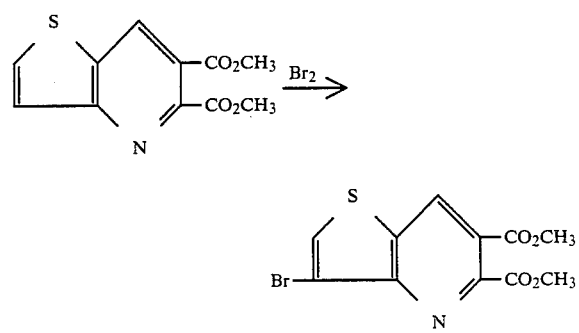

A solution of bromine (20 g, 0.125 mol) in acetic acid (50 mL) is added dropwise over three hours to a solution of dimethyl thieno[3,2-b]pyridine-5,6-dicarboxylate, (26.3 g, 0.104 mol), containing sodium acetate (17.2 g, 0.2 mol) in acetic acid (300 mL) at 85° C. Additional sodium acetate (18 g) and bromine (20 g) in acetic acid (50 mL) is added over an hour and the mixture stirred at 85° C. overnight. Bromine (10 g) is added in one portion then left at 85° C. for four hours. The mixture is cooled and treated with aqueous sodium bisulfite, diluted with ethyl acetate and concentrated. The reaction product is partitioned between water and methylene chloride and the organic layer washed with aqueous sodium chloride and the solvent removed. The residue is washed with ether to give 25 g of crude product, mp 165°-168° C. Recrystallization from methanol gave needles of dimethyl 3-bromothieno[3,2-b]pyridine-5,6-dicarboxylate, mp 168°-169° C.

EXAMPLE 19

Preparation of thieno[3,2-b]pyridine-5,6-dicarboxylic acid

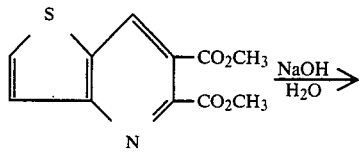

Dimethyl thieno[3,2-b]pyridine-5,6-dicarboxylate (3.75 g, 0.0149 mol) is added to a solution of sodium hydroxide (1.8 g, 0.045 mol) in water (20 mL) and the mixture is warmed at 60° C. for 20 hours. The reaction mixture is diluted with water, cooled in an ice bath, and acidified by the addition of concentrated hydrochloric acid. A precipitate of thieno[3,2-b]pyridine-5,6-dicarboxylic acid is filtered off and dried overnight to give 3.1 g (93%) mp >380° C.

Utilizing the above procedure and substituting the appropriate substituted thieno[3,2-b]pyridine-5,6-dicarboxylic acid diester yields the compounds illustrated below.

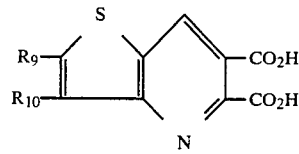

| $R_9$ | $R_{10}$ | mp °C. |
|---|---|---|
| H | H | >380 |
| H | Cl | None taken |
| H | Br | >380 |
| H | I | |
| H | F | |
| H | CN | |
| H | OCH$_3$ | |
| H | OH | |
| H | NO$_2$ | |
| H | N(CH$_3$)$_2$ | |
| CH$_3$ | H | |
| H | CH$_3$ | |
| CH$_3$ | CH$_3$ | |
| H | OCHF$_2$ | |
| H | SCH$_3$ | |
| H | SO$_2$N(CH$_3$)$_2$ | |
| C$_6$H$_5$ | H | |
| —(CH$_2$)$_3$— | | |
| —(CH$_2$)$_4$— | | |
| —(CH)$_4$— | | |
| Cl | Cl | |
| H | C$_6$H$_5$ | |
| C$_6$H$_5$ | H | |
| H | OC$_6$H$_5$ | |
| CF$_3$ | H | |

EXAMPLE 20

Preparation of 3-chlorothieno[3,2-b]pyridine 5,6-dicarboxylic acid anhydride

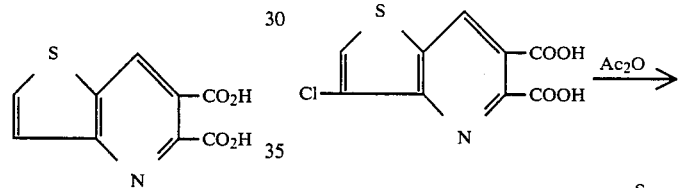

3-Chlorothieno[3,2-b]pyridine-5,6-dicarboxylic acid (1.45 g) is heated at 85° to 90° C. for 30 minutes then 90° to 102° C. for 30 minutes in acetic anhydride (7 mL). The reaction is cooled, the solids filtered off and washed with ether to give 1.2 g of 3-chlorothieno[3,2-b]pyridine-5,6-dicarboxylic acid anhydride.

Utilizing the above procedure and substituting the appropriate pyridine-5,6-dicarboxylic acid for 3-chlorothieno[3,2-b]pyridine-5,6-dicarboxylic acid yields the compounds illustrated below.

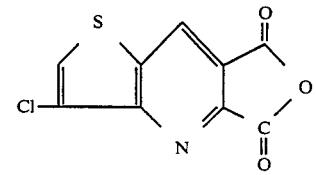

| $R_9$ | $R_{10}$ | mp °C. |
|---|---|---|
| H | H | 266-267 |
| H | Cl | Solid no mp obtained |
| H | Br | >380 |
| Cl | H | |
| Cl | Cl | |

-continued

| $R_9$ | $R_{10}$ | mp °C. |
|---|---|---|
| H | $NO_2$ | |
| $CH_3$ | H | |
| H | $N(CH_3)_2$ | |
| H | $SCH_3$ | |
| H | $OCH_3$ | |
| H | $CH_3$ | |
| H | F | |
| H | I | |
| $CH_3$ | $CH_3$ | |
| H | CN | |
| H | $OCHF_2$ | |
| $C_6H_5$ | H | |
| H | $SO_2N(CH_3)_2$ | |
| —$(CH_2)_3$— | | |
| —$(CH_2)_4$— | | |
| —$(CH)_4$— | | |
| Cl | Cl | |
| H | $C_6H_5$ | |
| $C_6H_5$ | H | |
| H | $OC_6H_5$ | |
| $CF_3$ | H | |

EXAMPLE 21

Preparation of
5-[(1-carbamoyl-1,2-dimethylpropyl)-carbamoyl]-3-chlorothieno[3,2-b]pyridine-6-carboxylic acid

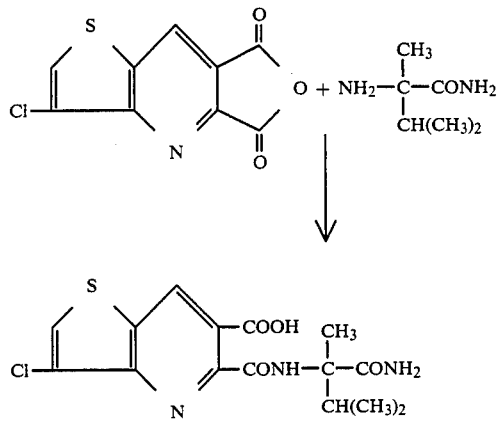

2-Amino-2,3-dimethylbutyramide (0.71 g) all in one portion is added to a stirred solution of 3-chlorothieno[3,2-b]pyridine-5,6-dicarboxylic acid anhydride, (1.2 g) in THF (1.0 mL). After standing for five minutes, the ice bath is removed and the reaction stirred at room temperature for 28 hours. THF (5 mL) is added and the mixture heated at reflux for two hours and then set aside overnight. The cooled mixture is filtered and the collected solid washed with ether to give 1.4 g of the desired 5-[(1-carbamoyl-1,2-dimethylpropyl)carbamoyl]3-chlorothieno[3,2-b]pyridine-6-carboxylic acid.

Utilizing the above procedure and substituting the appropriate pyridine-5,6-dicarboxylic acid anhydride for 3-chlorothieno[3,2-b]pyridine-5,6-dicarboxylic acid anhydride and the appropriate aminoamide yields the compounds illustrated below.

| $R_9$ | $R_{10}$ | $R_1$ | $R_2$ | mp °C. |
|---|---|---|---|---|
| H | H | $CH_3$ | $i$-$C_3H_7$ | |
| H | Cl | $CH_3$ | $i$-$C_3H_7$ | not pure |
| Cl | H | $CH_3$ | $i$-$C_3H_7$ | |
| Cl | Cl | $CH_3$ | $i$-$C_3H_7$ | |
| H | Br | $CH_3$ | $i$-$C_3H_7$ | |
| H | Me | $CH_3$ | $i$-$C_3H_7$ | |
| H | $NO_2$ | $CH_3$ | $i$-$C_3H_7$ | |
| H | $N(CH_3)_2$ | $CH_3$ | $i$-$C_3H_7$ | |
| H | $SCH_3$ | $CH_3$ | $i$-$C_3H_7$ | |
| H | $OCH_3$ | $CH_3$ | $i$-$C_3H_7$ | |
| $CH_3$ | H | $CH_3$ | $i$-$C_3H_7$ | |
| H | $SCH_3$ | $CH_3$ | $i$-$C_3H_7$ | |
| H | H | $CH_3$ | $C_3H_7$ | |
| H | H | $CH_3$ | $C_2H_5$ | |
| H | $OCHF_2$ | $CH_3$ | $i$-$C_3H_7$ | |
| $CH_3$ | $CH_3$ | $CH_3$ | $i$-$C_3H_7$ | |
| H | CN | $CH_3$ | $i$-$C_3H_7$ | |
| H | F | $CH_3$ | $i$-$C_3H_7$ | |
| H | I | $CH_3$ | $i$-$C_3H_7$ | |
| H | $SO_2N(CH_3)_2$ | $CH_3$ | $i$-$C_3H_7$ | |
| $C_6H_5$ | H | $CH_3$ | $i$-$C_3H_7$ | |
| —$(CH_2)_3$— | | $CH_3$ | $i$-$C_3H_7$ | |
| —$(CH_2)_4$— | | $CH_3$ | $i$-$C_3H_7$ | |
| —$(CH)_4$— | | $CH_3$ | $i$-$C_3H_7$ | |
| H | $C_6H_5$ | $CH_3$ | $i$-$C_3H_7$ | |
| $C_6H_5$ | H | $CH_3$ | $i$-$C_3H_7$ | |
| H | $OC_6H_5$ | $CH_3$ | $i$-$C_3H_7$ | |
| $CF_3$ | H | $CH_3$ | $i$-$C_3H_7$ | |

EXAMPLE 22

Preparation of
5-(4-isopropyl-4-methyl-5-oxo-2-imidazolin-2-yl)thieno[3,2-b]pyridine-6-carboxylic acid

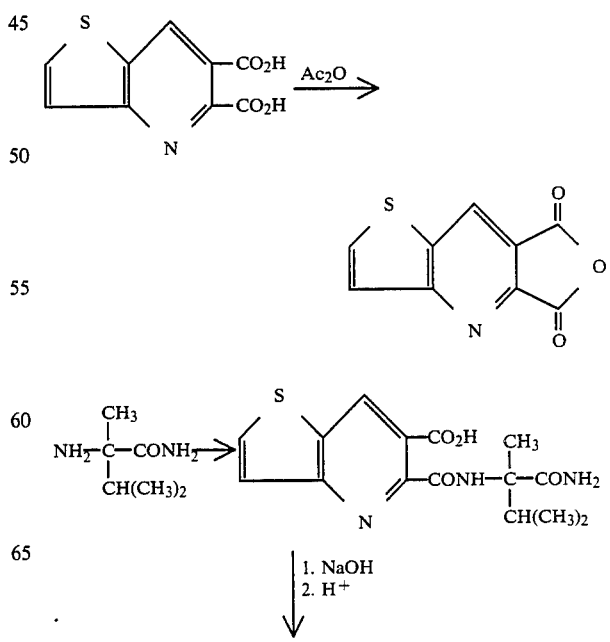

-continued

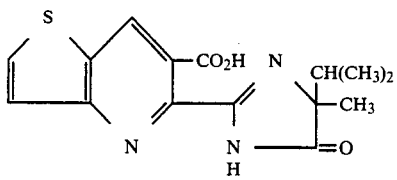

Thieno[3,2-b]pyridine-5,6-dicarboxylic acid (2.5 g, 0.011 mol) is heated slowly to 85° C. for one hour with acetic anhydride (25 mL), then cooled, filtered and washed with diethyl ether to give the anhydride as a solid, mp 266°–267° C. A mixture of the anhydride and 2-amino-2,3-dimethylbutyramide (2.6 g, 0.02 mol) in THF (70 mL) is stirred at room temperature for 15 hours. After heating at reflux for two hours, the mixture is cooled and diluted with THF (50 mL). Solid 5-[(1-carbamoyl-1,2-dimethylpropyl)carbamoyl]thieno[3,2-b]pyridine-6-carboxylic acid is filtered off, washed with ether and dried. The above solid is mixed with an aqueous 60 mL) solution of sodium hydroxide (6 g 0.05 mol) and heated at 85° C. for two hours and 30 minutes, then set aside at room temperature overnight. After cooling in an ice bath, the mixture is acidified to pH 3 with concentrated hydrochloric acid. A solid (3 g) is filtered off and dried. Crystallization from ethyl acetate affords (5-(4-isopropyl-4-methyl-5-oxo-2-imidazolin-2-yl)thieno[3,2-b]pyridine-6-carboxylic acid, mp 242°–244° C. in 46% yield.

Utilizing the above procedure and substituting the appropriate pyridine-5,6-dicarboxylic acid for thieno[3,2-b]pyridine-5,6-dicarboxylic acid yields the compounds illustrated below.

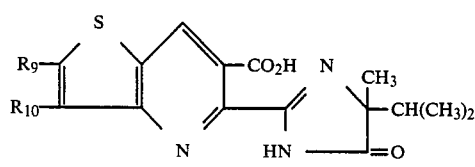

| $R_9$ | $R_{10}$ | mp °C. |
|---|---|---|
| H | H | 242–244 |
| H | Cl | 238–239 |
| H | Br | 226–227 |
| Cl | H | 266–267 |

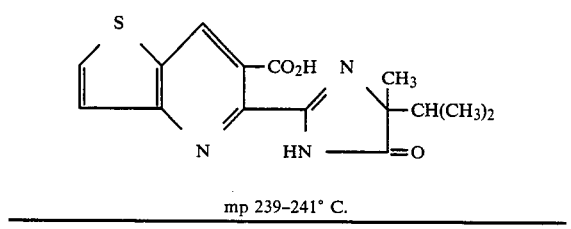

mp 239–241° C.

EXAMPLE 23

Preparation of diethyl furo[3,2-b]pyridine-5,6-dicarboxylate

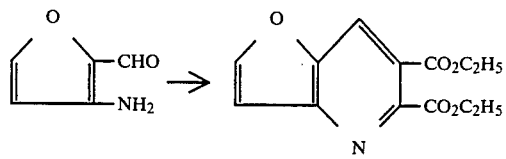

3-Amino-2-formylfuran, prepared from 3-azido-2-formylfuran (8.9 g 0.065 mol) is dissolved in ethanol and to this solution diethyl oxalactate (12.23 g, 0.065 mol) and ten drops of piperidine are added. In addition pulverized 3 Å molecular sieve is added and the reaction stirred at 65°–60° C. for three hours, then additional diethyl oxalacetate (2.2 g) is added. The reaction is essentially complete after 12 hours at 55°–60° C. On cooling the reaction is filtered, and the filtrate concentrated and then dissolved in ethyl acetate, water washed, then brine washed, dried over anhydrous magnesium sulfate and stripped to dryness. The residue is dissolved in 3:1 hexane:ethyl acetate and passed through a flash chromatographic column in two stages. First it is filtered by vacuum through a four to five inch pad of silica from which the last three fractions containing the required product are collected and combined. These combined fractions are then passed through a six inch column eluting under pressure with ethyl acetate:-hexane 3:1 and 2.1. Diethyl furo[3,2-b]pyridine-5,6-dicarboxylate 4.15 g (24%) is obtained after crystallization from hexane-ether, of mp 60°–64° C., and which with a mass spectrum m/e of 264.

Utilizing the above procedure and substituting the appropriate furan for 3-amino-2-formylfuran yields the compounds illustrated below.

| $R_9$ | $R_{10}$ | R" | mp °C. |
|---|---|---|---|
| H | H | $C_2H_5$ | 60–64 |
| H | Cl | $C_2H_5$ | |
| $CH_3$ | H | $C_2H_5$ | |
| H | $CH_3$ | $C_2H_5$ | |
| $C_2H_5$ | H | $C_2H_5$ | |
| H | $C_2H_5$ | $C_2H_5$ | |
| $CH_3$ | $CH_3$ | $C_2H_5$ | |

EXAMPLE 24

Preparation of furo[3,2-b]pyridine-5,6-dicarboxylic acid

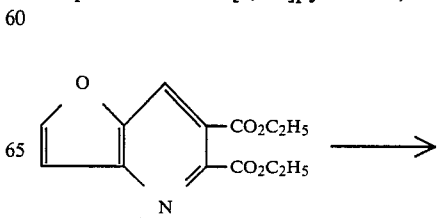

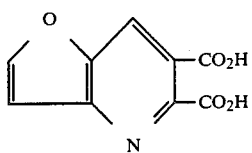

Furo[3,2-b]pyridine-5,6-dicarboxylic acid, diethyl ester (1.1 g, 0.0042 mol) is dissolved in 95% ethanol (20 mL) containing 10% aqueous sodium hydroxide (20 mL) and set aside at 0° C. for two days. The mixture is cooled, acidified and the solvent removed under reduced pressure. Water 5 mL is added and the hydrated product diacid obtained as a brown solid by filtration, 3.31 g (99%), mp 183° C. (dec). Anal calcd. as $C_9H_5NO_5.2\frac{1}{2}H_2O$ C, 42.86; H, 3.99; N, 5.55 found: C, 42.63; H, 2.63; N, 5.46.

EXAMPLE 25

Preparation of furo[3,2-b]pyridine-5,6-dicarboxylic acid anhydride

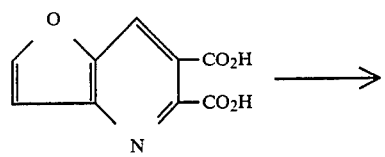

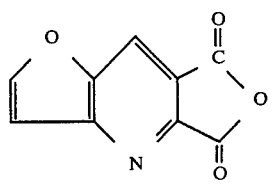

Furo[3,2-b]pyridine-5,6-dicarboxylic acid (3.3 g, 0.0159 mol) in acetic anhydride (100 mL) is heated to 70°–80° C. for six hours. The reaction mixture is cooled, filtered and the solid is washed with ether to give 3.01 (100%) of crude furo[3,2-b]pyridine-5,6-dicarboxylic acid anhydride.

EXAMPLE 26

Preparation of 5-[(1-carbamoyl-1,2-dimethylpropyl)carbamoyl]-furo[3,2-b]pyridine-6-carboxylic acid and 5-(4-isopropyl-4-methyl-5-oxo-2-imidazolin-2-yl)furo[3,2-b]pyridine-6-carboxylic acid

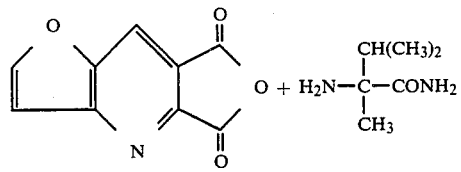

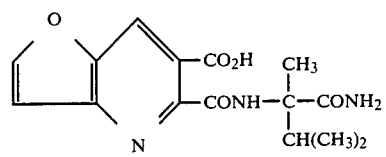

1. NaOH
2. Acid

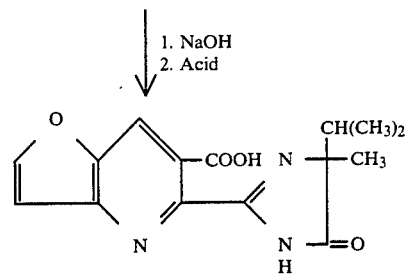

Furo[3,2-b]pyridine-5,6-dicarboxylic acid anhydride (3.01 g, 0.015 mol) is suspended in THF (100 mL) to which 2-amino-2,3-dimethylbutyramide (2.3 g, 0.018 mol) is added. After stirring for 20 hours, the solution is stripped to an oily solid which dissolves in a water/dilute sodium hydroxide solution. The alkaline solution is extracted with methylene chloride, and then acidified and reextracted with methylene chloride but on stirring only minute traces of material is isolated. The water layer is concentrated to an oily solid which is dissolved in ethanol, filtered and concentrated to a purple gum which is predominantly the crude product, 5-[(1-carbamoyl-1,2-dimethylpropyl)carbamoyl]furo[3,2-b]pyridine-6-carboxylic acid and is used without further purification to prepare the final 2-imidazolin-2-yl product by dissolving it in 10% sodium hydroxide solution (40 mL) and warming at 80° C. for three hours. On cooling the reaction is acidified and a small amount of solid precipitated out and was filtered off. Concentration of mother liquors gives a second crop, which is collected and combined with the first crop. Purification is effected by taking half of the material and separating on silica gel preparative glass plates as bands. The slower running band using methylene chloride:ethyl acetate:-chloroform:methanol 1:1:1:1 as eluant, affords the desired 2-imidazolin-2-yl product, mp 214°–223° C. (dec), Esters may then be prepared by the procedures described in Example 20.

Utilizing the above procedure and substituting the appropriate furo[3,2-b]pyridine-5,6-dicarboxylic anhydride yields the compounds illustrated below.

| $R_9$ | $R_{10}$ | mp °C. |
|---|---|---|
| H | H | 214–223 (dec) |
| H | Cl | |
| $CH_3$ | H | |
| H | $CH_3$ | |
| $C_2H_5$ | H | |
| H | $C_2H_5$ | |

-continued

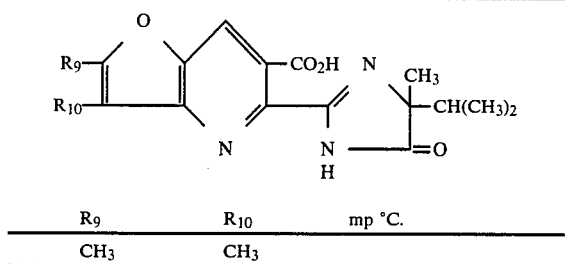

| $R_9$ | $R_{10}$ | mp °C. |
|---|---|---|
| $CH_3$ | $CH_3$ | |

EXAMPLE 27

Preparation of dimethyl thieno[2,3-b]pyridine-5,6-dicarboxylate

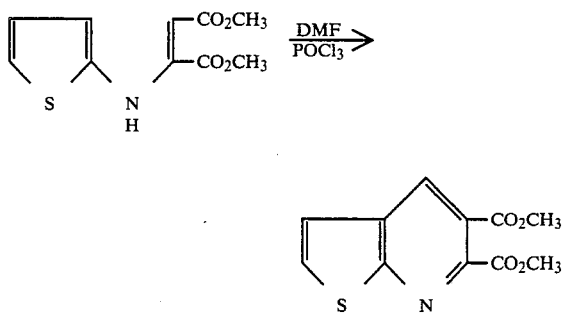

A Vilsmeier reagent is prepared by adding dropwise, with stirring, phosphorus oxychloride (40.29 g, 0.26 mol) to a cooled (10° C.) solution of DMF (19.0 g, 0.26 mol) in 1,2-dichloroethane (40 mL) in an $N_2$ atmosphere. This reagent is stirred at room temperature for one hour and 45 minutes. Dimethyl-2-thienylaminobutanedioate (63.4 g, 0.26 mol) dissolved in 1,2-dichloroethane (300 mL) is added dropwise to the Vilsmeier reagent at 7°–10° C. The reaction temperature is raised to room temperature for 15 minutes, then to reflux for 12 hours. The cooled reaction mixture is concentrated and the residue chromatographed on a silica gel column with ethyl acetate-hexane, affording dimethyl-thieno[2,3-b]pyridine-5,6-dicarboxylate (29 g, 45%) as a solid.

Utilizing the above procedure and substituting the appropriate dimethyl-2-thienylaminobutanedioate yields the compounds illustrated below.

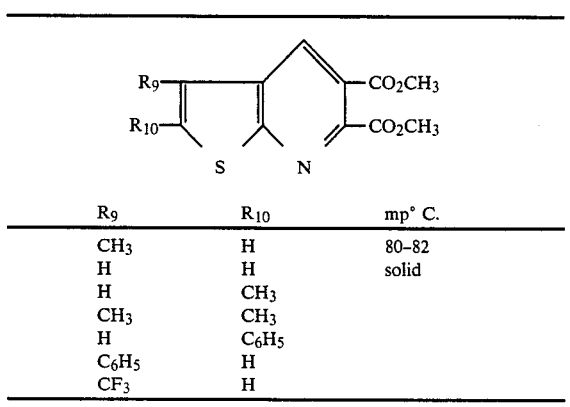

| $R_9$ | $R_{10}$ | mp° C. |
|---|---|---|
| $CH_3$ | H | 80–82 |
| H | H | solid |
| H | $CH_3$ | |
| $CH_3$ | $CH_3$ | |
| H | $C_6H_5$ | |
| $C_6H_5$ | H | |
| $CF_3$ | H | |

EXAMPLE 28

Preparation of dimethyl 3-bromothieno[2,3-b]pyridine-5,6-dicarboxylate

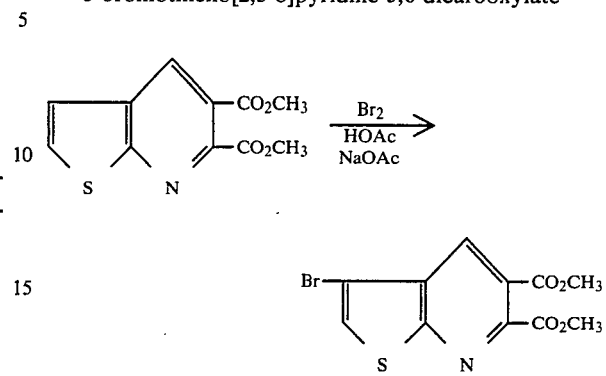

Bromine (0.33 , 0.00206 mol) in acetic acid (8 mL) is added to a stirred solution of dimethylthieno[2,3-b]pyridine-5,6-dicarboxylate (0.5 g, 0.00187 mol) in acetic acid containing sodium acetate (0.31 g, 0.00377 mol) at 40° C. The reaction mixture is heated at 75° C. for 18 hours. Evaluation of the mixture by tlc (silica gel) indicated incomplete reaction. Additional bromine (0.33 g) in acetic acid and sodium acetate (0.31 g) is added and heating at 75° C. continued for six hours. The reaction mixture is diluted with water and extracted into ethyl acetate. The separated organic layer is dried over anhydrous $MgSO_4$, filtered, and the filtrate concentrated to an oil which solidifies on standing. Crystallization of the crude product from ethyl acetate-hexanes yields the dimethyl 3-bromothieno[2,3-b]pyridine-5,6-dicarboxylate as white needles mp 86°–87.5° C.

This compound may readily be converted to a variety of substituted-thieno[2,3-b]pyridine compounds as illustrated below, while electrophilic substitution such as nitration or halogenation yields the additional compounds also listed below.

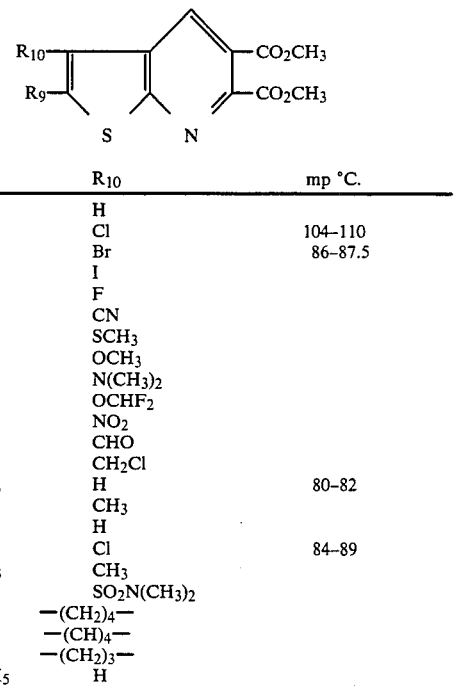

| $R_9$ | $R_{10}$ | mp °C. |
|---|---|---|
| H | H | |
| H | Cl | 104–110 |
| H | Br | 86–87.5 |
| H | I | |
| H | F | |
| H | CN | |
| H | $SCH_3$ | |
| H | $OCH_3$ | |
| H | $N(CH_3)_2$ | |
| H | $OCHF_2$ | |
| H | $NO_2$ | |
| H | CHO | |
| H | $CH_2Cl$ | |
| $CH_3$ | H | 80–82 |
| H | $CH_3$ | |
| Cl | H | |
| Cl | Cl | 84–89 |
| $CH_3$ | $CH_3$ | |
| H | $SO_2N(CH_3)_2$ | |
| —$(CH_2)_4$— | | |
| —$(CH)_4$— | | |
| —$(CH_2)_3$— | | |
| $C_6H_5$ | H | |

-continued

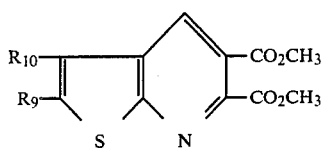

| $R_9$ | $R_{10}$ | mp °C. |
|---|---|---|
| H | $C_6H_5$ | |
| H | $OC_6H_5$ | |
| $CF_3$ | H | |

EXAMPLE 29

Preparation of thieno[2,3-b]pyridine-5,6-dicarboxylic acid

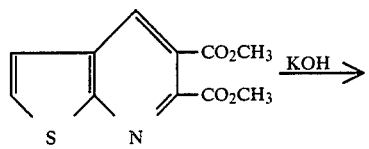 

A solution containing dimethyl thieno[2,3-b]pyridine-5,6-dicarboxylate (27.75 g, 0.11 mol) and potassium hydroxide (30.98 g, 0.55 mol) in methanol (200 mL) under a $N_2$ atmosphere is heated at reflux for two hours. The reaction mixture is cooled and sufficient water added to dissolve any solids present before evaporating the mixture to dryness. The resulting solid is dissolved in a minimum volume of water, cooled in an ice bath and acidified with concentrated $H_2SO_4$ to pH ~ 1. Thieno[2,3-b]pyridine-5,6-dicarboxylic acid is filtered off and dried overnight to give 23.36 g mp 272°–275° C.

Utilizing the above procedure and substituting the appropriate substituted dialkylthieno[2,3-b]pyridine-5,6-dicarboxylate yields the compounds illustrated below.

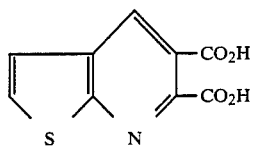

| $R_9$ | $R_{10}$ | mp °C. |
|---|---|---|
| H | H | 272–275 |
| H | Cl | >300 |
| H | Br | >315 |
| H | I | |
| H | F | |
| H | CN | |
| H | $SCH_3$ | |
| H | $OCH_3$ | |
| H | $N(CH_3)_2$ | |
| H | $OCHF_2$ | |
| H | $NO_2$ | |
| H | CHO | |
| H | $CH_2Cl$ | |
| H | $CH_3$ | 180–183 (dec) |

-continued

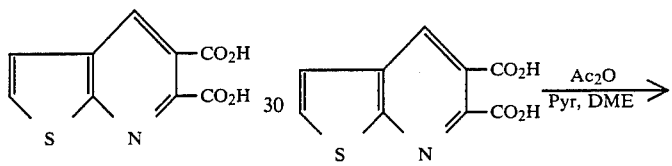

| $R_9$ | $R_{10}$ | mp °C. |
|---|---|---|
| $CH_3$ | H | |
| Cl | H | |
| Cl | Cl | |
| $CH_3$ | $CH_3$ | |
| $C_6H_5$ | H | |
| H | $SO_2N(CH_3)_2$ | |
| —$(CH_2)_3$— | | |
| —$(CH_2)_4$— | | |
| —$(CH)_4$— | | |
| H | $OC_6H_5$ | |
| H | $C_6H_5$ | |
| $CF_3$ | H | |

EXAMPLE 30

Preparation of thieno[2,3-b]pyridine-5,6-dicarboxylic anhydride

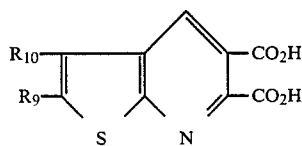

Acetic anhydride (37.4 g, 0.366 mol) is added to a stirred suspension of thieno[2,3-b]pyridine-5,6-dicarboxylic acid (21.52 g, 0.096 mol) in dimethoxyethane (175 mL) in an inert $N_2$ atmosphere. Upon addition of pyridine (16.78 g, 0.21 mol) at room temperature an exotherm to 45° C. is observed and a homogeneous solution results. The reaction mixture is then stirred at room temperature and the resulting solid filtered off, washed with ether and air dried to give 14.8 g (75%) of thieno[2,3-b]pyridine-5,6-dicarboxylic acid anhydride.

Utilizing the above procedure and substituting the appropriate substituted thieno[2,3-b]pyridine-5,6-dicarboxylic acid yields the compounds illustrated below.

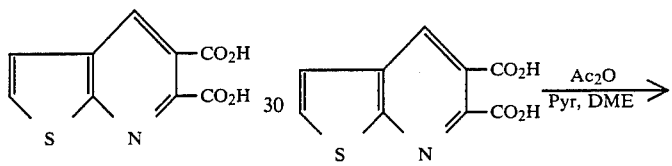

| $R_9$ | $R_{10}$ | mp °C. |
|---|---|---|
| $CH_3$ | H | 176–180 |
| H | Br | 228.5–231 |
| H | Cl | 230–300 (slow dec) |
| H | H | |
| H | — | |

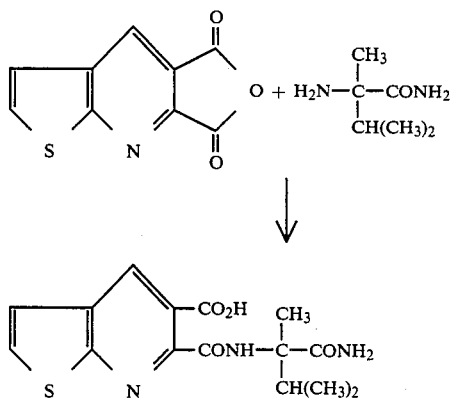

| R9 | R10 | mp °C. |
|---|---|---|
| H | I | |
| H | F | |
| H | CN | |
| H | SCH3 | |
| H | N(CH3)2 | |
| H | NO2 | |
| H | CHO | |
| H | CH2Cl | |
| H | CH3 | |
| CH3 | H | |
| Cl | H | |
| Cl | Cl | |
| CH3 | CH3 | |
| C6H5 | H | |
| H | SO2N(CH3)2 | |
| —(CH2)3— | | |
| —(CH2)4— | | |
| —(CH)4— | | |
| H | C6H5 | |
| H | OC6H5 | |
| CF3 | H | |

EXAMPLE 31

Preparation of 6-[(1-carbamoyl-1,2-dimethylpropyl)carbamoyl]-thieno[2,3-b]pyridine-5-carboxylic acid

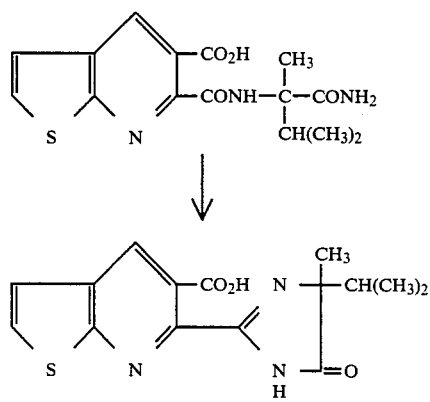

2-Amino-2,3-dimethylbutyramide (9.84 g, 0.076 mol) is added to a stirred suspension of thieno[2,3-b]pyridine-5,6-dicarboxylic acid anhydride (14.8 g, 0.072 mol) in THF under an inert atmosphere of $N_2$ at room temperature. The dark solution is stirred at room temperature overnight and the resulting solid filtered off, washed with THF and air dried to give 17.35 g (72%) of 6-[(1-carbamoyl-1,2-dimethylpropyl)carbamoyl]thieno[2,3-b]pyridine-5-carboxylic acid.

Utilizing the above procedure and substituting the appropriate substituted thieno[2,3-b]pyridine-5,6-dicarboxylic acid anhydride yields the compounds illustrated below.

| R9 | R10 | mp °C. |
|---|---|---|
| CH3 | H | 207–208 |
| H | Br | 176–178 |
| H | Cl | 156–158 |
| H | H | |
| H | I | |
| H | F | |
| H | CN | |
| H | SCH3 | |
| H | OCH3 | |
| H | N(CH3)2 | |
| H | NO2 | |
| H | CHO | |
| H | CH2Cl | |
| H | CH3 | |
| Cl | H | |
| Cl | Cl | |
| CH3 | CH3 | |
| C6H5 | H | |
| H | SO2N(CH3)2 | |
| —(CH2)3— | | |
| —(CH2)4— | | |
| —(CH)4— | | |
| H | C6H5 | |
| H | OC6H5 | |
| CF3 | H | |

EXAMPLE 32

Preparation of 6-(4-isopropyl-4-methyl-5-oxo-2-imidazolin-2-yl)thieno[2,3-b]pyridine-5-carboxylic acid 6-[(1-Carbamoyl-1,2-dimethylpropyl)carbamoyl]-thieno[2,3-b]pyridine-5-carboxylic acid (17.35 g, 0.052 mol) is added to water (225 mL) containing sodium hydroxide (10.35 g, 0.26 mol). The resulting basic solution is heated at 80° C. for two hours and 45 minutes, cooled in an ice-water bath and acidified with 6N $H_2SO_4$. The product 6-(4-isopropyl-4-methyl-5-oxo-2-imidazolin-2-yl)thieno[2,3-b]pyridine-5-carboxylic acid is filtered off, washed with water and air dried yielding 1.54 g, 70.3%, mp 221°–223° C.

EXAMPLE 33

Preparation of 2-isopropyl-2-methyl-5H-Imidazo[1',2':1,2]pyrrolo[3,4-b]thieno[3,2-e]pyridine-3(2H),5-dione

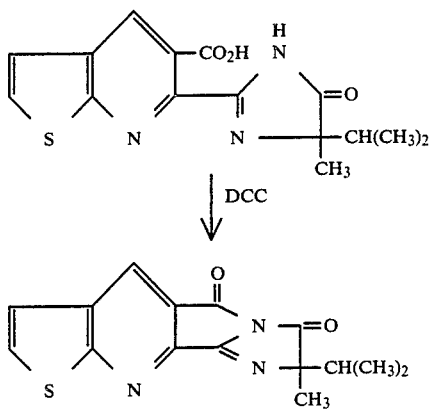

Dicyclohexylcarbodiimide (1.07 g, 0.005 mol) in methylene chloride (20 mL) is added dropwise to a stirred methylene chloride (30 mL) suspension of 6-(4-isopropyl-4-methyl-5-oxo-2-imidazolin-2-yl)thieno[2,3-b]-5-carboxylic acid (1.5 g, 0.0047 mol) under an $N_2$ atmosphere. After stirring the reaction mixture for 16 hours, it was clarified by filtration, concentrated to dryness and the resulting material purified by column chromatography on silica gel eluting with acetonitrile/methylene chloride (½). The solid product was crystallized from toluene to give the pure 3,5-dione as white crystals mp 214.5°–216.5° C.

EXAMPLE 34

Preparation of 2-propynyl 6-(4-isopropyl-4-methyl-5-oxo-2-imidazolin-2-yl)thieno[2,3-b]pyridine-5-carboxylate

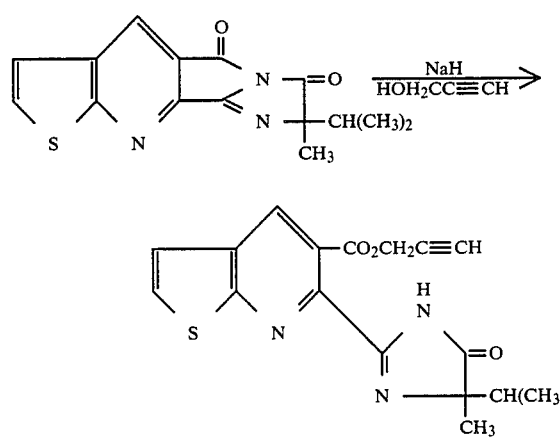

Sodium hydride (2.4 g, 60%, 0.126 mol) is added to the 3,5-dione (0.9 g, 0.003 mol) in propargyl alcohol (25 mL) at 10° C. under an inert $N_2$ atmosphere. The reaction mixture is stirred at room temperature for 60 hours and then neutralized with a saturated ammonium chloride solution. The resulting mixture is concentrated on a rotary evaporator, diluted with water and extracted with ethyl acetate. The organic layer is separated, dried over anhydrous $MgSO_4$ and concentrated to dryness.

Purification of the product by column chromatography on silica gel with methylene chloride/acetonitrile (85/15) yields 2-propynyl 6-(4-isopropyl-4-methyl-5-oxo-2-imidazolin-2-yl)pyridine-5-carboxylate, which after crystallization from toluene has a mp 188°–189.5° C.

Utilizing the procedures of Examples 49, 55, 56 and 57 and substituting the appropriate thieno or furo[3,2-b]pyridine or thieno or furo[2,3-b]pyridine compounds, yields the compounds illustrated below.

| B | $R_9$ | $R_{10}$ | R | mp° C. |
|---|---|---|---|---|
| S | H | H | $CH_3$ | 215–217 |
| S | H | H | H | 220–223.5 (dec) |
| S | H | H | $-CH_2C\equiv CH$ | 188–189.5 |
| S | H | H | $-CH_2-\text{(tetrahydrofuryl)}$ | 140–142 |
| S | H | H | $-CH_2C(CH_3)=CH_2$ | 108–110 |
| S | $CH_3$ | H | H | 225.5–227.5 |
| S | H | Br | H | 274–276 |
| S | H | Cl | H | 266–267 |
| O | H | H | H | 237–244 |
| S | H | $NO_2$ | $-CH_3$ | 201–202.5° C. |
| S | H | $NO_2$ | H | impure |
| S | Cl | H | H | 268 (dec) |
| S | H | $CH_3$ | H | 255–257 |
| S | $-(CH_2)_4-$ | | H | 234–237 |
| O | H | Cl | H | 239–240 |
| O | H | H | $CH_3$ | 134–137 |
| O | H | Br | H | 239–245 |
| O | $CH_3$ | H | H | 174–177 |
| O | $C_2H_5$ | H | H | 170–172 |
| O | $C_6H_5$ | H | H | 244–245 |
| O | H | Cl | $CH_3$ | 137–141 |
| O | H | H | $-CH_2-\text{(tetrahydrofuryl)}$ | 137–141 |
| O | H | H | $-CH_2C\equiv CH$ | 150–156 |

| B | $R_{10}$ | $R_9$ | R | mp° C. |
|---|---|---|---|---|
| S | H | H | H | 242–244 |
| S | H | Cl | H | 238–239 |
| S | H | Br | H | 226–227 |

-continued

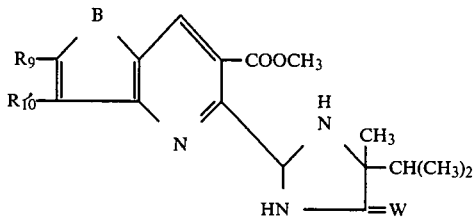

| B | R$_{10}$ | R$_9$ | R | mp° C. |
|---|---|---|---|---|
| S | H | H | —CH$_2$—furan | 156–157 |
| O | H | H | H | 214–223 |
| S | Cl | H | H | 266–267 |

EXAMPLE 35

Preparation of methyl 5-(4-isopropyl-4-methyl-5-oxo-2-imidazolidinyl)-furo[3,2-b]pyridine-6-carboxylate

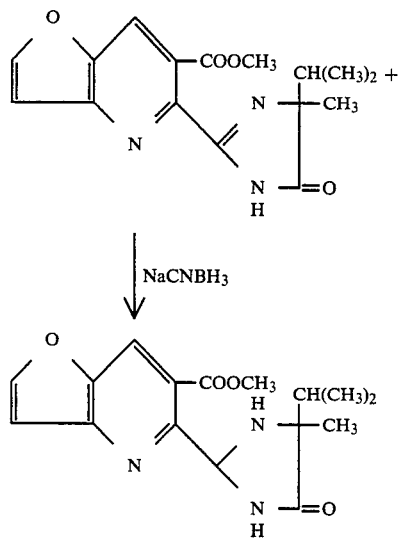

A solution of 22.1 mmol of methyl 5-(4-isopropyl-4-methyl-5-oxo-2-imidazolin-2-yl)furo[3,2-b]pyridine-6-carboxylate in methanol is cooled to 0° C. and a few drops of methyl orange indicator added. The solution is stirred and treated with 22.1 mmol of concentrated hydrochloric acid. The solution is then treated with 22.1 mmol of sodium cyanoborohydride, and the pH maintained at ~3 by the addition of 2N methanolic HCl, stirred overnight, cooled to 0° C. and the pH of the solution adjusted to about 0 with HCl to decompose residual NaCNBH$_3$. The pH is thereafter adjusted to 5–6 with 5N NaOH. The methanol is removed in vacuo and water added to dissolve inorganic salts. The mixture is extracted with CH$_2$Cl$_2$ and the extracts dried and concentrated to give the title compound.

Utilizing the above procedure with the appropriately substituted methyl 2-(2-imidazolin-2-yl)furo[3,2-pyridine-6-carboxylate yields the corresponding 2-(2-imidazolidinyl)furo[3,2-b]pyridine-6-carboxylate. Similarly, reaction of the appropriately substituted methyl 2-(2-imidazolin-2-yl)thieno[3,2-b]pyridine-6-carboxylate yields the corresponding methyl 2-(2-imidazolinyl)-thieno[3,2-b]pyridine-6-carboxylate. The reaction products are illustrated below:

Similarly, using the above procedure with the appropriately substituted methyl 2-(2-imidazolin-2-yl)dihydrofuro- or dihydrothieno[3,2-b]pyridine-6-carboxylate yields the corresponding substituted methyl 2-(2-imidazolidinyl)dihydrofuro- or dihydrothieno[3,2-b]pyridine-6-carboxylate. The reaction products are illustrated below:

| B | W | R$_9$ | R$_{10}$ | mp °C. |
|---|---|---|---|---|
| O | O | H | H | |
| S | S | H | H | |
| S | O | H | H | |
| O | S | H | H | |
| O | O | H | Cl | |
| S | S | H | Cl | |
| S | O | H | Cl | |
| O | S | H | Cl | |
| O | O | CH$_3$ | H | |
| S | S | CH$_3$ | H | |
| S | O | CH$_3$ | H | |
| O | S | CH$_3$ | H | |
| O | O | H | CH$_3$ | |
| S | S | H | CH$_3$ | |
| S | O | H | CH$_3$ | |
| O | S | H | CH$_3$ | |
| O | O | C$_2$H$_5$ | H | |
| S | S | C$_2$H$_5$ | H | |
| S | O | C$_2$H$_5$ | H | |
| O | S | C$_2$H$_5$ | H | |
| O | O | H | C$_2$H$_5$ | |
| S | S | H | C$_2$H$_5$ | |
| S | O | H | C$_2$H$_5$ | |
| O | S | H | C$_2$H$_5$ | |
| O | O | CH$_3$ | CH$_3$ | |
| S | S | CH$_3$ | CH$_3$ | |
| S | O | CH$_3$ | CH$_3$ | |
| O | S | CH$_3$ | CH$_3$ | |
| O | O | H | Br | |
| S | S | H | Br | |
| S | O | H | Br | |
| O | S | H | Br | |

EXAMPLE 36

Preparation of cis- and trans-methyl 6-(4-isopropyl-4-methyl-5-oxo-2-imidazolidinyl)-thieno[2,3-b]pyridine-5-carboxylates

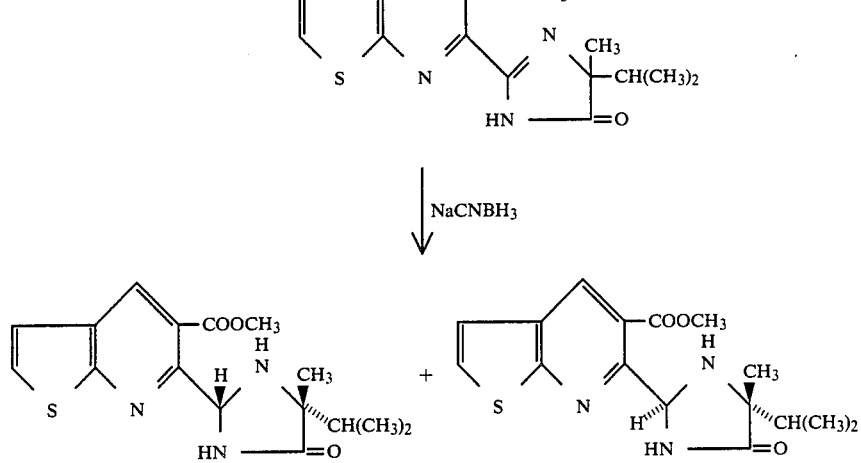

Using essentially the same procedure as described in Example 58 but substituting methyl 6-(4-isopropyl-4-methyl-5-oxo-2-imidazolin-2-yl)thieno[2,3-b]pyridine-5-carboxylate for methyl 5-(4-isopropyl-4-methyl-5-oxo)-2-imidazolin-2-yl)furo[3,2-b]pyridine-6-carboxylate yields the two products cis-methyl 6-(4-isopropyl-4-methyl-5-oxo-2-imidazolidinyl)thieno[3,2-b]pyridine-5-carboxylate mp 185°–186° C. and trans-methyl 6-(4-isopropyl-4-methyl-5-oxo-2-imidazolidinyl)thieno[2,3-b]pyridine-5-carboxylate mp 145°–148° C.

Utilizing the above procedure with the appropriately substituted methyl thieno-, dihydrothieno-, furo- or dihydrofuro[2,3-b]pyridine-5-carboxylate yields the reaction products illustrated below.

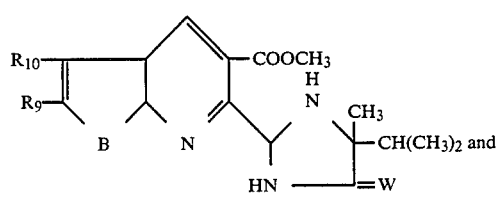

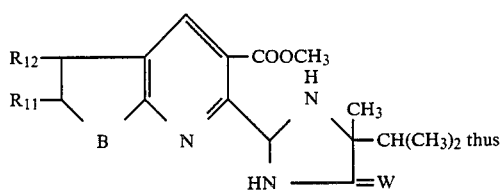

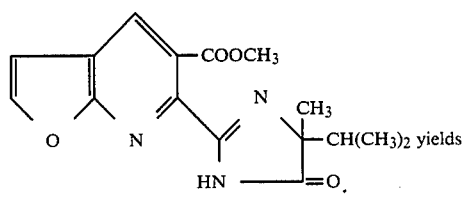

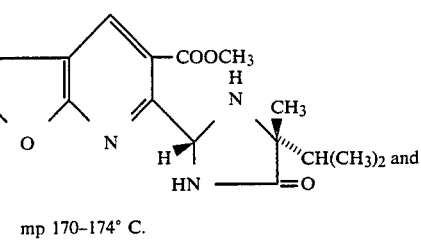

mp 170–174° C.

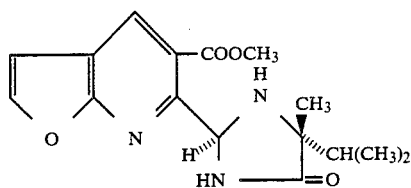

mp 166–169° C.

EXAMPLE 37

Preparation of trans-6-(4-isopropyl-4-methyl-5-oxo-2-imidazolidinyl)-thieno[2,3-b]pyridine-5-carboxylic acid

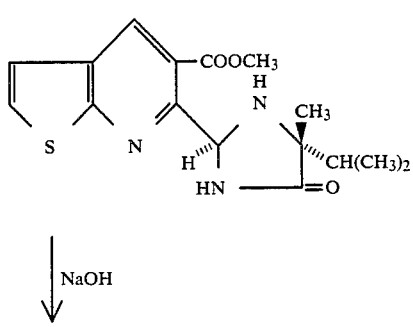

-continued

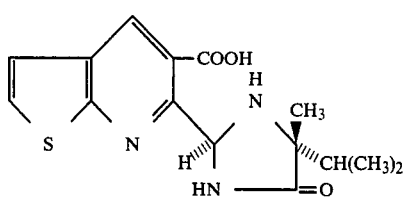

Using essentially the same conditions as those described in Example 32 but substituting trans-methyl 6-(4-isopropyl-4-methyl-5-oxo-2-imidazolidinyl)-thieno[2,3-b]pyridine-5-carboxylate for cis-methyl 6-(allyloxy)-2-(4-isopropyl-4-methyl-5-oxo-2-imidazolidinyl)nicotinate gives the product trans-6-(4-isopropyl-4-methyl-5-oxo-2-imidazolidinyl)thieno[2,3-b]pyridine-5-carboxylic acid, mp 225°–226° C. as a sesquihydrate.

Similarly, the furano analogs yield the corresponding imidazolidinones below:

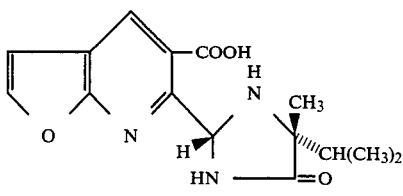

mp 210–218° C.

and

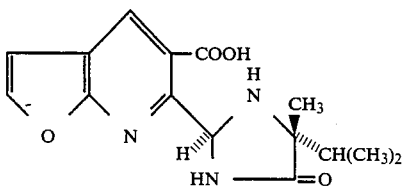

mp 176–178° C.

EXAMPLE 38

Preparation of diethyl 5-acetyl-1,6-dihydro-6-oxo-2,3-pyridinedicarboxylate

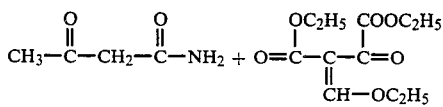

↓ Sodium acetate

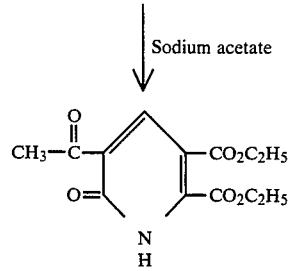

Sodium acetate (30 g, 0.37 mol) is added to a stirred mixture of diethyl(ethoxymethylene)oxalacetate (87 g, 0.36 mol) and acetoacetamide (36 g, 0.36 mol) in absolute ethanol (300 mL). After stirring the reaction mixture for 30 minutes, the ethanol is distilled off under reduced pressure, the residue acidified to pH 2 with dilute aqueous hydrochloric acid and the resulting solid filtered off. Crystallization from an ethanol-water mixture affords diethyl 5-acetyl-1,6-dihydro-6-oxo-2,3-pyridinedicarboxylate as crystals mp 200°–209° C.

EXAMPLE 39

Preparation of diethyl 5-(bromoacetyl)-1,6-dihydro-6-oxo-2,3-pyridinedicarboxylate

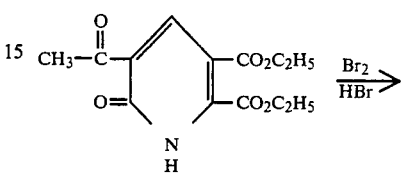

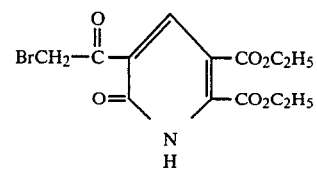

Bromine (8.0 g, 0.050 mol) in 48% HBr is added dropwise to a stirred solution of diethyl-5-acetyl-1,6-dihydro-6-oxo-2,3-pyridinecarboxylate (14.05 g, 0.05 mol) in 48% HBr (200 mL). Upon completion of this bromine addition the reaction mixture is poured onto ice (200 g) and the mixture is stirred until the ice has melted. The crude product is collected by filtration and crystallized twice from an ethyl acetate-hexane mixture (½) affording diethyl 5-(bromoacetyl)-1,6-dihydro-6-oxo-2,3-pyridinedicarboxylate with mp 141°–142° C.

EXAMPLE 40

Preparation of diethyl 5-(2-bromo-1-hydroxyethyl)-1,6-dihydro-6-oxo-2,3-pyridinedicarboxylate and diethyl 2,3-dihydro-3-hydroxy-furo[2,3-b]pyridine-5,6-dicarboxylate

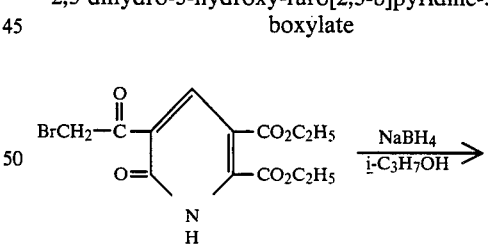

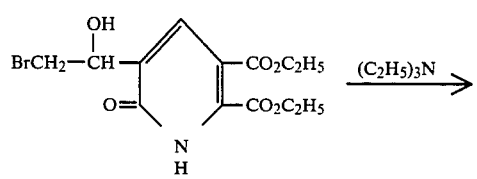

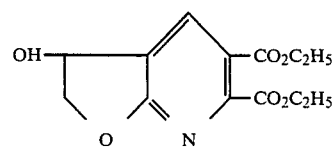

Sodium borohydride (2.54 g, 0.066 mol) is added in portions over a 30 minute period to a stirred suspension of diethyl 5-(bromoacetyl)-1,6-dihydro-6-oxo-2,3-pyridinedicarboxylate (57.2 g, 0.159 mol) at 10°-20° C. Upon completion of the sodium borohydride addition, the reaction mixture is stirred while attaining room temperature. Ice (100 g) is added and the mixture stirred until the ice has melted. The mixture is then concentrated in vacuo and the residue crystallized twice from an ethyl acetate-hexane mixture to give pure diethyl 5-(2-bromo-1-hydroxyethyl)-1,6-dihydro-6-oxo-2,3-pyridinedicarboxylate mp 134°-138° C. Stirring this compound with triethylamine (1.0 mL/g of solid) in methylene chloride for one hour, followed by washing the organic solution with dilute hydrochloric acid, water, brine and drying over anhydrous MgSO₄ yields the crude furo[2,3-b]pyridine as an oil upon removing the solvent in vacuo. Crystallization from a cyclohexane-toluene mixture affords pure diethyl 2,3-dihydro-3-hydroxy-furo[2,3-b]pyridine-5,6-dicarboxylate mp 73°-77° C.

EXAMPLE 41

Preparation of diethyl furo[2,3-b]pyridine-5,6-dicarboxylate

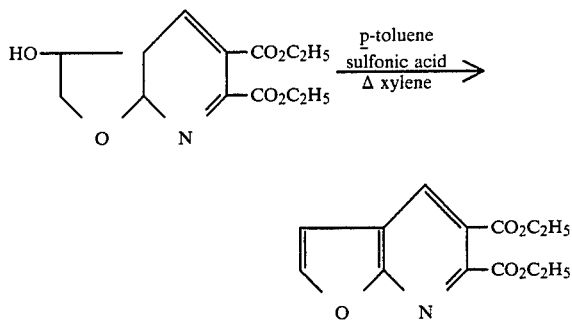

A xylene solution of the hydroxy-furo compound obtained in Example 61, (3.7 g) containing para-toluene sulfonic acid (0.01 g) is heated at reflux for two hours. The solution is cooled and the xylene solution decanted off. The residue is extracted with ether and the extracts combined with the xylene. Distillation of the solvents gives a yellow solid which is crystallized from a cyclohexane-toluene mixture to give pure diethyl furo[2,3-b]pyridine-5,6-dicarboxylate mp 66°-77° C.

EXAMPLE 42

Preparation of furo[2,3-b]pyridine-5,6-dicarboxylic acid

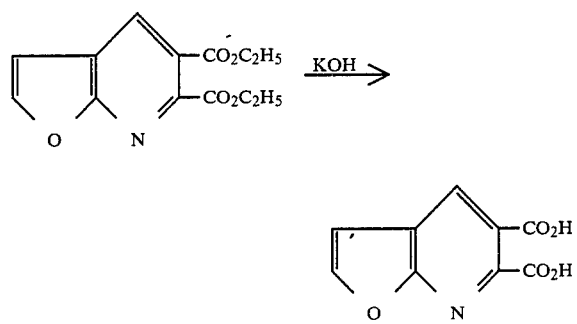

Potassium hydroxide (5.60 g, 85%, 0.087 mol) in water (5 mL) is added to a stirred suspension of diethyl furo[2,3-b]pyridine-5,6-dicarboxylate (9.3 g, 0.035 mol) in absolute ethanol (100 mL). The reaction mixture is heated at 60° C. for one hour, then cooled and anhydrous acetone added. The precipitate is filtered off, dried, suspended in dry acetone and treated with hydrogen chloride to adjust to a pH of 2. Crystallization of the isolated solids from an ethyl acetate-acetone mixture affords furo[2,3-b]pyridine-5,6-dicarboxylic acid mp 189°-192° C.

EXAMPLE 43

Preparation of furo[2,3-b]pyridine-5,6-dicarboxylic anhydride

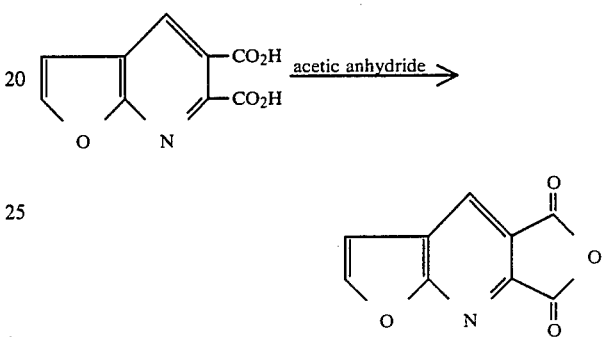

Furo[2,3-b]pyridine-5,6-dicarboxylic acid (6.7 g, 0.032 mol) is heated at 60° C. for 30 minutes in acetic anhydride (150 mL). The reaction mixture is cooled to room temperature and concentrated in vacuo and the residue triturated with cyclohexane-ether(5:1), filtered off and dried to give 5.35 g furo[2,3-b]pyridine-5,6-dicarboxylic acid anhydride.

EXAMPLE 44

Preparation of 6-[(1-carbamoyl-1,2-dimethylpropyl)carbamoyl]-furo[2,3-b]pyridine-5-carboxylic acid

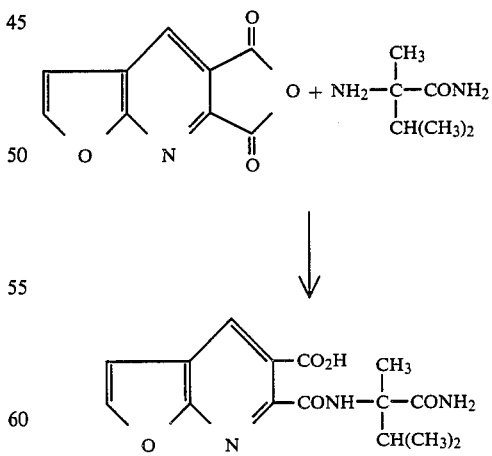

2-Amino-2,3-dimethylbutyramide (2.1 g, 0.016 mol) is added to a stirred suspension of furo[2,3-b]pyridine-5,6-dicarboxylic acid anhydride (3.0 g, 0.016 mol) in tetrahydrofuran (7.5 mL) and the mixture allowed to stir at room temperature for 16 hours. The reaction mixture is then stirred at 60° C. for one hour, cooled to room temperature, ether added, and the solid filtered off and dried to give 5 g of 6-[(1-carbamoyl-1,2-dimethylpropyl)carbamoyl]furo[2,3-b]pyridine-5-carboxylic acid mp 192°–196° C. (dec).

EXAMPLE 45

Preparation of 6-(4-isopropyl-4-methyl-5-oxo-2-imidazolin-2-yl)furo[2,3-b]pyridine-5-carboxylic acid

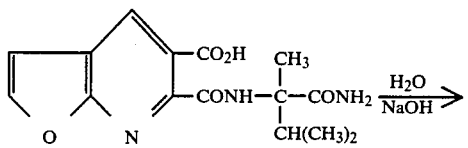

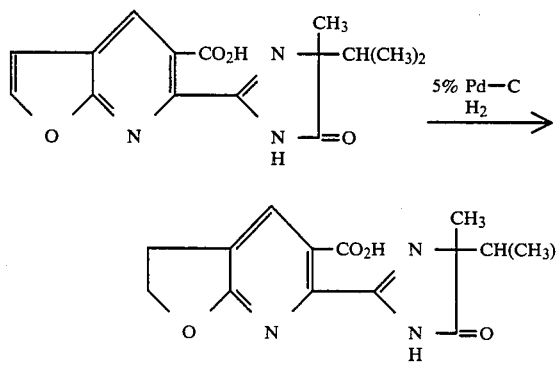

A solution containing 6-[(1-carbamoyl-1,2-dimethylpropyl)carbamoyl]furo[2,3-b]pyridine-5-carboxylic acid (3.8 g, 0.012 mol) in aqueous sodium hydroxide 2.4 g, 0.06 mol) in water (40 mL) is stirred at 65° C. for three hours. The reaction mixture is then heated at 75° C. for one hour, allowed to cool, poured into ice, acidified to pH 2–3 and the resulting solid filtered off and dried. Crystallization from an acetone-methanol mixture affords pure 6-(4-isopropyl-4-methyl-5-oxo-2-imidazolin-2-yl)furo[2,3-b]pyridine-5-carboxylic acid mp 237°–244° C.

EXAMPLE 46

Preparation of 2,3-dihydro-6-(4-isopropyl-4-methyl-5-oxo-2-imidazolin-2-yl)furo[2,3-b]pyridine-5-carboxylic acid A solution of 6-(4-isopropyl-4-methyl-5-oxo-2-imidazolin-2-yl)furo[2,3-b]pyridine-5-carboxylic acid (1.7 g 0.056 mol) and 1.0 g (0.0072 mol) potassium carbonate in 200 mL 9:1 ethanol:water is added to 100 mg 5% palladium on carbon catalyst in a 500 mL pressure bottle. The bottle is fitted to a Parr hydrogenation apparatus, pressurized to 30 psi, with hydrogen, then shaken at room temperature for 10 hours. The catalyst is removed by filtration through a sintered glass funnel, and the filtrate concentrated in vacuo to 10 mL. Acidification of the residue to pH 2 gives a white precipitate which is removed by filtration, washed with water and air dried to give 1.0 g (63%) of 2,3-dihydro-6-(4-isopropyl-4-methyl-5-oxo-2-imidazolin-2-yl)furo[2,3-b]pyridine-5-carboxylic acid as an off-white solid, mp 189°–192° C.

EXAMPLE 47

Preparation of 4-mercaptoacetyl buryronitrile

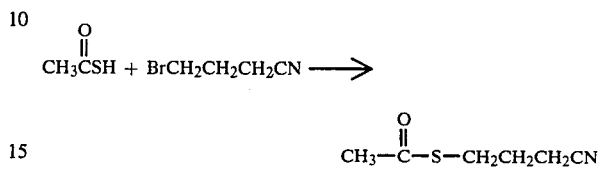

Thiolacetic acid (49 mL, 0.69 mol) is added to potassium carbonate (93.4 g, 0.68 mol) dissolved in water (150 mL). Ethanol (260 mL) is added and then 4-bromobutyronitrile is added at 15° to 28° C. and the reaction mixture stirred at room temperature for 16 hours. The resulting inorganic solids are filtered off and the filtrate extracted with toluene. The organic layer is separated, dried over anhydrous Na$_2$SO$_4$ and concentrated to give the desired 4-mercaptoacetyl butyronitrile as a yellow oil.

EXAMPLE 48

Preparation of dihydrothiophenimine hydrochloride

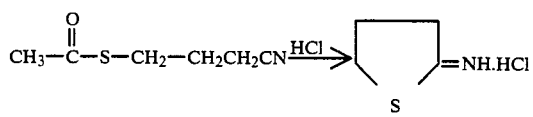

Hydrogen chloride is introduced to a cooled solution of the nitrile in methanol (220 mL) for one hour and the mixture then stirred at room temperature for 16 hours. The resulting product is filtered off, washed with ether and dried to give 55.38 g of dihydrothiophenimine hydrochloride, mp 189°–195° C.

EXAMPLE 49

Preparation of dimethyl [(tetrahydro-2-thienylidene)-amino]fumarate (and maleate)acid

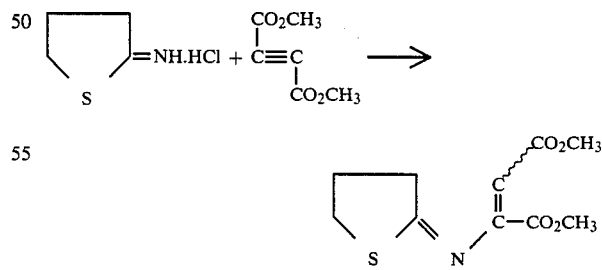

Dimethylacetylenedicarboxylate (0.45 mL, 0.037 mol) is added to a stirred solution of dihydrothiophenimine hydrochloride (0.5 g, 0.0036 mol) in methanol (60 mL) containing sodium acetate (0.3 g, 0.0036 mol) under an inert N$_2$ atmosphere at −15° C. After stirring for 16 hours at room temperature, the solvent is removed on a rotary evaporator and the resulting mixture separated by column chromatography on silica gel eluting with a methylene chloride-acetonitrile mixture (19:1) yielding 0.68 g (78% yield) of the desired mixed isomeric acid esters as a yellow oil.

EXAMPLE 50

Preparation of dimethyl 2,3-dihydrothieno[2,3-b]-pyridine-5,6-dicarboxylate

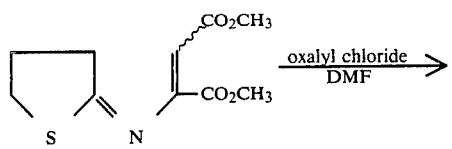

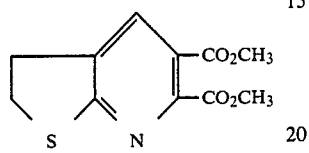

A vilsmeier reagent is prepared by adding oxalyl chloride (0.25 mL, 0.0028 mol) to a stirred solution of DMF (0.22 mL, 0.0028 mol) in 1,2-dichloroethane (50 mL) at room temperature in an inert $N_2$ atmosphere. A 1,2-dichloroethane (50 mL) solution of dimethyl[(tetrahydro-2-thienylidine)amino]fumarate (and maleate) (0.0028 mol) is added to the Vilsmeier reagent and the reaction mixture heated at reflux for four hours. The reaction mixture is quenched with water, made basic with sodium bicarbonate and the organic layer separated and dried over anhydrous $Na_2SO_4$.

The solvent is removed in vacuo and the residue purified by column chromatography on silica gel, eluting with a methylene chloride-acetonitrile mixture (19:1). Crystallization from toluene-hexane affords dimethyl 2,3-dihydrothieno[2,3-b]pyridine-5,6-dicarboxylate as a white solid with mp 102°–103.5° C.

EXAMPLE 51

Preparation of 2-isopropyl-2-methyl-5H-imidazo[1',2':1,2]-pyrrolo[3,4-b]pyridine-3(2H),5-dione

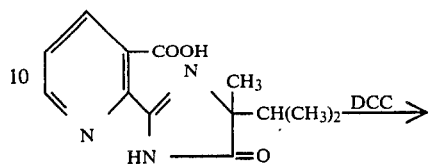

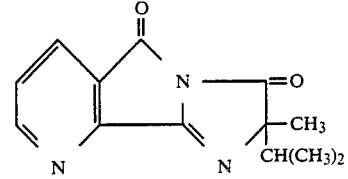

To a solution containing 50.9 g of dicyclohexylcarbodiimide in 600 mL of dry methylene chloride is added, while stirring, 60 g of the acid at such a rate that the temperature does not exceed 32° C. After stirring at room temperature for two and one-half hours, the mixture is filtered and the filtrate concentrated to give a white solid. This solid is recrystallized from methylene chloride to give 57.4 g of the dione, mp 125°–128.5° C. The analytically pure dione melts at 132°–134° C. The procedure illustrated in European Patent Application No. 0,041,023, published Dec. 16, 1981.

Using essentially the same procedure but substituting the appropriate acid for 2-(4-isopropyl-4-methyl-5-oxo-2-imidazolin-2-yl)nicotinic acid, the following imidazopyrrolopyridine-3,5-diones are prepared.

| W | X | Y | Z | R$_1$ | R$_2$ | mp °C. |
|---|---|---|---|---|---|---|
| O | H | H | C$_3$H$_7$ | CH$_3$ | CH(CH$_3$)$_2$ | 98.5–101.0 |
| O | H | H | CH(CH$_3$)$_2$ | | CH(CH$_3$)$_2$ | 100.0–105.0 |
| O | H | CH(CH$_3$)$_2$ | H | CH$_3$ | CH(CH$_3$)$_2$ | 128.0–137.0 |
| O | H | C$_2$H$_5$ | H | CH$_3$ | CH(CH$_3$)$_2$ | 126.0–131.0 |
| O | H | H | C$_2$H$_5$ | CH$_3$ | CH(CH$_3$)$_2$ | 148.0–152.5 |
| O | H | OCH(CH$_3$)$_2$ | H | CH$_3$ | CH(CH$_3$)$_2$ | 157.0–161.0 |
| S | H | H | H | CH$_3$ | CH(CH$_3$)$_2$ | 206.0–209.0 |
| S | H | CH$_3$ | H | CH$_3$ | CH(CH$_3$)$_2$ | |
| S | H | C$_2$H$_5$ | H | CH$_3$ | CH(CH$_3$)$_2$ | |
| S | H | —CH=CH—CH=CH— | | CH$_3$ | CH(CH$_3$)$_2$ | 211.0–213.0 |
| S | H | —CH=CH—S— | | CH$_3$ | CH(CH$_3$)$_2$ | |
| S | H | —CH=CH—O— | | CH$_3$ | CH(CH$_3$)$_2$ | |
| O | H | OCH$_3$ | H | CH$_3$ | CH(CH$_3$)$_2$ | 165.0–172.0 |
| O | H | H | OCH$_2$CH=CH$_2$ | CH$_3$ | CH(CH$_3$)$_2$ | 89.0–93.0 |
| O | H | H | CH$_3$ | CH$_3$ | CH(CH$_3$)$_2$ | 138.0–141.0 |
| O | H | —CH—CH—O— | | CH$_3$ | CH(CH$_3$)$_2$ | 193.0–205.0 |

EXAMPLE 52

Preparation of
3-isopropyl-3-methyl-5H-imidazo[1',2':1,2]-pyrrolo[3,4-b]pyridine-2(5H),5-dione

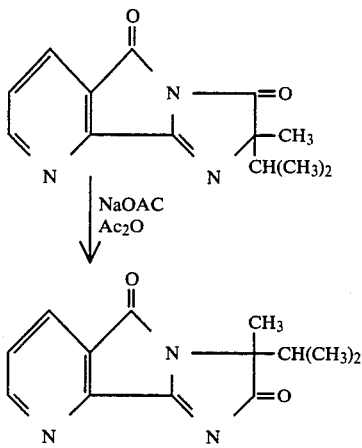

To a solution containing 0.5 g 2-isopropyl-2-methyl-5H-imidazo[1',2':1,2]pyrrolo[3,4-b]pyridine-3(2H), 5-dione in 5 mL acetic anhydride is added 50 mg sodium acetate and the mixture heated at reflux for two hours. The solvent is removed and the product extracted into ether to give the rearranged dione, 3-isopropyl-3-methyl-5H-imidazo[1',2':1,2]pyrrolo[3,4-b]pyridine-2(3H)5-dione mp 107°–115° C.

EXAMPLE 52-A

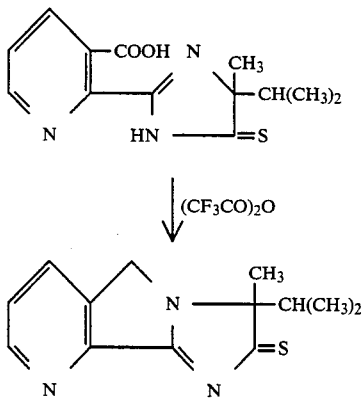

To a solution of the acid in 200 mL toluene and 100 mL $CH_2Cl_2$ under nitrogen is added with stirring at −60° C. during 0.5 hours, 1.9 g trifluoroacetic anhydride dissolved in 18 mL toluene and 7 mL $CH_2Cl_2$. After this reaction, 500 mL hexane is added and the mixture concentrated in vacuo to give a dark green solid. NMR spectroscopy showed this to consist of 80% of the desired 2,5-dione and 20% of 3,5-dione.

The 2,5-dione was characterized as its water addition product, mp 162°–165° C. with structure

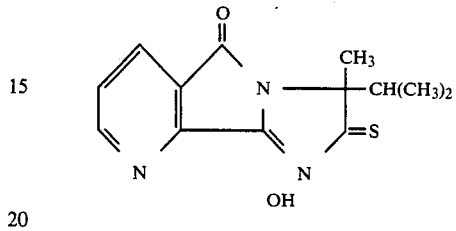

Using essentially this procedure or those described in Examples 51, 52 and 52-A and starting with the appropriate acid or 3,5-dione, the following 2,5-diones are obtained.

| W | X | Y | Z | $R_1$ | $R_2$ | mp °C. |
|---|---|---|---|---|---|---|
| O | H | H | $C_3H_7$ | $CH_3$ | $CH(CH_3)_2$ | |
| O | H | H | $CH(CH_3)_2$ | | $CH(CH_3)_2$ | |
| O | H | $CH(CH_3)_2$ | H | $CH_3$ | $CH(CH_3)_2$ | |
| O | H | $C_2H_5$ | H | $CH_3$ | $CH(CH_3)_2$ | |
| O | H | H | $C_2H_5$ | $CH_3$ | $CH(CH_3)_2$ | |
| O | H | $OCH(CH_3)_2$ | H | $CH_3$ | $CH(CH_3)_2$ | |
| S | H | H | H | $CH_3$ | $CH(CH_3)_2$ | |
| S | H | $CH_3$ | H | $CH_3$ | $CH(CH_3)_2$ | |
| S | H | $C_2H_5$ | H | $CH_3$ | $CH(CH_3)_2$ | |
| S | H | —CH=CH—CH=CH— | | $CH_3$ | $CH(CH_3)_2$ | |
| S | H | —CH=CH—S— | | $CH_3$ | $CH(CH_3)_2$ | |
| S | H | —CH=CH—O— | | $CH_3$ | $CH(CH_3)_2$ | |
| O | H | H | $OCH_3$ | $CH_3$ | $CH(CH_3)_2$ | 147.0–147.5 |
| O | H | $OCH_3$ | H | $CH_3$ | $CH(CH_3)_2$ | |
| O | H | $CH_3$ | H | $CH_3$ | $CH(CH_3)_2$ | |

The procedures of Examples 51, 52 and 52-A may be graphically illustrated as follows:

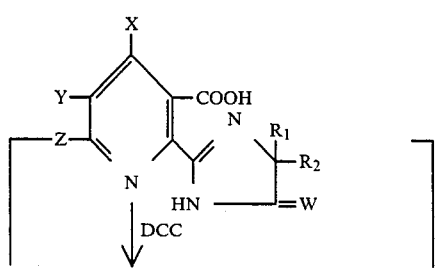

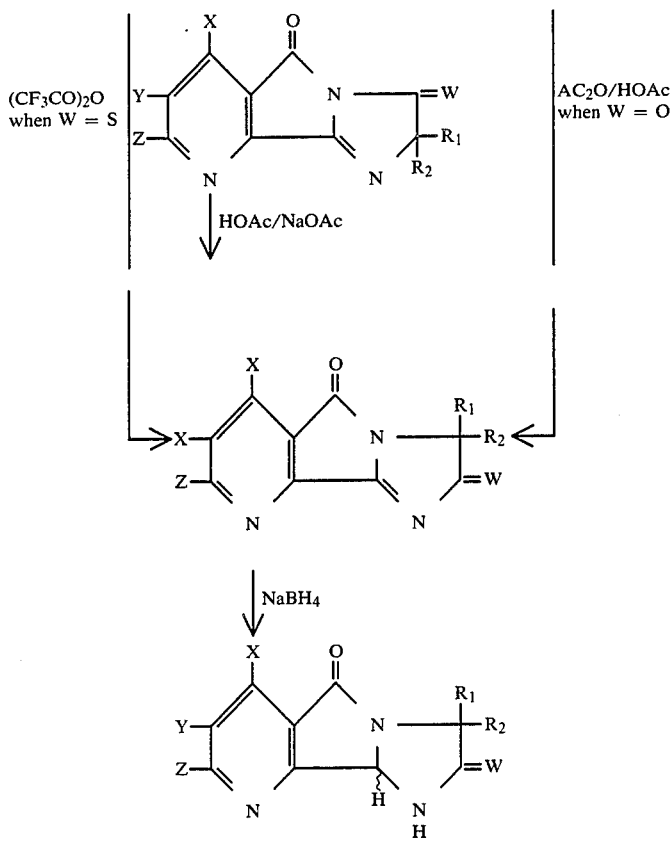

EXAMPLE 53

Postemergence herbicidal evaluation of test compounds

The postemergence herbicidal activity of the compounds of the present invention is demonstrated by the following tests, wherein a variety of monocotyledonous and dicotyledonous plants are treated with test compounds dispersed in aqueous acetone mixtures. In the tests, seedling plants are grown in jiffy flats for about two weeks. The test compounds are dispersed in 50/50 acetone/water mixtures containing 0.5% TWEEN ® 20, a polyoxyethylene sorbitan monolaurate surfactant of Atlas Chemical Industries, in sufficient quantities to provide the equivalent of about .016 to 10.0 kg per hectare of active compound when applied to the plants through a spray nozzle operating at 40 psig for a predetermined time. After spraying, the plants are placed on greenhouse benches and are cared for in the usual manner, commensurate with conventional greenhouse practices. From four to five weeks after treatment, the seedling plants, are examined and rated according to the rating system provided below. The data obtained are recorded in Table V below.

| Rating System | % Difference in Growth from the Check |
|---|---|
| 0 - No Effect | 0 |
| 1 - Possible effect | 1–10 |
| 2 - Slight effect | 11–25 |
| 3 - Moderate effect | 26–40 |
| 5 - Definite injury | 41–60 |
| 6 - Herbicidal effect | 61–75 |
| 7 - Good herbicidal effect | 76–90 |
| 8 - Approaching complete kill | 91–99 |
| 9 - Complete kill | 100 |
| 4 - Abnormal growth, that is, a definite physiological malformation but with an over-all effect less than a 5 on the rating scale. | |

In most cases the data are for a single test, but in several instances, they are average values obtained from more than one test.

| Plant Species Used | |
|---|---|
| Barnyardgrass | (*Echinochloa crusgalli*) |
| Green foxtail | (*Setaria viridis*) |
| Purple Nutsedge | (*Cyperus rotundus* L.) |
| Ragweed | (*Ambrosia artemisiifolia*, L.) |
| Quackgrass | (*Agropyron repens*) |
| Field Bindweed | (*Convolvulus arvensis* L.) |
| Morningglory | (*Ipomoea purpurea*) |
| Velvetleaf | (*Abutilon theophrasti*) |
| Cotton | (*Gossypium hirsutum*, L.) |
| Corn | (*Zea mays*) |
| Soybean | (*Glycine max*) Bragg |
| Soybean | (*Glycine max*) Williams |
| Wheat | (*Triticum aestivum*) |
| Rice | (*Oryza sativa*) Nato |

TABLE V

POST-EMERGENCE TESTS - RATES IN KG/HA

| Compound | RATE | BARN-YARD GR | FOX-TAIL SP | P NUT-SEDGE | QUACK-GRASS | FLD BIND-WD | MRN-GLRY SP | RAG WEED | VEL-VET LEAF | CORN FIELD | COT-TON | RICE, NATO | SOY-BEAN BR | SOY-BEAN WI | S WHEAT ER |
|---|---|---|---|---|---|---|---|---|---|---|---|---|---|---|---|
| 3α-Ethyl-1,9bα(and β)-di-hydro-3-methyl-5H—imidazo[1′:2′:1,2]pyrrolo[3,4-b]pyridine-2(3H),5-dione | 10.000 | 7.0 | | 0.0 | | | 2.0 | 1.0 | 8.0 | 0.0 | 0.0 | 4.0 | | 0.0 | 9.0 |
| | 1.000 | 0.0 | | 0.0 | | | 4.0 | 0.0 | 7.0 | 0.0 | 0.0 | 0.0 | | 0.0 | 9.0 |
| | .500 | 0.0 | | 0.0 | | | 8.0 | 0.0 | 7.0 | 0.0 | 0.0 | 0.0 | | 0.0 | 9.0 |
| | .250 | 0.0 | | 0.0 | | | 6.0 | 0.0 | 7.0 | 0.0 | 0.0 | 0.0 | | 0.0 | 8.5 |
| | .125 | 0.0 | | 0.0 | | | 1.0 | 0.0 | 6.0 | 0.0 | 0.0 | 0.0 | | 0.0 | 8.0 |
| | .063 | 0.0 | | 0.0 | | | 4.0 | 0.0 | 6.0 | 0.0 | 0.0 | 0.0 | | 0.0 | 6.0 |
| 1,9bα(and β)-dihydro-3α-isopropyl-3-methyl-5H—imidazo[1′,2′:1,2]pyrrolo[3,4-b]pyridine-2(3H),5-dione | 2.000 | | | | | | | | | 9.0 | 9.0 | 9.0 | | 9.0 | 9.0 |
| | 1.000 | 9.0 | | 8.0 | 9.0 | 9.0 | 9.0 | 9.0 | 9.0 | 8.0 | 9.0 | 7.5 | | 8.5 | 9.0 |
| | .500 | 9.0 | | 7.0 | 9.0 | 9.0 | 9.0 | 8.0 | 9.0 | 7.5 | 9.0 | 5.0* | | 8.5 | 9.0 |
| | .250 | 8.0 | | 2.0 | 8.0 | 9.0 | 9.0 | 8.0 | 9.0 | 5.0 | 9.0 | 5.0* | | 8.0 | 8.5 |
| | .125 | 2.0 | | 0.0 | 2.0 | 9.0 | 8.0 | 8.0 | 9.0 | 1.5 | 8.0 | 4.0* | | 8.0 | 8.0 |
| | .063 | 1.0 | | 0.0 | 2.0 | 9.0 | 7.0 | 1.0 | 8.0 | 0.5 | 7.0 | 3.0* | | 6.5 | 6.0 |
| | .032 | 0.0 | | 0.0 | | 3.0 | 4.0 | 0.0 | 5.0 | 0.0 | 3.0 | 0.0 | | 1.0 | 1.0 |
| 1,9bβ-Dihydro-3α-isopropyl-3,7-dimethyl-5H—imidazo[1′:1,2]pyrrolo[3,4-b]pyridine-2(3H),5-dione | 1.000 | 9.0 | 9.0 | 8.0 | 9.0 | 8.0 | 8.0 | 9.0 | 9.0 | 2.0 | 7.0 | 9.0 | 4.0 | 3.0 | 7.0 |
| | .500 | 9.0 | 9.0 | 8.0 | | 8.0 | 7.0 | 8.0 | 9.0 | 2.0 | 7.0 | 9.0 | 2.0 | 2.0 | 3.0 |
| | .250 | 9.0 | 9.0 | 8.0 | 8.0 | 8.0 | 4.0 | 8.0 | 8.0 | 1.0 | 3.0 | 7.0 | 2.0 | 2.0 | 2.0 |
| | .125 | 8.0 | 8.0 | 4.0 | 4.0 | 6.0 | 1.0 | 8.0 | 6.0 | 1.0 | | 7.0 | 2.0 | 1.0 | 2.0 |
| | .063 | 4.0 | 8.0 | 1.0 | 2.0 | 3.0 | 0.0 | 6.0 | 6.0 | 1.0 | 2.0 | 5.0 | 1.0 | 0.0 | 1.0 |
| | .032 | 0.0 | 4.0 | 0.0 | 0.0 | 0.0 | 0.0 | 4.0 | 2.0 | 1.0 | 2.0 | 3.0 | 1.0 | 0.0 | 1.0 |
| (R)-(+)-1,9bα-Dihydro-3β-isopropyl-3-methyl-5H—imidazo[1′:2′:1,2]pyrrolo[3,4-b]pyridine-2(3H),5-dione | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .500 | 9.0 | 9.0 | 9.0 | 9.0 | 9.0 | 9.0 | 9.0 | 9.0 | 9.0 | 9.0 | 8.0 | 9.0 | 9.0 | 9.0 |
| | .250 | 9.0 | 9.0 | 9.0 | 9.0 | 9.0 | 9.0 | 9.0 | 8.0 | 8.0 | 9.0 | 7.0 | 9.0 | 9.0 | 9.0 |
| | .125 | 8.0 | 9.0 | 8.0 | 9.0 | 8.0 | 9.0 | 8.0 | 7.0 | 8.0 | 8.0 | 6.0 | 8.0 | 8.0 | 9.0 |
| | .063 | 8.0 | 8.0 | 7.0 | 8.0 | 7.0 | 9.0 | 7.0 | 6.0 | 8.0 | 8.0 | 4.0 | 8.0 | 8.0 | 8.0 |
| | .032 | 7.0 | 8.0 | 6.0 | 8.0 | 8.0 | 9.0 | 9.0 | 2.0 | 2.0 | 8.0 | 8.0 | 9.0 | 8.0 | 8.0 |
| (±)-1,9bβ-Dihydro-3α-isopropyl-3-methyl-5H—imidazo[1′:2′:1,2]pyrrolo[3,4-b]pyridine-2(3H),5-dione | 1.000 | 9.0 | 9.0 | 9.0 | 9.0 | 9.0 | 9.0 | 9.0 | 9.0 | 9.0 | 9.0 | 8.0 | 9.0 | 8.0 | 9.0 |
| | .500 | 9.0 | 9.0 | 8.0 | 9.0 | 9.0 | 8.0 | 9.0 | 9.0 | 9.0 | 9.0 | 9.0 | 8.0 | 8.0 | 9.0 |
| | .250 | 9.0 | 9.0 | 8.0 | 4.0 | 9.0 | 9.0 | 9.0 | 8.0 | 9.0 | 8.0 | 8.0 | 9.0 | 8.0 | 9.0 |
| | .125 | 8.0 | 8.0 | 7.0 | 4.0 | 8.0 | 7.0 | 9.0 | 8.0 | 8.0 | 7.0 | 5.0 | 8.0 | 8.0 | 8.0 |
| | .063 | 8.0 | 8.0 | 6.0 | 3.0 | 5.0 | 7.0 | 8.0 | 8.0 | 8.0 | 7.0 | 4.0 | 8.0 | 8.0 | 8.0 |
| | .032 | 6.0 | 4.0 | 2.0 | 0.0 | 0.0 | 2.0 | 3.0 | 7.0 | 3.0 | 6.0 | 2.0 | 7.0 | 6.0 | 6.0 |
| 1,9bβ-Dihydro-3α-isopropyl-3,8-dimethyl-5H—imidazo[1′:2′:1,2]pyrrolo[3,4-b]pyridine-2(3H),5-dione | 1.000 | 9.0 | 9.0 | 8.0 | 9.0 | 9.0 | 8.0 | 9.0 | 7.0 | 2.0 | 8.0 | 9.0 | 7.0 | 4.0 | 9.0 |
| | .500 | 9.0 | 9.0 | 8.0 | 9.0 | 8.0 | 7.0 | 8.0 | 7.0 | 7.0 | 8.0 | 9.0 | 6.0 | 3.0 | 8.0 |
| | .250 | 9.0 | 9.0 | 8.0 | 4.0 | 7.0 | 7.0 | 8.0 | 8.0 | 5.0 | 8.0 | 9.0 | 3.0 | 3.0 | 8.0 |
| | .125 | 8.0 | 9.0 | 8.0 | 4.0 | 5.0 | 2.0 | 6.0 | 3.0 | 3.0 | 7.0 | 5.0 | 3.0 | 3.0 | 3.0 |
| | .063 | 8.0 | 9.0 | 7.0 | 3.0 | 2.0 | 1.0 | 4.0 | 1.0 | 1.0 | 6.0 | 4.0 | 2.0 | 2.0 | 4.0 |
| | .032 | 4.0 | 9.0 | 4.0 | 3.0 | 0.0 | 0.0 | 2.0 | 0.0 | 0.0 | 6.0 | 2.0 | 2.0 | 2.0 | 2.0 |
| 8-(Allyloxy)-1,9bβ-dihydro-3α-isopropyl-3-methyl-5H—imidazo[1′:2′:1,2]pyrrolo[3,4-b]pyridine-2(3H),5-dione | 1.000 | 0.0 | 4.0 | 0.0 | 0.0 | 0.0 | 0.0 | 2.0 | 0.0 | 2.0 | 2.0 | 4.0 | 2.0 | 2.0 | 2.0 |
| 1,9bα-Dihydro-3α-isopropyl-3-methyl-5H—imidazo[1′:2′:1,2]pyrrolo[3,4-b]pyridine-2(3H),5-dione | 1.000 | 9.0 | 9.0 | 7.0 | | 9.0 | 9.0 | 9.0 | 9.0 | 7.0 | 8.0 | 6.0 | 9.0 | 8.0 | 9.0 |
| | .500 | 9.0 | 9.0 | 7.0 | | 8.0 | 9.0 | 9.0 | 8.0 | 7.0 | 8.0 | 6.0 | 8.0 | 8.0 | 9.0 |
| | .250 | 9.0 | 9.0 | 4.0 | | 8.0 | 9.0 | 8.0 | 8.0 | 7.0 | 8.0 | 5.0 | 8.0 | 8.0 | 9.0 |
| | .125 | 8.0 | 9.0 | 2.0 | | 8.0 | 9.0 | 8.0 | 8.0 | 7.0 | 6.0 | 3.0 | 6.0 | 7.0 | 9.0 |
| | .063 | 9.0 | 9.0 | 2.0 | | 8.0 | 9.0 | 6.0 | 8.0 | 7.0 | 7.0 | 3.0 | 7.0 | 7.0 | 8.0 |
| | .032 | 8.0 | 9.0 | 0.0 | | 8.0 | 8.0 | 8.5 | 8.0 | 3.0 | 7.0 | 2.0 | 7.0 | 6.0 | 8.0 |
| 7-Ethyl-1,9bα(and β)-dihydro- | 1.000 | 9.0 | 9.0 | 4.0 | 8.0 | 9.0 | 5.5 | 8.5 | 8.0 | 0.5 | 3.0 | 6.0 | 0.0 | 0.0 | 2.0 |

TABLE V-continued

POST-EMERGENCE TESTS - RATES IN KG/HA

| Compound | RATE | BARN-YARD GR | FOX-TAIL SP | P NUT-SEDGE | QUACK-GRASS | FLD BIND-WD | MRN-GLRY SP | RAG WEED | VEL-VET LEAF | CORN FIELD | COT-TON | RICE, NATO | SOY-BEAN BR | SOY-BEAN WI | S WHEAT ER |
|---|---|---|---|---|---|---|---|---|---|---|---|---|---|---|---|
| 3α-isopropyl-3-methyl-5H—imidazo[1′,2′:1,2]pyrrolo[3,4-b]pyridine-2(3H),5-dione | .500 | 9.0 | 9.0 | 1.5 | 8.0 | 9.0 | 4.0 | 8.0 | 3.5 | 0.5 | 2.0 | 6.0 | 0.0 | 0.0 | 1.0 |
| | .250 | 8.5 | 7.0 | 0.0 | 2.0 | 6.0 | 3.0 | 5.0 | 3.0 | 0.5 | 1.0 | 6.0 | 0.0 | 0.0 | 1.0 |
| | .125 | 5.5 | 4.0 | 0.0 | 2.0 | 2.0 | 2.0 | 2.0 | 1.5 | 0.5 | 0.0 | 4.0 | 0.0 | 0.0 | 0.0 |
| | .063 | 1.5 | 1.0 | 0.0 | 2.0 | 1.0 | 0.0 | 0.0 | 0.0 | 0.5 | 0.0 | 3.0 | 0.0 | 0.0 | 0.0 |
| | .032 | 1.0 | 0.0 | 0.0 | 0.0 | 1.0 | 0.0 | 0.0 | 0.0 | 0.5 | 0.0 | 2.0 | 0.0 | 0.0 | 0.0 |
| 1,9bβ-Dihydro-3α-isopropyl-8-methoxy-3-methyl-5H—imidazo[1′,2′:1,2]pyrrolo[3,4-b]pyridine-2(3H),5-dione | 1.000 | 8.0 | 9.0 | 8.0 | 8.0 | 9.0 | 8.0 | 8.0 | 2.0 | 2.0 | 7.0 | 8.0 | 4.0 | 4.0 | 2.0 |
| | .500 | 8.0 | 7.0 | 7.0 | 3.0 | 6.0 | 7.0 | 6.0 | 0.0 | 2.0 | 5.0 | 7.0 | 3.0 | 3.0 | 2.0 |
| | .250 | 4.0 | 5.0 | 7.0 | 2.0 | 5.0 | 7.0 | 2.0 | 0.0 | 1.0 | 2.0 | 6.0 | 3.0 | 2.0 | 0.0 |
| | .125 | 2.0 | 3.0 | 2.0 | 0.0 | 2.0 | 7.0 | 0.0 | 0.0 | 1.0 | 2.0 | 5.0 | 3.0 | 2.0 | 0.0 |
| | .063 | 1.0 | 1.0 | 1.0 | 0.0 | 2.0 | 3.0 | 0.0 | 0.0 | 1.0 | 1.0 | 5.0 | 2.0 | 1.0 | 0.0 |
| | .032 | 1.0 | 0.0 | 0.0 | 0.0 | 0.0 | 0.0 | 0.0 | 0.0 | 1.0 | 1.0 | 2.0 | 0.0 | 0.0 | 0.0 |
| 1,9bα-Dihydro-3α-isopropyl-3-methyl-5H—imidazo[1′,2′:1,2]pyrrolo[3,4-b]quinoline-2(3H),5-dione | 1.000 | 3.0 | 4.0 | 2.0 | 0.0 | 0.0 | 2.0 | 0.0 | 0.0 | 0.0 | 6.0 | 4.0 | 0.0 | 0.0 | 0.0 |
| | .500 | 2.0 | 2.0 | 0.0 | 0.0 | 0.0 | 0.0 | 0.0 | 0.0 | 0.0 | 6.0 | 2.0 | 0.0 | 0.0 | 0.0 |
| | .250 | 1.0 | 2.0 | 0.0 | 0.0 | 0.0 | 0.0 | 0.0 | 0.0 | 0.0 | 4.0 | 0.0 | 0.0 | 0.0 | 0.0 |
| | .125 | 0.0 | 0.0 | 0.0 | 0.0 | 0.0 | 0.0 | 0.0 | 0.0 | 0.0 | 3.0 | 0.0 | 0.0 | 0.0 | 0.0 |
| | .063 | 0.0 | 0.0 | 0.0 | 0.0 | 0.0 | 0.0 | 0.0 | 0.0 | 0.0 | 3.0 | 0.0 | 0.0 | 0.0 | 0.0 |
| | .032 | 0.0 | 0.0 | 0.0 | 0.0 | 0.0 | 0.0 | 0.0 | 0.0 | 0.0 | 2.0 | 0.0 | 0.0 | 0.0 | 0.0 |
| 8-Chloro-1,9β-dihydro-3α-isopropyl-3-methyl-5H—imidazo[1′,2′:1,2]pyrrolo[3,4-b]pyridine-2(3H),5-dione | 1.000 | 4.0 | 9.0 | 7.0 | 9.0 | 4.0 | 7.0 | 9.0 | 4.0 | 2.0 | 4.0 | 5.0 | 3.0 | 3.0 | 5.0 |
| | .500 | 2.0 | 8.0 | 3.0 | 6.0 | 1.0 | 5.0 | 8.0 | 2.0 | 2.0 | 2.0 | 4.0 | 2.0 | 2.0 | 4.0 |
| | .250 | 1.0 | 6.0 | 3.0 | 6.0 | 1.0 | 3.0 | 8.0 | 0.0 | 1.0 | 1.0 | 2.0 | 1.0 | 2.0 | 2.0 |
| | .125 | 0.0 | 6.0 | 1.0 | 2.0 | 0.0 | 1.0 | 7.0 | 0.0 | 0.0 | 0.0 | 1.0 | 1.0 | 1.0 | 1.0 |
| | .063 | 0.0 | 0.0 | 0.0 | 1.0 | 0.0 | 0.0 | 4.0 | 0.0 | 0.0 | 0.0 | 1.0 | 0.0 | 0.0 | 0.0 |
| | .032 | 0.0 | 0.0 | 0.0 | 0.0 | 0.0 | 0.0 | 0.0 | 0.0 | 0.0 | 0.0 | 1.0 | 0.0 | 0.0 | 0.0 |

EXAMPLE 54

Preemergence herbicidal evaluation of test compounds

The preemergence herbicidal activity of the compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.016 to 10.0 kg per hectare of test compound per cup. The treated cups are then placed on greenhouse benches, watered and cared for in accordance with conventional greenhouse procedures. From four to five weeks after treatment, the tests are terminated and each cup is examined and rated according to the rating system set forth above. The herbicidal proficiency of the active ingredients of the present invention is evident from the test results which are recorded in Table VI below. Where more than one test is involved for a given compound, the data are averaged.

TABLE VI

PRE-EMERGENCE TESTS - RATES IN KG/HA

| Compound | RATE | BARN-YARDGR | FOX-TAIL SP | P NUT SEDGE | QUACK GRASS | FLD BINDWD | MRNGLRY SP | RAG-WEED | VELVET-LEAF | CORN FIELD | COT-TON | RICE, NATO | SOY-BEAN BR | SOY-BEAN WI | S WHEAT ER |
|---|---|---|---|---|---|---|---|---|---|---|---|---|---|---|---|
| 3α-Ethyl-1,9bα(and β)-dihydro-3-methyl-5H—imidazo[1′:2′:1,2]pyrrolo[3,4-b]pyridine-2(3H),5-dione | 10.000 | 8.0 | | 8.0 | | | 8.0 | 8.0 | 8.0 | 0.0 | 3.0 | 5.0 | | 0.0 | |
| | 1.000 | 3.0 | | 6.0 | | | 8.0 | 7.0 | 8.0 | 0.0 | 0.0 | 3.0 | | 0.0 | |
| | .500 | 0.0 | | 0.0 | | | 8.0 | 6.0 | 7.0 | 0.0 | 0.0 | 0.0 | | 0.0 | |
| | .250 | 0.0 | | 0.0 | | | 3.0 | 3.0 | 6.0 | 0.0 | 0.0 | 0.0 | | 0.0 | |
| | .125 | 0.0 | | 0.0 | | | 0.0 | 0.0 | 7.0 | 0.0 | 0.0 | 0.0 | | 0.0 | |
| | .063 | 0.0 | | 0.0 | | | 0.0 | 0.0 | 5.0 | 0.0 | 0.0 | 0.0 | | 0.0 | |
| | .032 | 0.0 | | 0.0 | | | 0.0 | 0.0 | 0.0 | 0.0 | 0.0 | 0.0 | | 0.0 | |
| 1,9bα(and β)-dihydro-3α-isopropyl-3-methyl-5H—imidazo[1′:2′:1,2]pyrrolo[3,4-b]pyridine-2(3H),5-dione | 8.000 | 9.0 | | 9.0 | 9.0 | | 9.0 | 8.0 | 8.0 | 9.0 | 8.0 | 9.0 | 8.0 | 8.0 | 9.0 |
| | 2.000 | 9.0 | | 9.0 | 9.0 | | 9.0 | 8.0 | 9.0 | 9.0 | 8.0 | 9.0 | 8.0 | 7.0 | 9.0 |
| | 1.000 | 9.0 | | 9.0 | 9.0 | | 8.0 | 8.5 | 7.0 | 7.5 | 8.5 | 9.0 | 7.0 | 8.0 | 9.0 |
| | .500 | 8.0 | | 9.0 | 8.0 | | 8.5 | 8.0 | 8.5 | 6.5 | 7.5 | 8.0 | 7.0 | 6.5 | 8.0 |
| | .250 | 8.0 | | 8.0 | 7.0 | | 8.5 | 6.5 | 8.5 | 3.5 | 6.0 | 7.5 | 5.0 | 5.5 | 7.0 |
| | .125 | 7.0 | | 5.5 | 4.0 | | 5.5 | 3.0 | 8.0 | 2.0 | 2.5 | 4.5 | 2.0 | 2.5 | 5.0 |
| | .063 | 3.0 | | 2.5 | 2.0 | | 0.5 | 1.0 | 5.5 | 0.0 | 3.5 | 2.0 | 0.0 | 0.0 | 3.0 |
| | .032 | 1.0 | | 1.0 | | | 0.0 | 0.0 | 4.0 | 0.0 | 3.0 | 3.0 | 0.0 | 0.0 | 0.0 |
| | .016 | 0.0 | | 0.0 | | | 0.0 | 0.0 | 0.0 | 0.0 | | | | | |
| 1,9bβ-Dihydro-3α-isopropyl-3,7-dimethyl-5H—imidazo[1′:2′:1,2]pyrrolo[3,4-b]pyridine-2(3H),5-dione | 1.000 | 9.0 | | 9.0 | 9.0 | 9.0 | 9.0 | 9.0 | 9.0 | | 8.0 | 9.0 | 9.0 | 4.0 | 9.0 |
| | .750 | 9.0 | | 9.0 | 8.0 | 9.0 | 8.0 | 9.0 | 9.0 | 4.0 | 8.0 | 9.0 | 2.0 | 3.0 | 5.0 |
| | .500 | 9.0 | 9.0 | 9.0 | 8.5 | 8.5 | 8.0 | 8.5 | 9.0 | 3.0 | 4.0 | 9.0 | 2.0 | 2.0 | 5.0 |
| | .250 | 8.5 | 9.0 | 8.0 | 8.5 | 8.5 | 8.0 | 8.0 | 8.5 | 2.0 | 3.0 | 8.0 | 2.0 | 2.0 | 5.0 |
| | .125 | 8.0 | 9.0 | 7.5 | 4.0 | 9.0 | 4.0 | 8.0 | 3.0 | 2.0 | 2.0 | 6.0 | 2.0 | 2.0 | 2.0 |
| | .063 | 3.0 | 6.0 | 3.0 | 4.0 | 7.0 | 1.0 | 2.0 | 1.0 | 2.0 | 3.0 | 2.0 | 2.0 | 2.0 | 1.0 |
| | .032 | 0.0 | 4.0 | 2.0 | 2.0 | 3.0 | 0.0 | 0.0 | 0.0 | 2.0 | 2.0 | 2.0 | 2.0 | 2.0 | 1.0 |
| | .016 | 0.0 | 0.0 | 1.0 | 2.0 | 0.0 | 0.0 | 0.0 | 0.0 | 2.0 | 2.0 | 2.0 | 2.0 | 2.0 | 1.0 |
| (R)-(+)-1,9bα-Dihydro-3β-isopropyl-3-methyl-5H—imidazo[1′:2′:1,2]pyrrolo[3,4-b]pyridine-2(3H),5-dione | .500 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 8.0 | 8.0 | 9.0 |
| | .125 | 9.0 | 9.0 | 8.0 | 9.0 | 8.5 | 9.0 | 8.0 | 8.0 | 7.0 | 9.0 | 6.0 | 8.0 | 7.0 | 9.0 |
| | .063 | 8.0 | 9.0 | 7.0 | 9.0 | 7.0 | 8.0 | 8.0 | 8.0 | 7.0 | 8.0 | 4.0 | 6.0 | 7.0 | 9.0 |
| | .032 | 3.0 | 8.0 | 3.0 | 8.0 | 6.0 | 8.0 | 3.0 | 7.0 | 2.0 | 7.0 | 5.0 | 3.0 | 4.0 | 7.0 |
| | .016 | 0.0 | 4.0 | 3.0 | 7.0 | 3.0 | 7.0 | 0.0 | 2.0 | 2.0 | 2.0 | 4.0 | 2.0 | 3.0 | 7.0 |
| (±)-1,9bβ-Dihydro-3α-isopropyl-3-methyl-5H—imidazo[1′:2′:1,2]pyrrolo[3,4-b]pyridine-2(3H),5-dione | .500 | 9.0 | 9.0 | 9.0 | 9.0 | 9.0 | 9.0 | 9.0 | 9.0 | 3.0 | 9.0 | 9.0 | 9.0 | 8.0 | 9.0 |
| | .250 | 9.0 | 9.0 | 8.0 | 9.0 | 9.0 | 8.0 | 9.0 | 8.0 | 3.0 | 9.0 | 9.0 | 8.0 | 8.0 | 9.0 |
| | .125 | 8.0 | 9.0 | 7.0 | 9.0 | 8.0 | 7.0 | 8.0 | 7.0 | 4.0 | 9.0 | 6.0 | 8.0 | 7.0 | 9.0 |
| | .063 | 8.0 | 9.0 | 8.0 | 9.0 | 5.0 | 4.0 | 8.0 | 5.0 | 5.0 | 8.0 | 4.0 | 8.0 | 6.0 | 9.0 |
| | .032 | 3.0 | 7.0 | 4.0 | 3.0 | 5.0 | 0.0 | 3.0 | 3.0 | 3.0 | 4.0 | 3.0 | 3.0 | 2.0 | 7.0 |
| | .016 | 0.0 | 4.0 | 2.0 | 1.0 | 8.0 | 2.0 | 2.0 | 6.0 | 3.0 | 3.0 | 2.0 | 7.0 | 4.0 | 7.0 |
| 1,9bβ-Dihydro-3α-isopropyl-3,8-dimethyl-5H—imidazo[1′:2′:1,2]pyrrolo[3,4-b]pyridine-2(3H),5-dione | .500 | 9.0 | 9.0 | 8.0 | 9.0 | 9.0 | 9.0 | 9.0 | 9.0 | 3.0 | 9.0 | 9.0 | 9.0 | 8.0 | 9.0 |
| | .250 | 8.0 | 9.0 | 8.0 | 9.0 | 8.0 | 7.0 | 8.0 | 7.0 | 4.0 | 5.0 | 6.0 | 4.0 | 3.0 | 8.0 |
| | .125 | 0.0 | 9.0 | 6.0 | 7.0 | 5.0 | 4.0 | 8.0 | 5.0 | 4.0 | 4.0 | 4.0 | 2.0 | 2.0 | 3.0 |
| | .063 | 0.0 | 7.0 | 6.0 | 3.0 | 5.0 | 4.0 | 8.0 | 3.0 | 2.0 | 2.0 | 3.0 | 1.0 | 2.0 | 3.0 |
| | .032 | 0.0 | 4.0 | 4.0 | 2.0 | 5.0 | 0.0 | 3.0 | 3.0 | 2.0 | 0.0 | 0.0 | 1.0 | 2.0 | 2.0 |
| 8-(Allyloxy)-1,9bβ-dihydro-3α-isopropyl-3-methyl-5H—imidazo[1′:2′:1,2]pyrrolo[3,4-b]pyridine-2(3H),5-dione | .500 | 2.0 | 4.0 | 3.0 | 2.0 | 9.0 | 6.0 | 4.0 | 2.0 | 2.0 | 0.0 | 0.0 | 1.0 | | 0.0 |
| | .250 | 1.0 | 0.0 | 1.0 | 1.0 | 1.0 | 2.0 | 2.0 | 0.0 | 0.0 | 0.0 | 0.0 | 1.0 | 0.0 | 0.0 |
| 1,9bα-Dihydro-3α-isopropyl-3-methyl-5H—imidazo[1′:2′:1,2]pyrrolo[3,4-b] | .500 | 9.0 | 9.0 | 9.0 | 9.0 | 9.0 | 9.0 | 9.0 | 9.0 | 9.0 | 9.0 | 8.0 | 9.0 | 8.0 | 9.0 |
| | .250 | 9.0 | 9.0 | 7.0 | 9.0 | 9.0 | 9.0 | 9.0 | 9.0 | 9.0 | 9.0 | 7.0 | 9.0 | 8.0 | 9.0 |
| | .125 | 9.0 | 9.0 | 6.0 | 9.0 | 9.0 | 9.0 | 9.0 | 9.0 | 9.0 | 8.0 | 6.0 | 6.0 | 7.0 | 9.0 |

TABLE VI-continued
PRE-EMERGENCE TESTS - RATES IN KG/HA

| Compound | RATE | BARN-YARDGR | FOX-TAIL SP | P NUT SEDGE | QUACK GRASS | FLD BINDWD | MRNGLRY SP | RAG-WEED | VELVET-LEAF | CORN FIELD | COT-TON | RICE, NATO | SOY-BEAN BR | SOY-BEAN WI | S WHEAT ER |
|---|---|---|---|---|---|---|---|---|---|---|---|---|---|---|---|
| pyridine-2(3H),5-dione | .063 | 9.0 | 9.0 | 4.0 | 8.0 | 9.0 | 8.0 | 8.0 | 9.0 | 4.0 | 4.0 | 3.0 | 4.0 | 4.0 | 8.0 |
|  | .032 | 7.0 | 8.0 | 2.0 | 7.0 | 7.0 | 8.0 | 8.0 | 9.0 | 3.0 | 3.0 | 3.0 | 5.0 | 2.0 | 7.0 |
|  | .016 | 2.0 | 7.0 | 0.0 | 7.0 | 7.0 | 7.0 | 7.0 | 7.0 | 2.0 | 2.0 | 2.0 |  | 2.0 | 7.0 |
| 7-Ethyl-1,9bα(and β)-dihydro-3α-isopropyl-3-methyl-5H—imidazo[1′,2′:1,2]pyrrolo[3,4-b]pyridine-2(3H),5-dione | 1.000 | 9.0 | 9.0 | 8.0 | 9.0 | 9.0 | 9.0 | 9.0 | 7.5 | 3.0 | 4.0 | 9.0 | 0.0 | 1.0 | 7.0 |
|  | .500 | 8.5 | 9.0 | 8.0 | 9.0 | 8.5 | 7.5 | 9.0 | 7.0 | 2.0 | 2.0 | 9.0 | 0.0 | 1.0 | 2.0 |
|  | .250 | 7.0 | 9.0 | 5.5 | 8.0 | 8.0 | 2.5 | 7.0 | 7.0 | 2.0 | 0.0 | 6.0 | 0.0 | 0.0 | 0.0 |
|  | .125 | 6.0 | 6.0 | 3.0 | 5.0 | 5.0 | 0.5 | 4.5 | 4.0 | 1.0 | 0.0 | 3.0 | 0.0 | 0.0 | 0.0 |
|  | .063 | 2.0 | 2.0 | 0.5 | 2.0 | 5.0 | 0.0 | 0.0 | 0.0 | 1.0 | 0.0 | 3.0 | 0.0 | 0.0 | 0.0 |
|  | .032 | 0.0 | 0.0 | 0.0 | 0.0 | 0.0 | 0.0 | 0.0 | 0.0 | 1.0 | 0.0 | 2.0 | 0.0 | 0.0 | 0.0 |
|  | .016 | 0.0 | 0.0 | 0.0 | 0.0 | 0.0 | 0.0 | 0.0 | 0.0 | 1.0 | 0.0 | 1.0 | 0.0 | 0.0 | 0.0 |
| 1,9bβ-Dihydro-3α-isopropyl-8-methoxy-3-methyl-5H—imidazo[1′,2′:1,2]pyrrolo[3,4-b]pyridine-2(3H),5-dione | .500 | 9.0 | 9.0 | 9.0 | 9.0 | 9.0 | 9.0 | 9.0 | 7.0 | 7.0 | 8.0 | 6.0 | 5.0 | 4.0 | 7.0 |
|  | .250 | 8.0 | 9.0 | 6.0 | 7.0 | 7.0 | 8.0 | 8.0 | 4.0 | 5.0 | 6.0 | 4.0 | 0.0 | 3.0 | 7.0 |
|  | .125 | 8.0 | 7.0 | 7.0 | 7.0 | 8.0 | 8.0 | 5.0 | 2.0 | 3.0 | 5.0 | 3.0 | 1.0 | 1.0 | 5.0 |
|  | .063 | 2.0 | 6.0 | 4.0 | 2.0 | 6.0 | 6.0 | 2.0 | 1.0 | 3.0 | 2.0 | 2.0 | 0.0 | 0.0 | 2.0 |
|  | .032 | 0.0 | 0.0 | 1.0 | 0.0 | 3.0 | 3.0 | 0.0 | 0.0 | 2.0 | 2.0 | 2.0 | 0.0 | 0.0 | 1.0 |
|  | .016 | 0.0 | 0.0 | 0.0 | 0.0 | 0.0 | 0.0 | 0.0 | 0.0 | 2.0 | 2.0 | 1.0 | 0.0 | 0.0 | 1.0 |
| 1,9bα-Dihydro-3α-isopropyl-3-methyl-5H—imidazo[1′,2′:1,2]pyrrolo[3,4-b]quinoline-2(3H),5-dione | .500 | 8.0 | 5.0 | 6.0 | 9.0 | 4.0 | 0.0 | 7.0 | 4.0 | 0.0 | 0.0 | 0.0 | 0.0 | 0.0 | 0.0 |
|  | .250 | 7.0 | 5.0 | 2.0 | 9.0 | 3.0 | 0.0 | 7.0 | 3.0 | 0.0 | 0.0 | 4.0 | 0.0 | 1.0 | 9.0 |
|  | .125 | 0.0 | 5.0 | 0.0 | 0.0 | 0.0 | 0.0 | 2.0 | 0.0 | 0.0 | 0.0 | 2.0 | 0.0 | 1.0 | 9.0 |
|  | .063 | 0.0 | 0.0 | 0.0 | 0.0 | 0.0 | 0.0 | 0.0 | 0.0 | 0.0 | 0.0 | 2.0 | 0.0 | 0.0 | 9.0 |
|  | .032 | 0.0 | 0.0 | 0.0 | 0.0 | 0.0 | 0.0 | 0.0 | 0.0 | 0.0 | 0.0 | 1.0 | 0.0 | 0.0 | 7.0 |
|  | .016 | 0.0 | 0.0 | 0.0 | 0.0 | 0.0 | 0.0 | 0.0 | 0.0 | 0.0 | 0.0 | 1.0 | 0.0 | 0.0 | 4.0 |
| 8-Chloro-1,9β-dihydro-3α-isopropyl-3-methyl-5H—imidazo[1′,2′:1,2]pyrrolo[3,4-b]pyridine-2(3H),5-dione | .500 | 9.0 | 9.0 | 9.0 | 9.0 | 9.0 | 7.0 | 9.0 | 5.0 | 6.0 | 2.0 | 4.0 | 0.0 | 0.0 | 2.0 |
|  | .250 | 4.0 | 9.0 | 9.0 | 9.0 | 9.0 | 7.0 | 9.0 | 3.0 | 3.0 | 1.0 | 2.0 | 0.0 | 1.0 | 8.0 |
|  | .125 | 1.0 | 4.0 | 7.0 | 9.0 | 4.0 | 5.0 | 8.0 | 3.0 | 2.0 | 1.0 | 2.0 | 0.0 | 1.0 | 8.0 |
|  | .063 | 0.0 | 1.0 | 6.0 | 7.0 | 4.0 | 2.0 | 3.0 | 2.0 | 1.0 | 0.0 | 1.0 | 0.0 | 0.0 | 7.0 |
|  | .032 | 0.0 | 0.0 | 2.0 | 6.0 | 0.0 | 1.0 | 0.0 | 0.0 | 0.0 | 0.0 | 1.0 | 0.0 | 0.0 | 4.0 |
|  | .016 | 0.0 | 0.0 | 1.0 | 3.0 | 0.0 | 0.0 | 0.0 | 0.0 | 0.0 | 0.0 | 1.0 | 0.0 | 0.0 | 2.0 |
| 7-Ethyl-1,9bβ-dihydro-3α-isopropyl-3-methyl-5H—imidazo[1′,2′:1,2]pyrrolo[3,4-b]pyridine-2(3H),5-dione | .500 | 9.0 | 9.0 | 8.0 | 2.0 | 9.0 | 8.0 | 9.0 | 8.0 | 3.0 | 0.0 | 9.0 | 0.0 | 0.0 | 8.0 |
|  | .250 | 9.0 | 9.0 | 7.0 | 1.0 | 9.0 | 7.0 | 7.0 | 8.0 | 2.0 | 2.0 | 9.0 | 0.0 | 4.0 | 8.0 |
|  | .125 | 8.0 | 9.0 | 6.0 | 0.0 | 7.0 | 4.0 | 4.0 | 6.0 | 1.0 | 1.0 | 9.0 | 0.0 | 3.0 | 8.0 |
|  | .063 | 7.0 | 3.0 | 1.0 | 0.0 | 4.0 | 0.0 | 2.0 | 3.0 | 0.0 | 0.0 | 7.0 | 0.0 | 1.0 | 2.0 |
|  | .032 | 2.0 | 3.0 | 0.0 | 0.0 | 1.0 | 0.0 | 0.0 | 1.0 | 0.0 | 0.0 | 6.0 | 0.0 | 0.0 | 3.0 |
|  | .016 | 0.0 | 0.0 | 0.0 | 0.0 | 0.0 | 0.0 | 0.0 | 0.0 | 0.0 | 0.0 | 2.0 | 0.0 | 0.0 | 1.0 |
| 1,9bβ-Dihydro-3α-isopropyl-3-methyl-2-thio-5H—imidazo[1′,2′:1,2]pyrrolo[3,4-b]pyridine-2(3H),5-dione | .500 | 9.0 | 9.0 | 9.0 | 9.0 | 9.0 | 8.0 | 9.0 | 9.0 | 9.0 | 7.0 | 9.0 | 7.0 | 7.0 | 9.0 |
|  | .250 | 7.0 | 8.0 | 9.0 | 9.0 | 9.0 | 8.0 | 9.0 | 8.0 | 9.0 | 7.0 | 8.0 | 7.0 | 7.0 | 9.0 |
|  | .125 | 6.0 | 4.0 | 8.0 | 7.0 | 7.0 | 6.0 | 7.0 | 7.0 | 9.0 | 3.0 | 6.0 | 5.0 | 4.0 | 9.0 |
|  | .063 | 1.0 | 1.0 | 2.0 | 7.0 | 6.0 | 2.0 | 2.0 | 6.0 | 6.0 | 1.0 | 2.0 | 3.0 | 2.0 | 4.0 |
|  | .032 | 0.0 | 0.0 | 0.0 | 2.0 | 0.0 | 0.0 | 1.0 | 3.0 | 3.0 | 0.0 | 1.0 | 1.0 | 1.0 | 2.0 |
|  | .016 | 0.0 | 0.0 | 0.0 | 0.0 | 0.0 | 0.0 | 0.0 | 1.0 | 1.0 | 0.0 | 0.0 | 0.0 | 0.0 | 0.0 |

EXAMPLE 55

Postemergence herbicidal evaluation of test compounds

The postemergence herbicidal activity of test compounds is demonstrated by the following tests, using the procedure of Example 53, excepting that compounds are evaluated at rates beteween 0.063 and 10.0 kg/ha, and wild oats *Avena fatua* and sunflower *Helianthus annus* L. are substituted for wheat, Williams variety, and cotton. Data obtained are reported in Table VII.

TABLE VII
POST-EMERGENCE TESTS - RATES IN KG/HA

| Compound | RATE | BARN- YARDGR | GREEN FOX | P NUT SEDGE | WILD OATS | QUACK GRASS | FLD BINDWD | MRNGLRY SP | RAG- WEED | VELVET- LEAF | CORN FIELD | RICE, NATO | SUNFLR XXX | S WHEAT ER | SOY- BEAN BR |
|---|---|---|---|---|---|---|---|---|---|---|---|---|---|---|---|
| 9bβ-(Benzyloxy)-3α-ethyl-1,9b-dihydro-3-methyl-5H—imidazo[1',2':1,2]pyrrolo[3,4-b]pyridine-2(3H),5-dione | 10.000 | 8.0 | 8.0 | 0.0 | 9.0 | | | 5.0 | 7.0 | 8.0 | 0.0 | 2.0 | | | |
| | 1.000 | 0.0 | 7.0 | 0.0 | 0.0 | | | 4.0 | 0.0 | 8.0 | 0.0 | 0.0 | | | |
| | .500 | 0.0 | 3.0 | 0.0 | 0.0 | | | 7.0 | 0.0 | 6.0 | 0.0 | 0.0 | | | |
| | .250 | 0.0 | 0.0 | 0.0 | 0.0 | | | 7.0 | 0.0 | 6.0 | 0.0 | 0.0 | | | |
| | .125 | 0.0 | 0.0 | 0.0 | 0.0 | | | 7.0 | 0.0 | 3.0 | 0.0 | 0.0 | | | |
| | .063 | 0.0 | 0.0 | 0.0 | 0.0 | | | 7.0 | 0.0 | 0.0 | 0.0 | 0.0 | | | |
| 9bα-(Benzyloxy)-3α-ethyl-1,9b-dihydro-3-methyl-5H—imidazo[1',2':1,2]pyrrolo[3,4-b]pyridine-2(3H),5-dione | 10.000 | 8.0 | 8.0 | 0.0 | 8.0 | | | 5.0 | 3.0 | 9.0 | 0.0 | 2.0 | | | |
| | 1.000 | 0.0 | 3.0 | 0.0 | 0.0 | | | 4.0 | 0.0 | 7.0 | 0.0 | 0.0 | | | |
| | .500 | 0.0 | 2.0 | 0.0 | 0.0 | | | 3.0 | 0.0 | 8.0 | 0.0 | 0.0 | | | |
| | .250 | 0.0 | 1.0 | 0.0 | 0.0 | | | 3.0 | 0.0 | 7.0 | 0.0 | 0.0 | | | |
| | .125 | 0.0 | 1.0 | 0.0 | 0.0 | | | 1.0 | 0.0 | 6.0 | 0.0 | 0.0 | | | |
| | .063 | 0.0 | 0.0 | 0.0 | 0.0 | | | 0.0 | 0.0 | 1.0 | 0.0 | 0.0 | | | |
| 3α-Ethyl-1,9b-dihydro-3-methyl-9bα-(2-propynyloxy)-5H—imidazo[1',2':1,2]-pyrrolo[3,4-b]pyridine-2(3H),5-dione | 10.000 | 7.0 | 7.0 | 0.0 | 8.0 | | | 5.0 | 1.0 | 7.0 | 0.0 | 3.0 | | | |
| | 1.000 | 0.0 | 1.0 | 0.0 | 0.0 | | | 2.0 | 0.0 | 2.0 | 0.0 | 0.0 | | | |
| | .500 | 0.0 | 1.0 | 0.0 | 0.0 | | | 0.0 | 0.0 | 0.0 | 0.0 | 0.0 | | | |
| | .250 | 0.0 | 1.0 | 0.0 | 0.0 | | | 0.0 | 0.0 | 0.0 | 0.0 | 0.0 | | | |
| | .125 | 0.0 | 0.0 | 0.0 | 0.0 | | | 0.0 | 0.0 | 0.0 | 0.0 | 0.0 | | | |
| | .063 | 0.0 | 0.0 | 0.0 | 0.0 | | | 0.0 | 0.0 | 0.0 | 0.0 | 0.0 | | | |
| 1,9b-Dihydro-3α-isopropyl-9b-methoxy-3-methyl-5H—imidazo[1',2':1,2]pyrrolo[3,4-b]pyridine-2(3H),5-dione | 8.000 | 9.0 | 9.0 | 9.0 | 9.0 | 9.0 | 9.0 | 8.0 | 9.0 | 9.0 | 9.0 | 8.0 | 9.0 | 9.0 | |
| | 1.000 | 9.0 | 9.0 | 8.0 | 9.0 | 8.0 | 9.0 | 9.0 | 9.0 | 9.0 | 9.0 | 8.0 | 9.0 | 9.0 | |
| | .500 | 9.0 | 9.0 | 8.0 | 9.0 | 7.0 | 9.0 | 9.0 | 8.0 | 9.0 | 9.0 | 8.0 | 9.0 | 8.0 | |
| | .250 | 9.0 | 9.0 | 8.0 | 9.0 | | 9.0 | 9.0 | 8.0 | 9.0 | 9.0 | 8.0 | 9.0 | 8.0 | |
| | .125 | 8.0 | 8.0 | 8.0 | 8.0 | | 7.0 | 9.0 | 4.0 | 8.0 | 9.0 | 6.0 | 8.0 | 6.0 | |
| | .063 | 0.0 | 0.0 | 8.0 | 0.0 | | 0.0 | 9.0 | 2.0 | 0.0 | 9.0 | 0.0 | 0.0 | 0.0 | |
| 1,9b-Dihydro-3α-isopropyl-3-methyl-9bα-propoxy-5H—imidazo[1',2':1,2]pyrrolo[3,4-b]pyridine-2(3H),5-dione | 8.000 | 9.0 | 9.0 | 9.0 | 9.0 | 9.0 | 4.0 | 9.0 | 9.0 | 9.0 | 9.0 | 9.0 | 9.0 | 9.0 | |
| | 1.000 | 9.0 | 9.0 | 9.0 | 9.0 | 9.0 | 9.0 | 9.0 | 9.0 | 9.0 | 9.0 | 9.0 | 9.0 | 9.0 | |
| | .500 | 9.0 | 9.0 | 9.0 | 9.0 | 8.0 | 9.0 | 8.0 | 8.0 | 9.0 | 9.0 | 8.0 | 9.0 | 8.0 | |
| | .250 | 9.0 | 9.0 | 8.0 | 9.0 | 8.0 | 9.0 | 8.0 | 9.0 | 8.0 | 9.0 | 8.0 | 9.0 | 8.0 | |
| | .125 | 8.0 | 8.0 | 7.0 | 8.0 | 7.0 | 9.0 | 8.0 | 7.0 | 8.0 | 9.0 | 8.0 | 8.0 | 8.0 | |
| | .063 | 4.0 | 7.0 | 7.0 | 7.0 | 5.0 | 6.0 | 7.0 | 6.0 | 4.0 | 9.0 | 8.0 | 8.0 | 8.0 | |
| cis-and/or trans-1,9b-Dihydro-3-isopropyl-3-methyl-9b-(2-propynylamino)-5H—imidazo[1',2':1,2](and/or [2',1':5,1]pyrrolo[3,4-b]pyridine-2(3H),5-dione | 8.000 | 8.0 | 9.0 | 7.0 | 9.0 | 9.0 | 2.0 | 7.0 | 6.0 | 8.0 | 0.0 | 0.0 | 0.0 | 0.0 | |
| | 1.000 | 0.0 | 0.0 | 7.0 | 0.0 | 9.0 | 7.0 | 7.0 | 3.0 | 4.0 | 0.0 | 0.0 | 0.0 | 0.0 | |
| | .500 | 0.0 | 0.0 | 6.0 | 0.0 | 9.0 | 2.0 | 7.0 | 0.0 | 8.0 | 0.0 | 0.0 | 0.0 | 0.0 | |
| | .250 | 0.0 | 0.0 | 5.0 | 0.0 | 9.0 | 1.0 | 2.0 | 0.0 | 0.0 | 0.0 | 0.0 | 0.0 | 0.0 | |
| | .125 | 0.0 | 0.0 | 4.0 | 0.0 | 5.0 | 0.0 | 0.0 | 0.0 | 0.0 | 0.0 | 0.0 | 0.0 | 0.0 | |
| | .063 | 0.0 | 0.0 | 3.0 | 0.0 | 3.0 | 0.0 | 0.0 | 0.0 | 0.0 | 0.0 | 0.0 | 0.0 | 0.0 | |
| 9bα-{[p-(Dimethylamino)benzyl]oxy}-1,9b-dihydro-3α-isopropyl-3-methyl-5H—imidazo[1',2':1,2]pyrrolo[3,4-b]pyridine-2(3H),5-dione | 1.000 | 9.0 | 9.0 | 6.0 | 9.0 | 9.0 | 9.0 | 9.0 | 3.0 | 9.0 | 0.0 | 9.0 | 9.0 | 9.0 | |
| | .500 | 9.0 | 9.0 | 6.0 | 9.0 | 9.0 | 9.0 | 9.0 | 1.0 | 9.0 | 0.0 | 9.0 | 9.0 | 9.0 | |
| | .250 | 9.0 | 9.0 | 5.0 | 9.0 | 9.0 | 9.0 | 8.0 | 1.0 | 9.0 | 0.0 | 9.0 | 9.0 | 9.0 | |
| | .125 | 7.0 | 9.0 | 4.0 | 9.0 | 9.0 | 9.0 | 8.0 | 0.0 | 8.0 | 0.0 | 9.0 | 9.0 | 8.0 | |
| | .063 | 3.0 | 9.0 | 3.0 | 7.0 | 3.0 | 7.0 | 7.0 | 0.0 | 7.0 | 0.0 | 9.0 | 7.0 | 8.0 | |
| 9bα-Amino-1,9b-dihydro-3α-isopropyl-3-methyl-5H—imidazo[1',2':1,2]pyrrolo[3,4-b]pyridine-2(3H),5-dione | 1.000 | 9.0 | 9.0 | 9.0 | 9.0 | 9.0 | 9.0 | 9.0 | 9.0 | 9.0 | 9.0 | 9.0 | 9.0 | 0.0 | |
| | .500 | 9.0 | 8.0 | 8.0 | 9.0 | 9.0 | 9.0 | 8.0 | 1.0 | 5.0 | 9.0 | 9.0 | 9.0 | 0.0 | |
| | .250 | 7.0 | 7.0 | 6.0 | 7.0 | 9.0 | 9.0 | 7.0 | 8.0 | 3.0 | 9.0 | 8.0 | 7.0 | 0.0 | |
| | .125 | 3.0 | 6.0 | 6.0 | 9.0 | 8.0 | 9.0 | 7.0 | 4.0 | 8.0 | 9.0 | 8.0 | 7.0 | 0.0 | |
| | .063 | 9.0 | 5.0 | 4.0 | 7.0 | 9.0 | 9.0 | 6.0 | 2.0 | 9.0 | 8.0 | 9.0 | 9.0 | 9.0 | |
| 9bα-(Benzyloxy)-1,9b-dihydro-3α-isopropyl-3-methyl-5H—imidazo- | 8.000 | 9.0 | 9.0 | 9.0 | 9.0 | 9.0 | 9.0 | 8.0 | 8.0 | 9.0 | 8.0 | 8.0 | 9.0 | 9.0 | |
| | 1.000 | 9.0 | 9.0 | 8.0 | 9.0 | 9.0 | 9.0 | 9.0 | 9.0 | 9.0 | 9.0 | 9.0 | 9.0 | 9.0 | |

TABLE VII-continued
POST-EMERGENCE TESTS - RATES IN KG/HA

| Compound | RATE | BARN-YARDGR | GREEN FOX | P NUT SEDGE | WILD OATS | QUACK GRASS | FLD BINDWD | MRNGLRY SP | RAG-WEED | VELVET-LEAF | CORN FIELD | RICE, NATO | SUNFLR XXX | S WHEAT ER | SOY-BEAN BR |
|---|---|---|---|---|---|---|---|---|---|---|---|---|---|---|---|
| dazo[1′:2′:1,2]pyrrolo[3,4-b]-pyridine-2(3H),5-dione | .500 | 9.0 | 9.0 | 6.0 | 9.0 | 9.0 | 9.0 | 9.0 | 8.0 | 9.0 | 9.0 | 9.0 | 9.0 | 9.0 | |
|  | .250 | 9.0 | 9.0 | 4.0 | 9.0 | 9.0 | 9.0 | 9.0 | 5.0 | 9.0 | 9.0 | 9.0 | 9.0 | 9.0 | |
|  | .125 | 2.0 | 9.0 | 4.0 | 9.0 | 2.0 | 9.0 | 2.0 | 5.0 | 9.0 | 9.0 | 9.0 | 9.0 | 9.0 | |
|  | .063 | 9.0 | 9.0 | 3.0 | 9.0 | 9.0 | 9.0 | 9.0 | 0.0 | 9.0 | 9.0 | 9.0 | 9.0 | 9.0 | |
| 9bα(and/or β)-Ethoxy-1,9b-di-hydro-3α-isopropyl-3-methyl-5H—imidazo[1′,2′:1,2]pyrrolo[3,4-b]pyridine-2(3H),5-dione | 1.000 | 8.0 | 9.0 | 8.0 | 9.0 | 9.0 | 9.0 | 9.0 | 9.0 | 9.0 | 8.0 | 8.0 | 9.0 | 9.0 | 9.0 |
|  | .500 | 8.0 | 9.0 | 8.0 | 9.0 | 9.0 | 9.0 | 9.0 | 9.0 | 9.0 | 9.0 | 8.0 | 9.0 | 9.0 | 9.0 |
|  | .250 | 8.0 | 9.0 | 7.0 | 9.0 | 9.0 | 9.0 | 9.0 | 9.0 | 9.0 | 9.0 | 7.0 | 9.0 | 9.0 | 4.0 |
|  | .125 | 8.0 | 8.0 | 6.0 | 9.0 | 9.0 | 9.0 | 9.0 | 6.0 | 9.0 | 9.0 | 7.0 | 9.0 | 9.0 | 2.0 |
|  | .063 | 6.0 | 8.0 | 3.0 | 9.0 | 9.0 | 9.0 | 9.0 | 5.0 | 9.0 | 9.0 | 7.0 | 9.0 | 9.0 | 1.0 |
| 2-Isopropyl-7-methoxy-2-methyl-5H—imidazo[1′,2′:1,2]-pyrrolo[3,4-b]pyridine-3(2H),5-dione and 3-isopropyl-7-methoxy-3-methyl-5H—imidazo[1′,2′:1,2]pyrrolo[3,4-b]pyridine-2(3H),5-dione | 1.000 | 9.0 | | 9.0 | 9.0 | 9.0 | 9.0 | 8.0 | 9.0 | 9.0 | 9.0 | 9.0 | 9.0 | 9.0 | 9.0 |
|  | .500 | 9.0 | | 9.0 | 9.0 | 9.0 | 9.0 | 9.0 | 9.0 | 9.0 | 9.0 | 9.0 | 9.0 | 9.0 | 8.0 |
|  | .250 | 9.0 | | 9.0 | 9.0 | 9.0 | 9.0 | 7.0 | 9.0 | 9.0 | 9.0 | 9.0 | 9.0 | 9.0 | 8.0 |
|  | .125 | 9.0 | | 9.0 | 9.0 | 9.0 | 9.0 | 5.0 | 9.0 | 9.0 | 9.0 | 9.0 | 9.0 | 9.0 | 7.0 |
|  | .063 | 9.0 | | 9.0 | 9.0 | 9.0 | 9.0 | 5.0 | 6.0 | 9.0 | 9.0 | 9.0 | 9.0 | 8.0 | 6.0 |
| 8-(Alloyloxy)-2-isopropyl-2-methyl-5H—imidazo[1′,2′:1,2]-pyrrolo[3,4-b]pyridine-3(2H),5-dione | 1.000 | 9.0 | | 8.0 | 9.0 | 8.0 | 9.0 | 9.0 | 8.0 | 7.0 | 9.0 | 8.0 | 9.0 | 9.0 | 7.0 |
|  | .500 | 8.0 | | 6.0 | 9.0 | 9.0 | 4.0 | 8.0 | 3.0 | 4.0 | 9.0 | 8.0 | 9.0 | 9.0 | 7.0 |
|  | .250 | 7.0 | | 6.0 | 9.0 | 1.0 | 2.0 | 7.0 | 0.0 | 4.0 | 9.0 | 7.0 | 8.0 | 8.0 | 4.0 |
|  | .125 | 3.0 | | 4.0 | 9.0 | 0.0 | 0.0 | 4.0 | 0.0 | 1.0 | 7.0 | 4.0 | 7.0 | 4.0 | 2.0 |
|  | .063 | 0.0 | | 1.0 | 2.0 | 0.0 | 0.0 | 1.0 | 0.0 | 0.0 | 7.0 | 3.0 | 3.0 | 1.0 | 1.0 |
| 2-Isopropyl-2,8-dimethyl-5H—dihydro[1′,2′:1,2]pyrrolo[3,4-b]pyridine-3(2H),5-dione | 1.000 | 9.0 | | 9.0 | 9.0 | 9.0 | 9.0 | 9.0 | 9.0 | 9.0 | 9.0 | 9.0 | 9.0 | 9.0 | 9.0 |
|  | .500 | 9.0 | | 9.0 | 9.0 | 9.0 | 9.0 | 9.0 | 9.0 | 9.0 | 9.0 | 9.0 | 9.0 | 9.0 | 8.0 |
|  | .250 | 9.0 | | 9.0 | 9.0 | 9.0 | 9.0 | 9.0 | 9.0 | 9.0 | 9.0 | 9.0 | 9.0 | 9.0 | 8.0 |
|  | .125 | 9.0 | | 9.0 | 9.0 | 9.0 | 9.0 | 8.0 | 9.0 | 8.0 | 9.0 | 9.0 | 9.0 | 9.0 | 6.0 |
|  | .063 | 9.0 | | 8.0 | 8.0 | 9.0 | 9.0 | 8.0 | 9.0 | 8.0 | 7.0 | 8.0 | 9.0 | 8.0 | 5.0 |
| 7-Chloro-1,9bβ-dihydro-3α-isopropyl-3-methyl-5H—imidazo[1′,2′:1,2]pyrrolo[3,4-b]pyridine-2(3H),5-dione | 1.000 | 9.0 | | 9.0 | 8.0 | 9.0 | 6.0 | 9.0 | 9.0 | 7.0 | 6.0 | 9.0 | 9.0 | 8.0 | 4.0 |
|  | .500 | 8.0 | | 5.0 | 5.0 | 9.0 | 5.0 | 9.0 | 9.0 | 5.0 | 3.0 | 8.0 | 9.0 | 6.0 | 3.0 |
|  | .250 | 6.0 | | 8.0 | 1.0 | 6.0 | 4.0 | 5.0 | 9.0 | 3.0 | 1.0 | 7.0 | 9.0 | 2.0 | 2.0 |
|  | .125 | 3.0 | | 2.0 | 0.0 | 6.0 | 4.0 | 5.0 | 9.0 | 3.0 | 2.0 | 5.0 | 9.0 | 1.0 | 1.0 |
|  | .063 | 3.0 | | 2.0 | 0.0 | 3.0 | 4.0 | 2.0 | 8.0 | 3.0 | 2.0 | 5.0 | 9.0 | 1.0 | 0.0 |
| 2-Isopropyl-2-methyl-5H—furo[2,3-b]imidazo[2′,1′:5,1]-pyrrolo[3,4-e]pyridine-3(2H),5-dione | 1.000 | 9.0 | | 6.0 | 0.0 | 9.0 | 9.0 | 7.0 | 9.0 | 8.0 | 9.0 | 9.0 | 9.0 | 9.0 | 2.0 |
|  | .500 | 8.0 | | 7.0 | 0.0 | 6.0 | 8.0 | 7.0 | 7.0 | 9.0 | 9.0 | 8.0 | 9.0 | 9.0 | 2.0 |
|  | .250 | 8.0 | | 2.0 | 9.0 | 2.0 | 9.0 | 6.0 | 4.0 | 2.0 | 9.0 | 9.0 | 9.0 | 3.0 | 1.0 |
|  | .125 | 8.0 | | 2.0 | 7.0 | 0.0 | 7.0 | 2.0 | 4.0 | 4.0 | 9.0 | 7.0 | 9.0 | 2.0 | 0.0 |
|  | .063 | 2.0 | | 0.0 | 2.0 | 0.0 | 4.0 | 0.0 | 4.0 | 0.0 | 4.0 | 5.0 | 9.0 | 1.0 | 0.0 |
| 1,9bα-Dihydro-3α-isopropyl-3-methyl-2-thio-5H—imidazo[1′,2′:1,2]pyrrolo[3,4-b]pyri-dine-2(3H),5-dione | 1.000 | 4.0 | | 0.0 | 0.0 | 4.0 | 7.0 | 7.0 | 0.0 | 4.0 | 9.0 | 3.0 | 7.0 | 5.0 | 5.0 |
|  | .500 | 3.0 | | 0.0 | 0.0 | 3.0 | 7.0 | 7.0 | 2.0 | 4.0 | 9.0 | 2.0 | 4.0 | 4.0 | 3.0 |
|  | .250 | 3.0 | | 0.0 | 0.0 | 1.0 | 7.0 | 6.0 | 0.0 | 3.0 | 2.0 | 2.0 | 3.0 | 2.0 | 2.0 |
|  | .125 | 2.0 | | 0.0 | 0.0 | 1.0 | 7.0 | 5.0 | 0.0 | 2.0 | 1.0 | 2.0 | 2.0 | 1.0 | 2.0 |
|  | .063 | 2.0 | | 0.0 | 0.0 | 1.0 | 6.0 | 5.0 | 0.0 | 1.0 | 1.0 | 2.0 | 2.0 | 0.0 | 2.0 |
| 1,9bα(and 9bβ-Dihydro-3α-iso-propyl-3,7-dimethyl-5H—imidazo[1′,2′:1,2]pyrrolo[3,4-b]pyridine-2(3H),5-dione | .400 |  |  |  |  |  |  |  |  |  |  |  |  |  |  |
|  | .375 | 9.0 | 8.0 | 4.0 | 7.0 | 0.0 | 8.0 | 7.0 | 8.0 | 8.0 | 2.0 | 8.0 | 8.0 | 7.0 | 3.0 |
|  | .300 |  |  |  |  |  |  |  |  |  |  |  |  | 6.0 |  |
|  | .100 |  |  |  |  |  |  |  |  |  |  |  |  | 4.0 |  |
|  | .080 |  |  |  |  |  |  |  |  |  |  |  |  | 0.0 |  |
| (R)—(—)-1,9bβ(and α)-Dihydro-3β-isopropyl-3-methyl-5H—imi- | .063 | 9.0 | 9.0 | 1.0 |  | 4.0 | 9.0 | 7.5 | 8.0 | 9.0 | 0.0 | 4.0 | 6.0 | 0.0 | 0.0 |
|  | .250 | 9.0 | 9.0 | 0.0 | 3.0 | 3.0 | 8.5 | 7.5 | 8.0 | 8.5 |  |  |  |  |  |
|  | .200 | 9.0 | 6.0 | 0.0 |  | 0.0 | 6.0 | 5.0 | 5.0 | 2.0 |  |  |  |  |  |
|  |  | 9.0 | 9.0 | 7.5 |  | 6.5 | 9.0 | 8.5 | 9.0 | 9.0 |  |  |  |  |  |
|  |  | 9.0 | 9.0 | 7.0 |  | 5.5 | 9.0 | 8.5 | 9.0 | 9.0 |  |  |  |  |  |

TABLE VII-continued
POST-EMERGENCE TESTS - RATES IN KG/HA

| Compound | RATE | BARN-YARDGR | GREEN FOX | P NUT SEDGE | WILD OATS | QUACK GRASS | FLD BINDWD | MRNGLRY SP | RAG-WEED | VELVET-LEAF | CORN FIELD | RICE, NATO | SUNFLR XXX | S WHEAT ER | SOY-BEAN BR |
|---|---|---|---|---|---|---|---|---|---|---|---|---|---|---|---|
| dazo[1′:2′:1,2]pyrrolo[3,4-b]pyridine-2(3H),5-dione | .175 | 9.0 | 9.0 | 6.5 | | 6.0 | 9.0 | 8.0 | 9.0 | 9.0 | | | | | |
| | .150 | 9.0 | 9.0 | 6.0 | | 4.5 | 9.0 | 8.0 | 9.0 | 9.0 | | | | | |
| | .125 | 9.0 | 9.0 | 3.5 | | 5.0 | 9.0 | 8.0 | 8.5 | 9.0 | | | | | |
| | .100 | 9.0 | 9.0 | 3.5 | | 4.5 | 9.0 | 8.0 | 8.5 | 9.0 | | | | | |
| | .080 | 8.5 | 9.0 | 2.5 | | 3.0 | 9.0 | 8.0 | 7.5 | 9.0 | | | | | |
| 7-(Allyloxy)-1,9bβ-dihydro-3α-isopropyl-3-methyl-5H—imidazo[1′,2′:1,2]pyrrolo[3,4-b]pyridine-2(3H),5-dione | 1.000 | 8.0 | | 0.0 | 2.0 | 3.0 | 9.0 | 8.0 | 6.0 | 4.0 | 6.0 | 4.0 | 7.0 | 2.0 | 0.0 |
| | .500 | 8.0 | | 0.0 | 1.0 | 2.0 | 9.0 | 2.0 | 4.0 | 2.0 | 3.0 | 4.0 | 7.0 | 1.0 | 0.0 |
| | .250 | 8.0 | | 0.0 | 0.0 | 1.0 | 6.0 | 1.0 | 0.0 | | 3.0 | 3.0 | 6.0 | 1.0 | 0.0 |
| | .125 | 8.0 | | 0.0 | 0.0 | 0.0 | 6.0 | 1.0 | 0.0 | | 5.0 | 4.0 | 6.0 | 0.0 | 0.0 |
| | .063 | 7.0 | | 0.0 | 0.0 | 0.0 | 5.0 | 0.0 | 0.0 | | 5.0 | 4.0 | 6.0 | 0.0 | 0.0 |
| 1,9bα-Dihydro-3α-isopropyl-3,7-dimethyl-5H—imidazo[1′,2′:1,2]pyrrolo[3,4-b]pyridine-2(3H),5-dione | .250 | 9.0 | 9.0 | 0.0 | | 5.5 | 9.0 | 8.5 | 9.0 | 0.0 | | | | | |
| | .200 | 9.0 | 9.0 | 0.0 | | 5.0 | 9.0 | 8.0 | 9.0 | 9.0 | | | | | |
| | .175 | 9.0 | 9.0 | 0.0 | | 4.5 | 9.0 | 8.0 | 9.0 | 9.0 | | | | | |
| | .150 | 9.0 | 9.0 | 0.0 | | 6.0 | 9.0 | 8.0 | 9.0 | 9.0 | | | | | |
| | .125 | 9.0 | 9.0 | 0.0 | | 3.0 | 9.0 | 8.0 | 9.0 | 9.0 | | | | | |
| | .100 | 9.0 | 9.0 | 0.0 | | 3.0 | 9.0 | 7.5 | 7.0 | 9.0 | | | | | |
| | .080 | 8.0 | 9.0 | 0.0 | | 3.0 | 9.0 | 7.0 | 7.5 | 9.0 | | | | | |
| (3R,9bR)—trans-(−)-1,9b-Dihydro-3-isopropyl-3,7-dimethyl-5H—imidazo[1′,2′:1,2]pyrrolo[3,4-b]pyridine-2(3H),5-dione | .250 | 9.0 | 9.0 | 4.5 | | 3.0 | 9.0 | 8.5 | 9.0 | 9.0 | | | | | |
| | .200 | 9.0 | 9.0 | 4.0 | | 3.0 | 9.0 | 8.5 | 9.0 | 9.0 | | | | | |
| | .175 | 9.0 | 9.0 | 4.5 | | 3.0 | 9.0 | 8.5 | 8.5 | 9.0 | | | | | |
| | .150 | 9.0 | 9.0 | 4.0 | | 3.0 | 9.0 | 8.5 | 8.5 | 9.0 | | | | | |
| | .125 | 9.0 | 9.0 | 3.5 | | 3.0 | 9.0 | 8.0 | 8.5 | 9.0 | | | | | |
| | .100 | 9.0 | 9.0 | 3.5 | | 3.0 | 9.0 | 8.0 | 8.5 | 9.0 | | | | | |
| | .080 | 9.0 | 9.0 | 2.0 | | 3.0 | 9.0 | 8.0 | 8.5 | 9.0 | | | | | |
| (3R,9bS)—cis-(+)-1,9b-Dihydro-3-isopropyl-3,7-dimethyl-5H—imidazo[1′,2′:1,2]pyrrolo[3,4-b]pyridine-2(3H),5-dione | .250 | 9.0 | 9.0 | 8.0 | | 6.0* | 8.0 | 7.5 | 8.5 | 9.0 | | | | | |
| | .200 | 9.0 | 9.0 | 8.0 | | 4.0 | 9.0 | 7.5 | 9.0 | 9.0 | | | | | |
| | .175 | 9.0 | 9.0 | 8.0 | | 4.0 | 8.0 | 7.0 | 8.5 | 9.0 | | | | | |
| | .150 | 9.0 | 9.0 | 7.0 | | 4.0 | 8.5 | 7.5 | 8.5 | 9.0 | | | | | |
| | .125 | 9.0 | 9.0 | 7.0 | | 4.0 | 6.5 | 7.0 | 9.0 | 9.0 | | | | | |
| | .100 | 9.0 | 9.0 | 7.0 | | 4.0 | 6.5 | 6.0 | 8.5 | 9.0 | | | | | |
| | .080 | 8.0 | 9.0 | 5.5 | | 4.0 | 7.0 | 5.0 | 7.0 | 8.5 | | | | | |
| (±)-1,9bβ-Dihydro-3α-isopropyl-3-methyl-8-p-tolyl-5H—imidazo[1′,2′:1,2]pyrrolo[3,4-b]pyridine-2(3H),5-dione | 8.000 | 8.5 | 3.0 | 0.0 | 0.0 | 0.0 | 7.0 | 5.0 | 0.0 | 0.0 | 0.0 | 0.0 | 0.0 | 0.0 | 0.0 |
| | 1.000 | 0.0 | | 0.0 | 0.0 | 0.0 | 6.0 | 0.0 | 0.0 | 0.0 | 0.0 | 0.0 | 0.0 | 0.0 | 0.0 |
| | .500 | 0.0 | | 0.0 | 0.0 | 0.0 | 0.0 | 0.0 | 0.0 | 0.0 | 0.0 | 0.0 | 0.0 | 0.0 | 0.0 |
| | .250 | 0.0 | | 0.0 | 0.0 | 0.0 | 0.0 | 0.0 | 0.0 | 0.0 | 0.0 | 0.0 | 0.0 | 0.0 | 0.0 |
| | .125 | 0.0 | | 0.0 | 0.0 | 0.0 | 0.0 | 0.0 | 0.0 | 0.0 | 0.0 | 0.0 | 0.0 | 0.0 | 0.0 |
| | .063 | 0.0 | | 0.0 | 0.0 | 0.0 | 0.0 | 0.0 | 0.0 | 0.0 | | | | | |
| (±)-1,9bα-Dihydro-3α-isopropyl-3-methyl-8-p-tolyl-5H—imidazo[1′,2′:1,2]pyrrolo[3,4-b]-2(3H),5-dione | 8.000 | 0.0 | 0.0 | 0.0 | | 0.0 | 0.0 | 0.0 | 0.0 | 0.0 | | | | | |

EXAMPLE 56

Preemergence herbicidal evaluation of test compounds

The preemergence herbicidal activity of test compounds is demonstrated in the following tests, using the procedure of Example 54, excepting that compounds are evaluated at from 0.063 to 10.0 kg/ha, and wild oats and sunflowers are substituted for wheat, Williams variety, and cotton. Data obtained are reported in Table VIII.

TABLE VIII
PRE-EMERGENCE TESTS - RATES IN KG/HA

| Compound | RATE | BARN-YARD GR | GREEN FOX | P NUT-SEDGE | WILD OATS | QUACK GRASS | FLD BIND WD | MRN-GLRY SP | RAG WEED | VEL-VET LEAF | CORN FIELD | RICE, NATO | SUN-FLR XXX | S WHEAT ER | SOY-BEAN BR |
|---|---|---|---|---|---|---|---|---|---|---|---|---|---|---|---|
| 9bβ-(Benzyloxy)-3α-ethyl-1,9b-dihydro-3-methyl-5H—imidazo[1',2':1,2]pyrrolo[3,4-b]pyridine-2(3H),5-dione | 10.000 | 0.0 | 0.0 | 0.0 | 1.0 | | | 6.0 | 0.0 | 6.0 | 0.0 | 0.0 | | | |
| | 1.000 | 0.0 | 0.0 | 0.0 | 0.0 | | | 0.0 | 0.0 | 0.0 | 0.0 | 0.0 | | | |
| | .500 | 0.0 | 0.0 | 0.0 | 0.0 | | | 0.0 | 0.0 | 0.0 | 0.0 | 0.0 | | | |
| | .250 | 0.0 | 0.0 | 0.0 | 0.0 | | | 0.0 | 0.0 | 0.0 | 0.0 | 0.0 | | | |
| | .125 | 0.0 | 0.0 | 0.0 | 0.0 | | | 0.0 | 0.0 | 0.0 | 0.0 | 0.0 | | | |
| | .063 | 0.0 | 0.0 | 0.0 | 0.0 | | | 0.0 | 0.0 | 0.0 | 0.0 | 0.0 | | | |
| 9bα-(Benzyloxy)-3α-ethyl-1,9b-dihydro-3-methyl-5H—imidazo[1',2':1,2]pyrrolo[3,4-b]pyridine-2(3H),5-dione | 10.000 | 5.0 | 8.0 | 7.0 | 7.0 | | | 7.0 | 0.0 | 8.0 | 0.0 | 5.0 | | | |
| | 1.000 | 0.0 | 0.0 | 0.0 | 0.0 | | | 0.0 | 0.0 | 0.0 | 0.0 | 0.0 | | | |
| | .500 | 0.0 | 0.0 | 0.0 | 0.0 | | | 0.0 | 0.0 | 0.0 | 0.0 | 0.0 | | | |
| | .250 | 0.0 | 0.0 | 0.0 | 0.0 | | | 0.0 | 0.0 | 0.0 | 0.0 | 0.0 | | | |
| | .125 | 0.0 | 0.0 | 0.0 | 0.0 | | | 0.0 | 0.0 | 0.0 | 0.0 | 0.0 | | | |
| | .063 | 0.0 | 0.0 | 0.0 | 0.0 | | | 0.0 | 0.0 | 0.0 | 0.0 | 0.0 | | | |
| 3α-Ethyl-1,9b-dihydro-3-methyl-9bα-(2-propynyloxy)-5H—imidazo[1',2':1,2]-pyrrolo[3,4-b]pyridine-2(3H),5-dione | 10.000 | 0.0 | 0.0 | 0.0 | 0.0 | | | 0.0 | 0.0 | 0.0 | 0.0 | 0.0 | | | |
| | 1.000 | 0.0 | 0.0 | 0.0 | 0.0 | | | 0.0 | 0.0 | 0.0 | 0.0 | 0.0 | | | |
| | .500 | 0.0 | 0.0 | 0.0 | 0.0 | | | 0.0 | 0.0 | 0.0 | 0.0 | 0.0 | | | |
| | .250 | 0.0 | 0.0 | 0.0 | 0.0 | | | 0.0 | 0.0 | 0.0 | 0.0 | 0.0 | | | |
| | .125 | 0.0 | 0.0 | 0.0 | 0.0 | | | 0.0 | 0.0 | 0.0 | 0.0 | 0.0 | | | |
| | .063 | 0.0 | 0.0 | 0.0 | 0.0 | | | 0.0 | 0.0 | 0.0 | 0.0 | 0.0 | | | |
| 1,9b-Dihydro-3α-isopropyl-9bα-methoxy-3-methyl-5H—imidazo[1',2':1,2]pyrrolo[3,4-b]pyridine-2(3H),5-dione | 8.000 | 9.0 | 9.0 | 9.0 | 8.0 | 9.0 | 9.0 | 8.0 | 9.0 | 8.0 | 8.0 | 9.0 | 8.0 | 9.0 | |
| | .500 | 2.0 | 9.0 | 9.0 | 9.0 | 9.0 | 9.0 | 9.0 | 1.0 | 8.0 | 2.0 | 9.0 | 6.0 | 9.0 | |
| | .250 | 1.0 | 8.0 | 9.0 | 7.0 | 9.0 | 9.0 | 9.0 | 0.0 | 9.0 | 2.0 | 9.0 | 1.0 | 8.0 | |
| | .125 | 0.0 | 7.0 | 8.0 | 4.0 | 1.0 | 9.0 | 8.0 | 0.0 | 9.0 | 0.0 | 7.0 | 1.0 | 5.0 | |
| | .063 | 0.0 | 1.0 | 0.0 | 0.0 | 0.0 | 8.0 | 7.0 | 0.0 | 2.0 | 0.0 | 4.0 | | | |
| 1,9b-Dihydro-3α-isopropyl-3-methyl-9bα-propoxy-5H—imidazo[1',2':1,2]pyrrolo[3,4-b]pyridine-2(3H),5-dione | 8.000 | 9.0 | 9.0 | 9.0 | 9.0 | 9.0 | 9.0 | 8.0 | 8.0 | 9.0 | 9.0 | 9.0 | 8.0 | 9.0 | |
| | .500 | 7.0 | 9.0 | 8.0 | 8.0 | 8.0 | 9.0 | 9.0 | 6.0 | 9.0 | 7.0 | 9.0 | 6.0 | 9.0 | |
| | .250 | 1.0 | 9.0 | 8.0 | 3.0 | 8.0 | 9.0 | 4.0 | 3.0 | 9.0 | 2.0 | 7.0 | 2.0 | 8.0 | |
| | .125 | 0.0 | 4.0 | 7.0 | 0.0 | 7.0 | 9.0 | | 0.0 | 3.0 | 2.0 | 4.0 | 2.0 | 6.0 | |
| | .063 | 0.0 | 1.0 | 7.0 | 0.0 | 4.0 | 8.0 | 0.0 | 0.0 | 8.0 | 0.0 | 0.0 | 0.0 | 0.0 | |
| cis-and/or trans-1,9b-Dihydro-3-isopropyl-3-methyl-9b-(2-propynylamino)-5H—imidazo[1',2':1,2](and/or [2',1',5,1)pyrrolo[3,4-b]-pyridine-2(3H),5-dione | 8.000 | 6.0 | 9.0 | 7.0 | 9.0 | 9.0 | 8.0 | 0.0 | 6.0 | 3.0 | 0.0 | 0.0 | 0.0 | 0.0 | |
| | .500 | 0.0 | 0.0 | 0.0 | 0.0 | 0.0 | | 8.0 | 0.0 | 8.0 | 0.0 | 0.0 | 0.0 | 0.0 | |
| | .250 | 0.0 | 0.0 | 0.0 | 0.0 | 0.0 | | 0.0 | 0.0 | 0.0 | 0.0 | 0.0 | 0.0 | 0.0 | |
| | .125 | 0.0 | 0.0 | 0.0 | 0.0 | 0.0 | | 0.0 | 0.0 | 0.0 | 0.0 | 0.0 | 0.0 | 0.0 | |
| | .063 | 0.0 | 0.0 | 0.0 | 0.0 | 0.0 | | 0.0 | 0.0 | 0.0 | 0.0 | 0.0 | 0.0 | 0.0 | |
| 9bα-{[p-(Dimethylamino)-benzyl]oxy}-1,9b-dihydro-3α-isopropyl-3-methyl-5H—imidazo[1',2':1,2]pyrrolo[3,4-b]pyridine-2(3H),5-dione | 8.000 | 8.0 | 9.0 | 9.0 | 9.0 | 9.0 | 9.0 | 8.0 | 9.0 | 9.0 | 7.0 | 7.0 | 6.0 | 8.0 | |
| | .500 | 3.0 | 7.0 | 9.0 | 7.0 | 9.0 | 9.0 | 9.0 | 0.0 | 9.0 | 7.0 | 6.0 | 1.0 | 6.0 | |
| | .250 | 2.0 | 1.0 | 7.0 | 0.0 | 1.0 | 9.0 | 4.0 | 0.0 | 3.0 | 7.0 | 1.0 | 1.0 | 5.0 | |
| | .125 | 1.0 | 0.0 | 3.0 | 0.0 | 0.0 | 9.0 | 0.0 | 0.0 | 1.0 | 6.0 | 1.0 | 1.0 | 2.0 | |
| | .063 | 0.0 | 0.0 | 0.0 | 0.0 | 0.0 | 8.0 | 0.0 | 0.0 | 0.0 | 0.0 | 0.0 | 0.0 | 0.0 | |
| 9bα-Amino-1,9b-dihydro-3α-isopropyl-3-methyl-5H—imidazo[1',2':1,2]pyrrolo[3,4-b]-pyridine-2(3H),5-dione | 8.000 | 9.0 | 9.0 | 9.0 | 9.0 | 9.0 | 9.0 | 9.0 | 8.0 | 9.0 | 9.0 | 7.0 | 6.0 | 9.0 | |
| | .500 | 1.0 | 5.0 | 8.0 | 7.0 | 9.0 | 9.0 | 8.0 | 4.0 | 8.0 | 7.0 | 7.0 | 1.0 | 8.0 | |
| | .250 | 0.0 | 5.0 | 3.0 | 6.0 | 7.0 | 8.0 | 7.0 | 4.0 | 7.0 | 7.0 | 2.0 | 3.0 | 7.0 | |
| | .125 | 0.0 | 0.0 | 2.0 | 3.0 | 2.0 | 2.0 | 4.0 | | 3.0 | 7.0 | 1.0 | 3.0 | 7.0 | |
| | .063 | 0.0 | 0.0 | 1.0 | 1.0 | 1.0 | 1.0 | 6.0 | | 1.0 | 4.0 | 1.0 | 1.0 | 3.0 | |
| 9bα-(Benzyloxy)-1,9b-dihydro-3α-isopropyl-3-methyl-5H—imidazo[1',2':1,2]pyrrolo[3,4-b]pyridine-2(3H),5-dione | 8.000 | 9.0 | 9.0 | 9.0 | 9.0 | 9.0 | 9.0 | 9.0 | 9.0 | 9.0 | 6.0 | 9.0 | 5.0 | 9.0 | |
| | .500 | 4.0 | 7.0 | 9.0 | 8.0 | 9.0 | 9.0 | 6.0 | 0.0 | 8.0 | 6.0 | 8.0 | 4.0 | 7.0 | |
| | .250 | 3.0 | 4.0 | 7.0 | 0.0 | 7.0 | 9.0 | 6.0 | 0.0 | 8.0 | 4.0 | 7.0 | 1.0 | 6.0 | |
| | .125 | 2.0 | 3.0 | 6.0 | 0.0 | 7.0 | 9.0 | 2.0 | 0.0 | 7.0 | 4.0 | 0.0 | 1.0 | 6.0 | |
| | .063 | 1.0 | 1.0 | 1.0 | 0.0 | 3.0 | 8.0 | 0.0 | 0.0 | 1.0 | 4.0 | 4.0 | 1.0 | 3.0 | |

TABLE VIII-continued
PRE-EMERGENCE TESTS - RATES IN KG/HA

| Compound | RATE | BARN-YARD GR | GREEN FOX | P NUT-SEDGE | WILD OATS | QUACK GRASS | FLD BIND WD | MRN-GLRY SP | RAG WEED | VEL-VET LEAF | CORN FIELD | RICE, NATO | SUN-FLR XXX | S WHEAT ER | SOY-BEAN BR |
|---|---|---|---|---|---|---|---|---|---|---|---|---|---|---|---|
| 9bα(and/orβ)-Ethoxy-1,9b-dihydro-3α-isopropyl-3-methyl-5H—imidazo[1',2':1,2]pyrrolo[3,4-b]pyridine-2(3H),5-dione | .500 | 6.0 | 6.0 | 8.0 | 9.0 | 9.0 | 9.0 | 7.0 | 0.0 | 9.0 | 9.0 | 7.0 | 8.0 | 9.0 | |
| | .250 | 2.0 | 3.0 | 8.0 | 7.0 | 9.0 | 9.0 | 4.0 | 0.0 | 6.0 | 7.0 | 6.0 | 2.0 | 9.0 | |
| | .125 | 2.0 | 0.0 | 7.0 | 1.0 | 9.0 | 9.0 | | 0.0 | 6.0 | 4.0 | 5.0 | 1.0 | 8.0 | |
| | .063 | 0.0 | 0.0 | 1.0 | 0.0 | 2.0 | 8.0 | | 0.0 | 1.0 | 4.0 | 3.0 | 0.0 | 7.0 | |
| 2-Isopropyl-7-methoxy-2-methyl-5H—imidazo[1',2':1,2]pyrrolo[3,4-b]pyridine-3(2H),5-dione and 3-isopropyl-7-methoxy-3-methyl-5H—imidazo[1',2':1,2]pyrrolo-2(3H),5-dione | | | | | | | | 0.0 | | | | | | | |
| 8-Allyloxy)-2-isopropyl-2-methyl-5H—imidazo[1',2':1,2]pyrrolo[3,4-b]pyridine-3(2H),5-dione | .500 | 9.0 | | 9.0 | 9.0 | 9.0 | 9.0 | 8.0 | 6.0 | 8.0 | 9.0 | 9.0 | 9.0 | 8.0 | 8.0 |
| | .250 | 2.0 | | 9.0 | 7.0 | 9.0 | 5.0 | 8.0 | 5.0 | 8.0 | 8.0 | 8.0 | 8.0 | 7.0 | 7.0 |
| | .125 | 1.0 | | 9.0 | 2.0 | 9.0 | 5.0 | 6.0 | 2.0 | 7.0 | 6.0 | 4.0 | 7.0 | 6.0 | 4.0 |
| | .063 | 0.0 | | 8.0 | 0.0 | 8.0 | 2.0 | 2.0 | 1.0 | 2.0 | 5.0 | 3.0 | 6.0 | 2.0 | 0.0 |
| 2-Isopropyl-2,8-dimethyl-5H—dihydro[1',2':1,2]pyrrolo[3,4-b]pyridine-3(2H),5-dione | .500 | 9.0 | | 9.0 | 9.0 | 9.0 | 9.0 | 9.0 | 9.0 | 9.0 | 9.0 | 9.0 | 9.0 | 9.0 | 9.0 |
| | .250 | 9.0 | | 9.0 | 9.0 | 9.0 | 9.0 | 9.0 | 9.0 | 9.0 | 9.0 | 9.0 | 9.0 | 9.0 | 9.0 |
| | .125 | 9.0 | | 9.0 | 9.0 | 9.0 | 9.0 | 8.0 | 9.0 | 9.0 | 9.0 | 9.0 | 9.0 | 9.0 | 9.0 |
| | .063 | 8.0 | | 9.0 | 9.0 | 9.0 | 9.0 | 8.0 | 9.0 | 9.0 | 9.0 | 9.0 | 9.0 | 9.0 | 7.0 |
| 7-Chloro-1,9bβ-dihydro-3α-isopropyl-3-methyl-5H—imidazo[1',2':1,2]pyrrolo[3,4-b]pyridine-2(3H),5-dione | .500 | 9.0 | | 9.0 | 9.0 | 9.0 | 9.0 | 9.0 | 9.0 | 8.0 | 5.0 | 9.0 | 9.0 | 8.0 | 4.0 |
| | .250 | 9.0 | | 9.0 | 2.0 | 9.0 | 5.0 | 8.0 | 9.0 | 8.0 | 5.0 | 8.0 | 8.0 | 6.0 | 3.0 |
| | .125 | 6.0 | | 8.0 | 1.0 | 9.0 | 5.0 | 6.0 | 9.0 | 7.0 | 6.0 | 7.0 | 7.0 | 4.0 | 2.0 |
| | .063 | 2.0 | | 7.0 | 0.0 | 8.0 | 7.0 | 2.0 | 8.0 | 5.0 | 0.0 | 5.0 | 4.0 | 1.0 | 2.0 |
| 2-Isopropyl-2-methyl-5H—furo[2,3-b]imidazo[2',1':5,1]pyrrolo[3,4-b]pyridine-3(2H),5-dione | .500 | 9.0 | | 9.0 | 9.0 | 9.0 | 9.0 | 9.0 | 9.0 | 9.0 | 9.0 | 9.0 | 9.0 | 7.0 | 6.0 |
| | .250 | 5.0 | | 8.9 | 7.0 | 9.0 | 9.0 | 9.0 | 9.0 | 9.0 | 9.0 | 8.0 | 9.0 | 3.0 | 3.0 |
| | .125 | 6.0 | | 8.6 | 6.0 | 9.0 | 9.0 | 9.0 | 9.0 | 6.0 | 9.0 | 7.0 | 9.0 | 2.0 | 2.0 |
| | .063 | 2.0 | | 9.0 | 2.0 | 3.0 | 9.0 | 2.0 | 9.0 | 7.0 | 6.0 | 4.0 | 9.0 | 1.0 | 2.0 |
| 1,9bα-Dihydro-3α-isopropyl-3-methyl-2-thio-5H—imidazo[1',2':1,2]pyrrolo[3,4-b]pyridine-2(3H),5-dione | .500 | 8.0 | | 7.0 | 2.0 | 7.0 | 9.0 | 6.0 | 6.0 | 8.0 | 2.0 | 3.0 | 7.0 | 7.0 | 2.0 |
| | .250 | 6.0 | | 5.0 | 0.0 | 5.0 | 8.0 | 7.0 | 2.0 | 8.0 | 2.0 | 2.0 | 2.0 | 6.0 | 2.0 |
| | .125 | 4.0 | | 1.0 | 0.0 | 7.0 | 7.0 | 2.0 | 1.0 | 7.0 | 2.0 | 1.0 | 1.0 | 4.0 | 1.0 |
| | .063 | 0.0 | | 0.0 | 0.0 | 2.0 | 7.0 | 0.0 | 0.0 | 4.0 | 2.0 | 1.0 | 0.0 | 2.0 | 0.0 |
| 1,9bα(and 9bβ-Dihydro-3α-isopropyl-3,7-dimethyl-5H—imidazo[1',2':1,2]pyrrolo[3,4-b]pyridine-2(3H),5-dione | .250 | 9.0 | | 9.0 | 9.0 | 9.0 | 9.0 | 8.0 | 9.0 | 9.0 | 2.8 | 9.0 | 8.0 | 9.0 | 5.0 |
| | .500 | 9.0 | | 8.9 | 9.0 | 9.0 | 9.0 | 8.0 | 9.0 | 9.0 | 1.4 | 9.0 | 8.0 | 8.0 | 4.0 |
| | .375 | 9.0 | | 8.6 | 7.0 | 7.0 | 9.0 | 8.0 | 9.0 | 8.9 | 1.1 | 9.0 | 8.0 | 7.0 | |
| | .250 | 9.0 | | 8.2 | 8.0 | 8.8 | 9.0 | 7.0 | 8.8 | 8.5 | 0.3 | 9.0 | 7.0 | 4.8 | 3.0 |
| | .125 | 9.0 | | 6.8 | 6.0 | 6.0 | 9.0 | 7.0 | 8.5 | 9.0 | 0.0 | 8.0 | 6.0 | 3.0 | 0.0 |
| (R)-(−)-1,9bβ(and α)-Dihydro-3β-isopropyl-3-methyl-5H—imidazo[1',2':1,2]pyrrolo[3,4-b]pyridine-2(3H),5-dione | .080 | 9.0 | 9.0 | 5.5 | | 1.0 | 9.0 | 8.0 | 8.8 | 9.0 | | | | | |
| | .150 | 9.0 | 9.0 | 8.0 | | 8.0 | 9.0 | 8.0 | 9.0 | 9.0 | | | | 4.0 | |
| | .125 | 9.0 | 9.0 | 8.0 | | 5.0 | 9.0 | 8.0 | 9.0 | 9.0 | | | | | |
| | .100 | 9.0 | 9.0 | 8.0 | | 3.5 | 9.0 | 8.0 | 9.0 | 9.0 | | | | | |
| | .080 | 9.0 | 9.0 | 7.5 | | 1.5 | 9.0 | 8.0 | 9.0 | 9.0 | | | | | |
| 7-(Allyloxy)-1,9bβ-dihydro-3α-isopropyl-3-methyl-5H—imidazo[1',2':1,2]pyrrolo[3,4-b]pyridine-2(3H),5-dione | .063 | | | | | | | | | | | | | 0.0 | |
| | .500 | 9.0 | | 4.0 | 5.0 | 9.0 | 9.0 | 9.0 | 7.0 | 9.0 | 6.0 | 8.0 | 7.0 | 8.0 | 2.0 |
| | .250 | 9.0 | | 1.0 | 2.0 | 9.0 | 9.0 | 2.0 | 6.0 | 8.0 | 4.0 | 8.0 | 4.0 | 3.0 | 0.0 |
| | .125 | 8.0 | | 0.0 | 0.0 | 9.0 | 8.0 | | 2.0 | 6.0 | 2.0 | 5.0 | 3.0 | 0.0 | 0.0 |
| | .063 | 5.0 | | 0.0 | 0.0 | 3.0 | 2.0 | 0.0 | 0.0 | 2.0 | 0.0 | 3.0 | 2.0 | 4.0 | 0.0 |
| 1,9bα-Dihydro-3α-isopropyl-3,7-dimethyl-5H—imidazo[1',2':1,2]pyrrolo[3,4-b]pyridine-2(3H),5-dione | .250 | | | | | | | | | | | | | | | |
| | .150 | 9.0 | 9.0 | 5.5 | | 3.0 | 9.0 | 8.0 | 9.0 | 9.0 | | | | | |
| | .125 | 9.0 | 9.0 | 6.0 | | 3.0 | 8.5 | 8.0 | 9.0 | 9.0 | | | | 4.0 | |

TABLE VIII-continued

PRE-EMERGENCE TESTS - RATES IN KG/HA

| Compound | RATE | BARN-YARD GR | GREEN FOX | P NUT-SEDGE | WILD OATS | QUACK GRASS | FLD BIND WD | MRN-GLRY SP | RAG WEED | VEL-VET LEAF | CORN FIELD | RICE, NATO | SUN-FLR XXX | S WHEAT ER | SOY-BEAN BR |
|---|---|---|---|---|---|---|---|---|---|---|---|---|---|---|---|
| dine-2(3H),5-dione | .100 | 9.0 | 9.0 | 5.0 | | 0.0 | 9.0 | 7.5 | 8.0 | 9.0 | | | | | |
|  | .080 | 8.5 | 8.5 | 3.5 | | 0.0 | 7.5 | 8.0 | 8.0 | 9.0 | | | | | |
| (3R,9bR)-trans-(−)-1,9b-Dihydro-3-isopropyl-3,7-dimethyl-5H—imidazo[1′,2′:1,2]pyrrolo[3,4-b]pyridine-2(3H),5-dione | .063 | | | | | | | | | | | | | 0.0 | |
|  | .750 | | | | | | | | | | 3.0 | | | | |
|  | .150 | 9.0 | 9.0 | 7.5 | | 8.0 | 9.0 | 8.0 | 9.0 | 9.0 | | | | | |
|  | .125 | 9.0 | 9.0 | 6.5 | | 3.5 | 9.0 | 8.0 | 9.0 | 9.0 | | | | 5.0 | |
|  | .100 | 9.0 | 9.0 | 5.0 | | 3.0 | 9.0 | 8.0 | 8.5 | 9.0 | | | | | |
|  | .080 | 9.0 | 8.5 | 4.0 | | 1.5 | 9.0 | 8.0 | 8.0 | 9.0 | | | | | |
| (3R,9bS)-cis-(+)-1,9b-Dihydro-3-isopropyl-3,7-dimethyl1H—imidazo[1′,2′:1,2]pyrrolo[3,4-b]pyridine-2(3H),5-dione | .063 | | | | | | | | | | | | | 7.0 | |
|  | .250 | 9.0 | 9.0 | 9.0 | | 9.0 | 9.0 | 7.0 | 8.0 | 9.0 | 0.0 | | | | |
|  | .150 | 9.0 | 8.5 | 9.0 | | 7.5 | 9.0 | 8.0 | 8.0 | 9.0 | | | | 6.0 | |
|  | .125 | 9.0 | 8.0 | 8.5 | | 6.0 | 9.0 | 6.0 | 7.5 | 9.0 | | | | | |
|  | .100 | 9.0 | 7.0 | 8.5 | | 2.5 | 9.0 | 5.5 | 6.5 | 9.0 | | | | | |
| (±)-1,9β-Dihydro-3α-isopropyl-3-methyl-8-p-tolyl-5H—imidazo[1′,2′:pyrrolo[3,4-b]pyridine-2(3H),5-dione | .080 | 0.0 | 2.0 | 8.0 | 9.0 | 0.0 | 0.0 | 0.0 | 1.0 | 1.0 | 0.0 | 0.0 | 0.0 | 0.0 | 0.0 |
|  | 8.000 | 0.0 | | 0.0 | 0.0 | 0.0 | 0.0 | 0.0 | 0.0 | 0.0 | 0.0 | 0.0 | 0.0 | 0.0 | 0.0 |
|  | .500 | 0.0 | | 0.0 | 0.0 | 0.0 | 0.0 | 0.0 | 0.0 | 0.0 | 0.0 | 0.0 | 0.0 | 0.0 | 0.0 |
|  | .250 | 0.0 | | 0.0 | 0.0 | 0.0 | 0.0 | 0.0 | 0.0 | 0.0 | | | | | |
|  | .125 | 0.0 | | 0.0 | 0.0 | 0.0 | 0.0 | 0.0 | 0.0 | 0.0 | | | | | |
|  | .063 | 0.0 | | 0.0 | 0.0 | 0.0 | 0.0 | 0.0 | 0.0 | 0.0 | | | | | |
| (±)-1,9bα-Dihydro-3α-isopropyl-3-methyl-8p-tolyl-5H—imidazo[1′,2′:1,2]pyrrolo[3,4-b]-2(3H),5-dione | 8.000 | 3.0 | 8.0 | 8.0 | 9.0 | 8.0 | 5.0 | 8.0 | 0.0 | 6.0 | | | | | |

What is claimed is:

1. A compound having the structure:

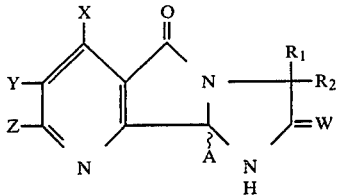

wherein $R_1$ and $R_2$ each represent $C_1$–$C_3$ alky or cyclopropyl, with the proviso that the sum of the number of carbon atoms in $R_1$ and $R_2$ is together with the carbon to which they are attached, they may form a $C_3$–$C_6$ cycloalkyl ring optionally substituted with methyl;

W is oxygen or sulfur;

A is hydrogen, hydroxyl, $C_3$–$C_6$ alkenyloxy, $C_3$–$C_6$ alkynyloxy, $C_1$–$C_6$ alkylthio, $NR_{13}R_{14}$ or $C_1$–$C_6$ alkoxy optionally substituted with phenyl, halophenyl, $C_1$–$C_3$ alkylphenyl, $C_1$–$C_3$ alkoxyphenyl or di-$C_1$–$C_3$ alkylaminophenyl;

$R_{13}$ is hydrogen, $C_1$–$C_4$ alkyl optionally substituted with phenyl, halophenyl, $C_1$–$C_3$ alkylphenyl or $C_1$–$C_3$ alkoxyphenyl;

$R_{14}$ is hydrogen or $C_1$–$C_4$ alkyl;

X is hydrogen, halogen or methyl;

Y and Z are each hydrogen, halogen, $C_1$–$C_6$ alkyl, $C_1$–$C_4$ hydroxyalkyl, $C_1$–$C_6$ alkoxy, $C_1$–$C_4$ alkylthio, phenoxy, $C_1$–$C_4$ haloalkyl, $OCF_2CHF_2$, $OCF_3$, $OCHF_2$, nitro, cyano, $NR_4R_5$, $C_3$–$C_8$ straight or branched alkenyloxy optionally substituted with one to three halogens, $C_3$–$C_8$ straight or branched alkynyloxy optionally substituted with one to three halogens, or phenyl optionally substituted with one $C_1$–$C_4$ alkyl, $C_1$–$C_4$ alkoxy or halogen;

$R_4$ is hydrogen or $C_1$–$C_4$ alkyl;

$R_5$ is $C_1$–$C_4$ alkyl; And, when taken together, Y and Z may form a ring in which YZ is represented by (1) the structure: —$(CH_2)_n$—, where n is an integer of 2, 3 or 4, provided that X is hydrogen; or (2) by the structure:

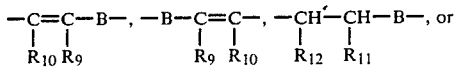

where, L, M, $R_7$ and $R_8$ each represent hydrogen, halogen, $C_1$–$C_4$ alkyl, $C_1$–$C_4$ alkoxy, $C_1$–$C_4$ alkylthio, $C_1$–$C_4$ alkylsulfonyl, $C_1$–$C_4$ haloalkyl, $NO_2$, CN, phenyl, phenoxy, amino, $OCF_3$, $OCHF_2$, $OCF_2CHF_2$, $C_1$–$C_4$ alkylamino, dialkyl($C_1$–$C_4$)amino, chlorophenyl, methylphenyl, $C_3$–$C_8$ straight or branched alkenyloxy optionally substituted with one to three halogens, $C_3$–$C_8$ straight or branched alkynyloxy optionally substituted with one to three halogens, or phenoxy substituted with one Cl, $CF_3$, $NO_2$ or $CH_3$ group, with the proviso that only one of L, M, $R_7$ or $R_8$ may represent a substituent other than hydrogen, halogen, $C_1$–$C_4$ alkyl or $C_1$–$C_4$ alkoxy; or (3) by the structures:

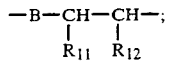

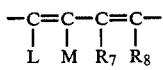

where B is oxygen or sulfur; $R_9$ and $R_{10}$ each represent hydrogen, halogen, phenyl, or $C_1$–$C_4$ alkyl; $R_{11}$ and $R_{12}$ each represent hydrogen, $C_1$–$C_4$ alkyl or phenyl;

and when $R_1$ and $R_2$ are not the same, the cis- or trans-isomers or mixtures thereof or the optical isomers (cis- or trans- or mixtures thereof).

2. A compound according to claim 1, wherein A, $R_1$, $R_2$, W and X are as defined in said claim 1 above; Y and Z each, independently, represent hydrogen, halogen, $C_1$–$C_6$ alkyl, $C_1$–$C_6$ alkoxy, CN, $NO_2$, $OCF_3$, $OCHF_2$, $OCF_2CHF_2$, phenoxy, $C_1$–$C_4$ haloalkyl, $C_1$–$C_4$ alkylthio, $C_1$–$C_4$ hydroxyalkyl, $NR_4R_5$, $C_3$–$C_8$ straight or branched alkenyloxy optionally substituted with one to three halogens, $C_3$–$C_8$ straight or branched alkynyloxy optionally substituted with one to three halogens, or phenyl optionally substituted with one $C_1$–$C_4$ alkyl, $C_1$–$C_4$ alkoxy or halogen; $R_4$ is hydrogen or $C_1$–$C_4$ alkyl; $R_5$ is $C_1$–$C_4$ alkyl; and when taken together Y and Z may form a ring in which YZ are represented by the structure: —$(CH_2)_n$—, where n is an integer of 2, 3 or 4 provided that X is hydrogen; and when $R_1$ and $R_2$ are not the same, the cis- or trans-isomers or mixtures thereof or the optical isomers (cis- or trans- or mixtures thereof).

3. A compound according to claim 1, having the structure:

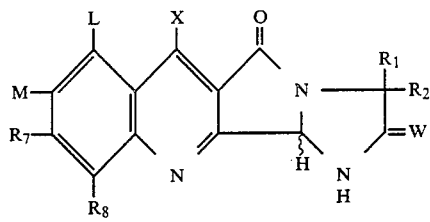

wherein A, $R_1$, $R_2$, W and X, are as defined above in said claim 1, and L, M, $R_7$ and $R_8$ represent hydrogen, halogen, $C_1$–$C_4$ alkyl, $C_1$–$C_4$ alkoxy, $C_1$–$C_4$ alkylthio, $C_1$–$C_4$ alkylsulfonyl, $C_1$–$C_4$ haloalkyl, $NO_2$, CN, phenyl, phenoxy, amino, $CF_3$, $OCHF_2$, $OCF_2CHF_2$, $C_1$–$C_4$ alkylamino, dialkyl($C_1$–$C_4$)amino, chlorophenyl, methylphenyl, $C_3$–$C_8$ straight or branched alkenyloxy optionally substituted with one to three halogens, $C_3$–$C_8$ straight or branched alkynyloxy optionally substituted with one to three halogens, or phenoxy substituted with one Cl, $CF_3$, $NO_2$ or $CH_3$ group, with the proviso that only one of L, M, $R_7$ or $R_8$, may represent a substituent other than hydrogen, halogen, $C_1$–$C_4$ alkyl or $C_1$–$C_4$ alkoxy; and when $R_1$ and $R_2$ are not the same, the cis- or trans-isomers or mixtures thereof or the optical isomers (cis- or trans- or mixtures thereof).

4. A compound according to claim 1, having the structure:

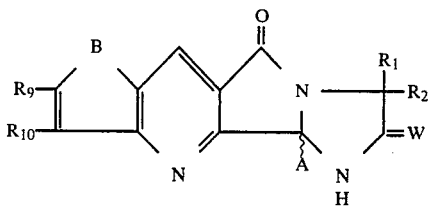

wherein A, $R_1$, $R_2$, W and B, are as defined above in said claim 1; $R_9$ and $R_{10}$ each represent hydrogen, halogen, $C_1$–$C_4$ alkyl or phenyl; and when $R_1$ and $R_2$ are not the same, the cis- or trans-isomers or mixtures thereof or the optical isomers (cis- or trans- or mixture thereof).

5. A compound according to claim 1, having the structure:

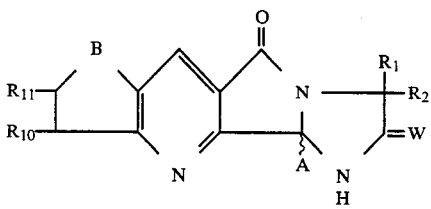

wherein A, $R_1$, $R_2$, W and B, are as defined above in said claim 1; $R_{11}$ and $R_{12}$ each represent hydrogen, $C_1$–$C_4$ alkyl or phenyl; and when $R_1$ and $R_2$ are not the same, the cis- or trans-isomers or mixtures thereof or the optical isomers (cis- or trans- or mixtures thereof).

6. A compound according to claim 1, having the structure:

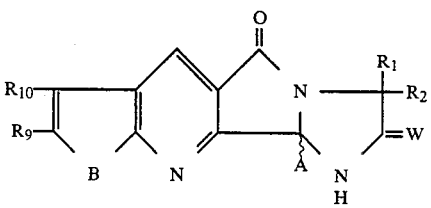

wherein A, $R_1$, $R_2$, W and B, are as defined above in said claim 1; $R_9$ and $R_{10}$ each represent hydrogen, halogen, $C_1$–$C_4$ alkyl or phenyl; and when $R_1$ and $R_2$ are not the same, the cis- or trans-isomers or mixtures thereof or the optical isomers (cis- or trans- or mixtures thereof).

7. A compound according to claim 1, having the structure:

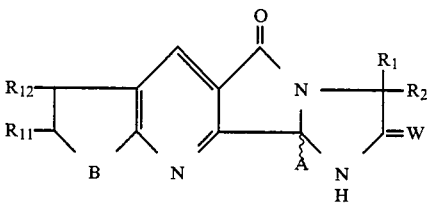

wherein A, $R_1$, $R_2$, W and B, are as defined above in said claim 1; $R_{11}$ and $R_{12}$ each represent hydrogen, $C_1$–$C_4$ alkyl or phenyl; and when $R_1$ and $R_2$ are not the same, the cis- or trans-isomers of mixtures thereof or the optical isomers (cis- or trans- or mixtures thereof).

8. A compound according to claim 1, 1,9bβ-dihydro-3α-isopropyl-3,7-dimethyl-5H-imidazo[1′,2′:1,2]pyrrolo[3,4-b]pyridine-2(3H),5-dione or 1,9bα-dihydro-3α-isopropyl-3,7-dimethyl-5H-imidazo[1′,2′:1,2]pyrrolo[3,4-b]pyridine-2(3H),5-dione or mixtures or optical isomers thereof.

9. A compound according to claim 1, 7-ethyl-1,9bα-dihydro-3α-isopropyl-3-methyl-5H-imidazo[1′,2′:1.2-]pyrrolo[3,4-b]pyridine-2(3H),5-dione or 7-ethyl-1,9bβ-dihydro-3α-isopropyl-3-methyl-5H-imidazo[1′,2′:1,2-]pyrrolo[3,4b]pyridine-2(3H),5-dione or mixtures or optical isomers thereof.

10. A compound according to claim 1, 1,9b-dihydro-3α-isopropyl-3-methyl-9bα-propoxy-5H-imidazo[1′,2′:1,2]pyrrolo[3,4-b]pyridine-2(3H),5-dione.

11. A method for the control of undesirable monocotyledonous and dicotyledonous plant species comprising: applying to the foliage of said plants or to soil containing seeds or other propagating organs thereof, a herbicidally effective amount of a compound having the structure:

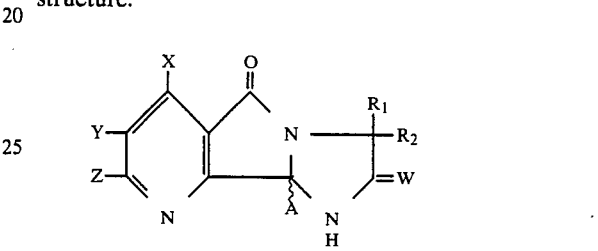

wherein $R_1$ and $R_2$ each represent $C_1$–$C_3$ alkyl or cyclopropyl, with the proviso that the sum of the number of carbon atoms in $R_1$ and $R_2$ is 2 to 5; and when $R_1$ and $R_2$ are taken together with the carbon to which they are attached, they may form a $C_3$–$C_6$ cycloalkyl ring optionally substituted with methyl;

W is oxygen or sulfur;

A is hydrogen, hydroxyl, $C_3$–$C_6$ alkenyloxy, $C_3$–$C_6$ alkynyloxy, $C_1$–$C_6$ alkylthio, $NR_{13}R_{14}$ or $C_1$–$C_6$ alkoxy optionally substituted with phenyl, halophenyl, $C_1$–$C_3$ alkylphenyl, $C_1$–$C_3$ alkoxyphenyl or di-$C_1$–$C_3$ alkylaminophenyl;

$R_{13}$ is hydrogen, $C_1$–$C_4$ alkyl optionally substituted with phenyl, halophenyl, $C_1$–$C_3$ alkylphenyl or $C_1$–$C_3$ alkoxyphenyl;

$R_{14}$ is hydrogen or $C_1$–$C_4$ alkyl;

X is hydrogen, halogen or methyl;

Y and Z are each hydrogen, halogen, $C_1$–$C_6$ alkyl, $C_1$–$C_4$ hydroxyalkyl, $C_1$–$C_6$ alkoxy, $C_1$–$C_4$ alkylthio, phenoxy, $C_1$–$C_4$ haloalkyl, $OCF_2$ $CHF_2$, $OCF_3$, $OCHF_2$, nitro, cyano, $NR_4R_5$, $C_3$–$C_8$ straight or branched alkenyloxy optionally substituted with one to three halogens, $C_3$–$C_8$ straight or branched alkynyloxy optionally substituted with one to three halogens, or phenyl optionally substituted with one $C_1$–$C_4$ alkyl, $C_1$–$C_4$ alkoxy or halogen;

$R_4$ is hydrogen or $C_1$–$C_4$ alkyl;

$R_5$ is $C_1$–$C_4$ alkyl; And, when taken together, Y and Z may form a ring in which YZ is represented by (1) the structure: —$(CH_2)_n$—, where n is an integer of 2, 3 or 4, provided that X is hydrogen; or (2) by the structure:

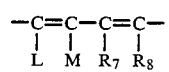

where, L, M, R$_7$ and R$_8$ each represent hydrogen, halogen, C$_1$-C$_4$ alkyl, C$_1$-C$_4$ alkoxy, C$_1$-C$_4$ alkylthio, C$_1$-C$_4$ alkylsulfonyl, C$_1$-C$_4$ haloalkyl, NO$_2$, CN, phenyl, phenoxy, amino, OCF$_3$, OCHF$_2$, OCF$_2$CHF$_2$, C$_1$-C$_4$ alkylamino, dialkyl(C$_1$-C$_4$)amino, chlorophenyl, methylphenyl, C$_3$-C$_8$ straight or branched alkenyloxy optionally substituted with one to three halogens, C$_3$-C$_8$ straight or branched alkynyloxy optionally substituted with one to three halogens, or phenoxy substituted with one Cl, CF$_3$, NO$_2$ or CH$_3$ group, with the proviso that only one of L, M, R$_7$ or R$_8$ may represent a substituent other than hydrogen, halogen, C$_1$-C$_4$ alkyl or C$_1$-C$_4$ alkoxy; or (3) by the structures:

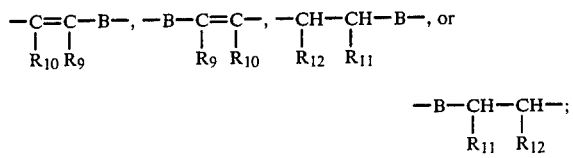

where B is oxygen or sulfur; R$_9$ and R$_{10}$ each represent hydrogen, halogen, phenyl, or C$_1$-C$_4$ alkyl; R$_{11}$ and R$_{12}$ each represent hydrogen, C$_1$-C$_4$ alkyl or phenyl;

and when R$_1$ and R$_2$ are not the same, the cis- or trans-isomers or mixtures thereof or the optical isomers (cis- or trans- or mixtures thereof).

12. A method according to claim 11, wherein A, R$_1$, R$_2$, W and X are as defined in said claim 1 above; Y and Z each, independently, represent hydrogen, halogen, C$_1$-C$_6$ alkyl, C$_1$-C$_6$ alkoxy, CN, NO$_2$, OCF$_3$, OCHF$_2$, OCF$_2$CHF$_2$, phenoxy, C$_1$-C$_4$ haloalkyl, C$_1$-C$_4$ alkylthio, C$_1$-C$_4$ hydroxyalkyl, NR$_4$R$_5$, C$_3$-C$_8$ straight or branched alkenyloxy optionally substituted with one to three halogens, C$_3$-C$_8$ straight or branched alkynyloxy optionally substituted with one to three halogens, or phenyl optionally substituted with one C$_1$-C$_4$ alkyl, C$_1$-C$_4$ alkoxy or halogen; R$_4$ is hydrogen or C$_1$-C$_4$ alkyl; R$_5$ is C$_1$-C$_4$ alkyl; and when taken together Y and Z may form a ring in which YZ are represented by the structure: —(CH$_2$)$_n$—, where n is an integer of 2, 3 or 4; and when R$_1$ and R$_2$ are not the same, the cis- or trans-isomers or mixtures thereof or the optical isomers (cis- and trans- or mixtures thereof).

13. A method according to claim 11, wherein said compound has the structure:

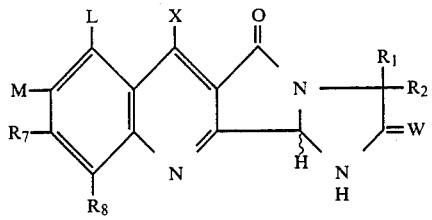

wherein A, R$_1$, R$_2$, W and X, are as defined above in said claim 1, and L, M, R$_7$ and R$_8$ represent hydrogen, halogen, C$_1$-C$_4$ alkyl, C$_1$-C$_4$ alkoxy, C$_1$-C$_4$ alkylthio, C$_1$-C$_4$ alkylsulfonyl, C$_1$-C$_4$ haloalkyl, NO$_2$, CN, phenyl, phenoxy, amino, CF$_3$, OCHF$_2$, OCF$_2$CHF$_2$, C$_1$-C$_4$ alkylamino, dialkyl(C$_1$-C$_4$)amino, chlorophenyl, methylphenyl, C$_3$-C$_8$ straight or branched alkenyloxy optionally substituted with one to three halogens, C$_3$14 C$_8$ straight or branched alkynyloxy optionally substituted with one to three halogens, or phenoxy substituted with one Cl, CF$_3$, NO$_2$ or CH$_3$ groups, with the proviso that only one of L, M, R$_7$ or R$_8$ may represent a substituent other than hydrogen, halogen, C$_1$-C$_4$ alkyl or C$_1$-C$_4$ alkoxy; and when R$_1$ and R$_2$ are not the same, the cis- and trans-isomers or mixtures thereof or the optical isomers (cis- or trans- or mixtures thereof).

14. A method according to claim 11, wherein said compound has the structure:

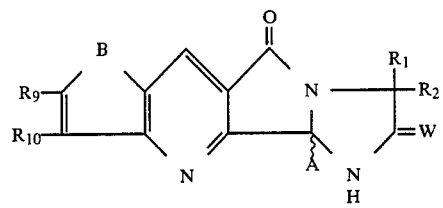

wherein A, R$_1$, R$_2$, W and B, are as defined above in said claim 11; R$_9$ and R$_{10}$ each represent hydrogen, halogen, C$_1$-C$_4$ alkyl or phenyl; and when R$_1$ and R$_2$ are not the same, the cis- and trans-isomers or mixtures thereof or the optical isomers (cis- or trans- or mixtures thereof).

15. A method according to claim 11, having the structure:

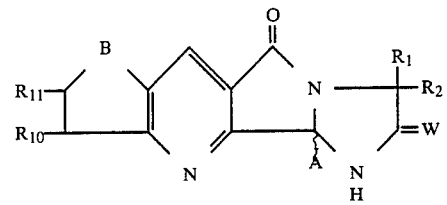

wherein A, R$_1$, R$_2$, W and B, are as defined above in said claim 11; R$_{11}$ and R$_{12}$ each represent hydrogen, C$_1$-C$_4$ alkyl or phenyl; and when R$_1$ and R$_2$ are not the same, the cis- and trans-isomers or mixtures thereof or the optical isomers (cis- or trans- or mixtures thereof).

16. A method according to claim 11, having the structure:

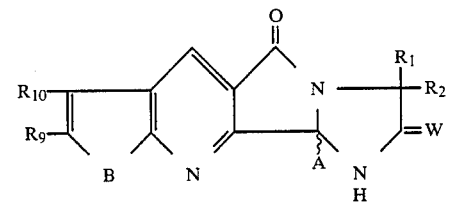

wherein A, R$_1$, R$_2$, W and B, are as defined above in claim 11; R$_9$ and R$_{10}$ each represent hydrogen, halogen, C$_1$-C$_4$ alkyl or phenyl; and when R$_1$ and R$_2$ are not the same, the cis- or trans-isomers or mixtures thereof or the optical isomers (cis- or trans- or mixtures thereof).

17. A method according to claim 11, wherein the compound has the structure:

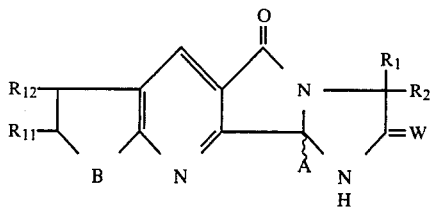

wherein A, $R_1$, $R_2$, W and B, are as defined above in said claim 11; $R_{11}$ and $R_{12}$ each represent hydrogen, $C_1$-$C_4$ alkyl or and phenyl; and when $R_1$ and $R_2$ are not the same, the cis- or trans-isomers or mixtures thereof or the optical isomers (cis- or trans- or mixtures thereof).

18. A method for the selective control of undesirable monocotyledonous and dicotyledonous plant species in the presence of graminaceous crops, leguminous crops or cotton, comprising: applying to the locus in which said crops are planted or growing, effective amount of a compound having the structure:

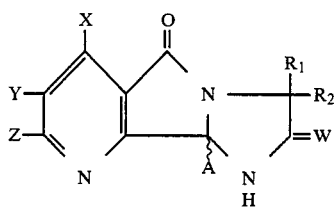

wherein
A, $R_1$ and $R_2$ each represent $C_1$-$C_3$ alkyl or cyclopropyl, with the proviso that the sum of the number of carbon atoms in $R_1$ and $R_2$ is 2 to 5; and when $R_1$ and $R_2$ are taken together with the carbon to which they are attached, they may form a $C_3$-$C_6$ cycloalkyl ring optionally substituted with methyl;

W is oxygen or sulfur;

A is hydrogen, hydroxyl, $C_3$-$C_6$ alkenyloxy, $C_3$-$C_6$ alkynyloxy, $C_1$-$C_6$ alkylthio, $NR_{13}R_{14}$ or $C_1$-$C_6$ alkoxy optionally substituted with phenyl, halophenyl, $C_1$-$C_3$ alkylphenyl, $C_1$-$C_3$ alkoxyphenyl or di-$C_1$-$C_3$ alkylaminophenyl;

$R_{13}$ is hydrogen, $C_1$-$C_4$ alkyl optionally substituted with phenyl, halophenyl, $C_1$-$C_3$ alkylphenyl or $C_1$-$C_3$ alkoxyphenyl;

$R_{14}$ is hydrogen or $C_1$-$C_4$ alkyl;

X is hydrogen, halogen or methyl;

Y and Z are each hydrogen, halogen, $C_1$-$C_6$ alkyl, $C_1$-$C_4$ hydroxyalkyl, $C_1$-$C_6$ alkoxy, $C_1$-$C_4$ alkylthio, phenoxy, $C_1$-$C_4$ haloalkyl, $OCF_2CHF_2$, $OCF_3$, $OCHF_2$, nitro, cyano, $NR_4R_5$, $C_3$-$C_8$ straight or branched alkenyloxy optionally substituted with one to three halogens, $C_3$-$C_8$ straight or branched alkynyloxy optionally substituted with one to three halogens, or phenyl optionally substituted with one $C_1$-$C_4$ alkyl, $C_1$-$C_4$ alkoxy or halogen;

$R_4$ is hydrogen or $C_1$-$C_4$ alkyl;

$R_5$ is $C_1$-$C_4$ alkyl;

And, when taken together, Y and Z may form a ring in which YZ is represented by (1) the structure: —$(CH_2)_n$—, where n is an integer of 2, 3 or 4, provided that X is hydrogen; or (2) by the structure:

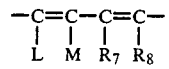

where, L, M, $R_7$ and $R_8$ each represent hydrogen, halogen, $C_1$-$C_4$ alkyl, $C_1$-$C_4$ alkoxy, $C_1$-$C_4$ alkylthio, $C_1$-$C_4$ alkylsulfonyl, $C_1$-$C_4$ haloalkyl, $NO_2$, CN, phenyl, phenoxy, amino, $OCF_3$, $OCHF_2$, $OCF_2CHF_2$, $C_1$-$C_4$ alkylamino, dialkyl($C_1$-$C_4$)amino, chlorophenyl, methylphenyl, $C_3$-$C_8$ straight or branched alkenyloxy optionally substituted with one to three halogens, $C_3$-$C_8$ straight or branched alkynyloxy optionally substituted with one to three halogens, or phenoxy substituted with one Cl, $CF_3$, $NO_2$ or $CH_3$ group, with the proviso that only one of L, M, $R_7$ or $R_8$, may represent a substituent other than hydrogen, halogen, $C_1$-$C_4$ alkyl or $C_1$-$C_4$ alkoxy; or (3) by the structures:

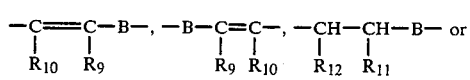

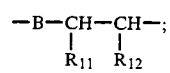

where B is oxygen or sulfur; $R_9$ and $R_{10}$ each represent hydrogen, halogen, phenyl, or $C_1$-$C_4$ alkyl; $R_{11}$ and $R_{12}$ each represent hydrogen, $C_1$-$C_4$ alkyl and phenyl;

and when $R_1$ and $R_2$ are not the same, the cis- or trans-isomers or mixtures thereof or the optical isomers (cis- or trans- or mixtures thereof).

19. A method according to claim 11, wherein said compound is applied at the rate of from about 0.063 to 8.0 kg/ha.

20. A method according to claim 11, wherein said compound is applied to the locus in which said crops are planted or growing at a rate of from 0.063 to 4.0 kg/ha.

21. A herbicidal composition comprising a herbicidally effective amount of a compound having the structure:

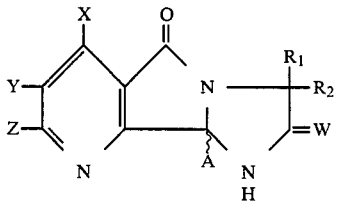

wherein
$R_1$ and $R_2$ each represent $C_1$-$C_3$ alkyl or cyclopropyl, with the proviso that the sum of the number of carbon atoms in $R_1$ and $R_2$ is 2 to 5; and when $R_1$ and $R_2$ are taken together with the carbon to which they are attached, they may form a $C_3$-$C_6$ cycloalkyl ring optionally substituted with methyl;

W is oxygen or sulfur;

A is hydrogen, hydroxyl, $C_3$-$C_6$ alkenyloxy, $C_3$-$C_6$ alkynyloxy, $C_1$-$C_6$ alkylthio, $NR_{13}R_{14}$ or $C_1$-$C_6$ alkoxy optionally substituted with phenyl, halophenyl, $C_1$-$C_3$ alkylphenyl, $C_1$-$C_3$ alkoxyphenyl or di-$C_1$-$C_3$ alkylaminophenyl;

$R_{13}$ is hydrogen, $C_1$-$C_4$ alkyl optionally substituted with phenyl, halophenyl, $C_1$-$C_3$ alkylphenyl or $C_1$-$C_3$ alkoxyphenyl;

$R_{14}$ is hydrogen or $C_1$-$C_4$ alkyl;

X is hydrogen, halogen or methyl;

Y and Z are each hydrogen, halogen, $C_1$-$C_6$ alkyl, $C_1$-$C_4$ hydroxyalkyl, $C_1$-$C_6$ alkoxy, $C_1$-$C_4$ alkylthio, phenoxy, $C_1$-$C_4$ haloalkyl, $OCF_2CHF_2$, $OCF_3$, $OCHF_2$, nitro, cyano, $NR_4R_5$, $C_3$-$C_8$ straight or branched alkenyloxy optionally substituted with one to three halogens, $C_3$-$C_8$ straight or branched alkynyloxy optionally substituted with one to three halogens, or phenyl optionally substituted with one $C_1$-$C_4$ alkyl, $C_1$-$C_4$ alkoxy or halogen;

$R_4$ is hydrogen or $C_1$-$C_4$ alkyl;

$R_5$ is $C_1$-$C_4$ alkyl;

And, when taken together, Y and Z may form a ring in which YZ is represented by (1) the structure: —$(CH_2)_n$—, where n is an integer of 2, 3 or 4, provided that X is hydrogen; or (2) by the structure:

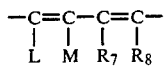

where, L, M, $R_7$ and $R_8$ each represent hydrogen, halogen, $C_1$-$C_4$ alkyl, $C_1$-$C_4$ alkoxy, $C_1$-$C_4$ alkylthio, $C_1$-$C_4$ alkylsulfonyl, $C_1$-$C_4$ haloalkyl, $NO_2$, CN, phenyl, phenoxy, amino, $OCF_3$, $OCHF_2$, $OCF_2CHF_2$, $C_1$-$C_4$ alkylamino, dialkyl($C_1$-$C_4$-)amino, chlorophenyl, methylphenyl, $C_3$-$C_8$ straight or branched alkenyloxy optionally substituted with one to three halogens, $C_3$-$C_8$ straight or branched alkynyloxy optionally substituted with one to three halogens, or phenoxy substituted with one Cl, $CF_3$, $NO_2$ or $CH_3$ group, with the proviso that only one of L, M, $R_7$ or $R_8$, may represent a substituent other than hydrogen, halogen, $C_1$-$C_4$ alkyl or $C_1$-$C_4$ alkoxy; or where B is oxygen or sulfur; $R_9$ and $R_{10}$ each represent hydrogen, halogen, phenyl, or $C_1$-$C_4$ alkyl; $R_{11}$ and $R_{12}$ each represent hydrogen, $C_1$-$C_4$ alkyl or phenyl;

and when $R_1$ and $R_2$ are not the same, the cis- or trans-isomers or mixtures thereof or the optical isomers (cis- or trans- or mixtures thereof); and a non-toxic solid or liquid inert diluent therefore.

* * * * *